(12) United States Patent
Sucheck et al.

(10) Patent No.: US 10,206,988 B2
(45) Date of Patent: Feb. 19, 2019

(54) XENOANTIGEN-DISPLAYING ANTI-CANCER VACCINES AND METHOD OF MAKING

(71) Applicant: The University of Toledo, Toledo, OH (US)

(72) Inventors: Steven J. Sucheck, Maumee, OH (US); Katherine A. Wall, Toledo, OH (US); Sourav Sarkar, Toledo, OH (US)

(73) Assignee: The University Of Toledo, Toledo, OH (US)

( * ) Notice: Subject to any disclaimer, the term of this patent is extended or adjusted under 35 U.S.C. 154(b) by 0 days.

(21) Appl. No.: 15/362,233

(22) Filed: Nov. 28, 2016

(65) Prior Publication Data

US 2017/0072037 A1    Mar. 16, 2017

Related U.S. Application Data

(62) Division of application No. 14/378,805, filed as application No. PCT/US2013/026271 on Feb. 15, 2013, now abandoned.

(60) Provisional application No. 61/599,925, filed on Feb. 16, 2012.

(51) Int. Cl.

| | |
|---|---|
| *A61K 39/00* | (2006.01) |
| *A61K 9/00* | (2006.01) |
| *A61K 39/39* | (2006.01) |
| *A61K 9/127* | (2006.01) |
| *C07K 16/12* | (2006.01) |
| *C07K 16/30* | (2006.01) |
| *C07C 323/60* | (2006.01) |
| *C07K 7/06* | (2006.01) |
| *C07K 7/08* | (2006.01) |
| *C07K 14/47* | (2006.01) |
| *C07K 14/705* | (2006.01) |
| *A61K 47/54* | (2017.01) |
| *A61K 47/69* | (2017.01) |

(52) U.S. Cl.
CPC ........ *A61K 39/0011* (2013.01); *A61K 9/0019* (2013.01); *A61K 9/127* (2013.01); *A61K 39/0012* (2013.01); *A61K 39/39* (2013.01); *A61K 47/543* (2017.08); *A61K 47/6925* (2017.08); *C07C 323/60* (2013.01); *C07K 7/06* (2013.01); *C07K 7/08* (2013.01); *C07K 14/4727* (2013.01); *C07K 14/705* (2013.01); *C07K 16/1275* (2013.01); *C07K 16/3092* (2013.01); *A61K 2039/55516* (2013.01); *A61K 2039/55555* (2013.01); *A61K 2039/55572* (2013.01); *A61K 2039/6018* (2013.01); *A61K 2039/627* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 6,248,329 B1* | 6/2001 | Chandrashekar .. | C07K 14/4354 424/130.1 |
| 7,820,797 B2 | 10/2010 | Boons | |
| 2006/0069238 A1* | 3/2006 | Koganty ............ | A61K 39/0011 530/329 |
| 2009/0041836 A1 | 2/2009 | Boons et al. | |
| 2010/0240773 A1 | 9/2010 | Korzekwa et al. | |
| 2012/0035115 A1 | 2/2012 | Manoharan et al. | |

FOREIGN PATENT DOCUMENTS

| | | |
|---|---|---|
| FR | 2854896 A1 | 11/2004 |
| WO | 2007/079448 A2 | 7/2007 |
| WO | 2009/025168 A1 | 2/2009 |
| WO | 2010/002478 A2 | 1/2010 |
| WO | 2011/156751 A2 | 12/2011 |

OTHER PUBLICATIONS

The Dictionary of Immunology, Herbert et al eds, Academic Press, 1995, 3 pages.*
Feng et al (Infection and Immunity, 64(1): pp. 363-365, 1996).*
Bardonnet et al., "Cholesteryl oligoethyleneglycol glycosides: Fluidizing effect of their embedment into phospholipid bilayers," Biochemical and Biophysical Research Communications, 2005, vol. 329, No. 4, pp. 1186-1192.
Boronat et al., "Metabolism of L-Fucose and L-Rhamnose in *Escherichia coli*: Differences in Induction of Propanediol Oxidoreductase", Journal of Bacteriology, 1981, vol. 147, No. 1, pp. 181-185.
Buskas et al., "Towards a Fully Synthetic Carbohydrate-Based Anticancer Vaccine: Synthesis and Immunological Evaluation of a Lipidated Glycopeptide Containing the Tumor-Associated Tn Antigen", Angewandte Chemie International Edition, 2005, vol. 44, pp. 5985-5988.
Droumaguet et al., "Click Chemistry: A Powerful Tool to Create Polymer-Based Macromolecular Chimeras", Macromolecular Rapid Communications, 2008, vol. 29, pp. 1073-1089.
Ekkebus et al., "On Terminal Alkynes That Can React With Active-Site Cysteine Nucleophiles in Proteases", Journal of the American Chemical Society, 2013, vol. 135, pp. 2867-2870.
Frisch et al., "Conjugation of Ligands to the Surface of Preformed Liposomes by Click Chemistry", Liposomes, Methods in Molecular Biology, 2010, vol. 605, pp. 267-277.
"Lipid", Britannica Online Encyclopedia, pp. 1-22, Web Accessed Aug. 28, 2015.

(Continued)

*Primary Examiner* — Thomas S Heard

(74) *Attorney, Agent, or Firm* — MacMillan, Sobanski & Todd, LLC

(57) ABSTRACT

Compositions, methods of making, and methods of using, xenoantigen-displaying anti-cancer vaccines are described.

12 Claims, 49 Drawing Sheets

Specification includes a Sequence Listing.

(56) References Cited

OTHER PUBLICATIONS

Metzger et al., "Synthesis if Nα-Fmoc protected derivatives of S-(2,3-dihydroxypropyl)-cysteine and their application in peptide synthesis", The International Journal of Peptide Research, 1991, vol. 38, pp. 545-554.

Sarkar et al., "Synthesis of a Single-Molecule L-Rhamnose-Containing Three-Components Vaccine and Evaluation of Antigenicity in the Presence of Anti-I-Rhamnose Antibodies", Journal of the American Chemical Society, 2010, vol. 132, No. 48, pp. 17236-17246.

Sarkar et la., "Carb-70: Evaluation of in vitro T-cell proliferation for a L-Rhamnose displaying MUC1-based anticancer vaccine", American Chemical Society, 2012, vol. 244, No. 19, Abstract Only.

Zeng et al., "Structural requirement for the agonist activity of the TLR2 ligand Pam2Cys", Amino Acids, 2010, vol. 39, pp. 471-480.

Zeng et al., "Synthesis of a New Template with a Built-in Adjuvant and Its Use in Constructing Peptide Vaccine Candidates Through Polyoxime Chemistry", Journal of Peptide Science, 1996, vol. 2, pp. 66-72.

Australian Patent Examination Report No. 1, Application No. AU 2013221448 dated Nov. 24, 2016.

European Search Report, Application No. 13749613.9, dated Dec. 22, 2015.

European Search Report, Application No. 13749613 dated Mar. 16, 2016.

PCT International Search Report and the Written Opinion, Application No. PCT/US2013/026271 filed Feb. 15, 2013, dated Jun. 25, 2013.

* cited by examiner

II

III

IV          V

II

VI

VII

VIII

IX

Scheme 1ª. Synthesis of L-Rhamnose-TEG-Cholesterol 3

ªReagents and conditions: (a) peracetyl L-rhamnose, BF$_3$·OEt$_2$, CH$_2$Cl$_2$, 0 °C - r.t., 18 h, 32%; (b) NaOMe, MeOH, r.t., 1 h, 85% [TEG= CH$_2$CH$_2$(OCH$_2$CH$_2$)$_3$].

aReagents and conditions: (a) (i) 25% piperidine, DMF, r.t. 30 min; (ii) HOBt, DIC, NMP, FmocNH-Ser(Ot-Bu)-OH, repeat steps with T, V, G, H, A, P, P, A, T(Ac$_3$α-GalNAc), S, G, P, A, P, R, T, D, P, 5-azido hexanoic acid; (b) 88% TFA, 3% thioanisole, 5% ehanedithiol, 2% water and 2% phenol; (c) NaOMe, MeOH, r.t., 2 h, 100%; (d) 6, CuSO$_4$·5H$_2$O, Na-ascorbate, TBTA, water-methanol-THF (1:1:2), r.t., 40 h, (100%).

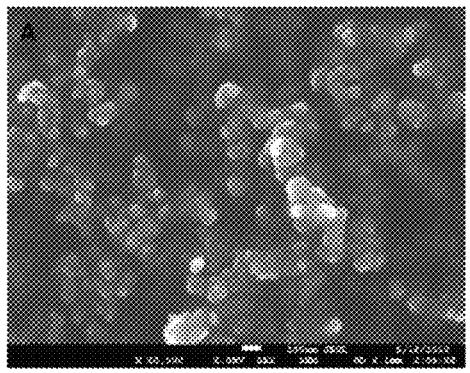
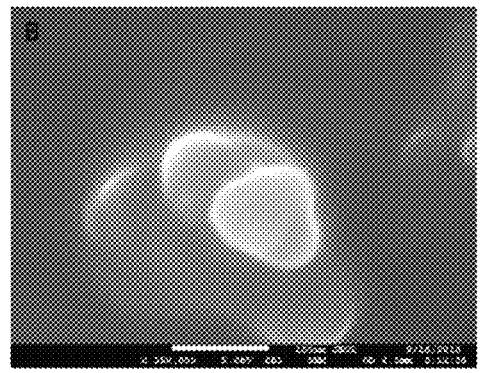
Figure 14A          Figure 14B
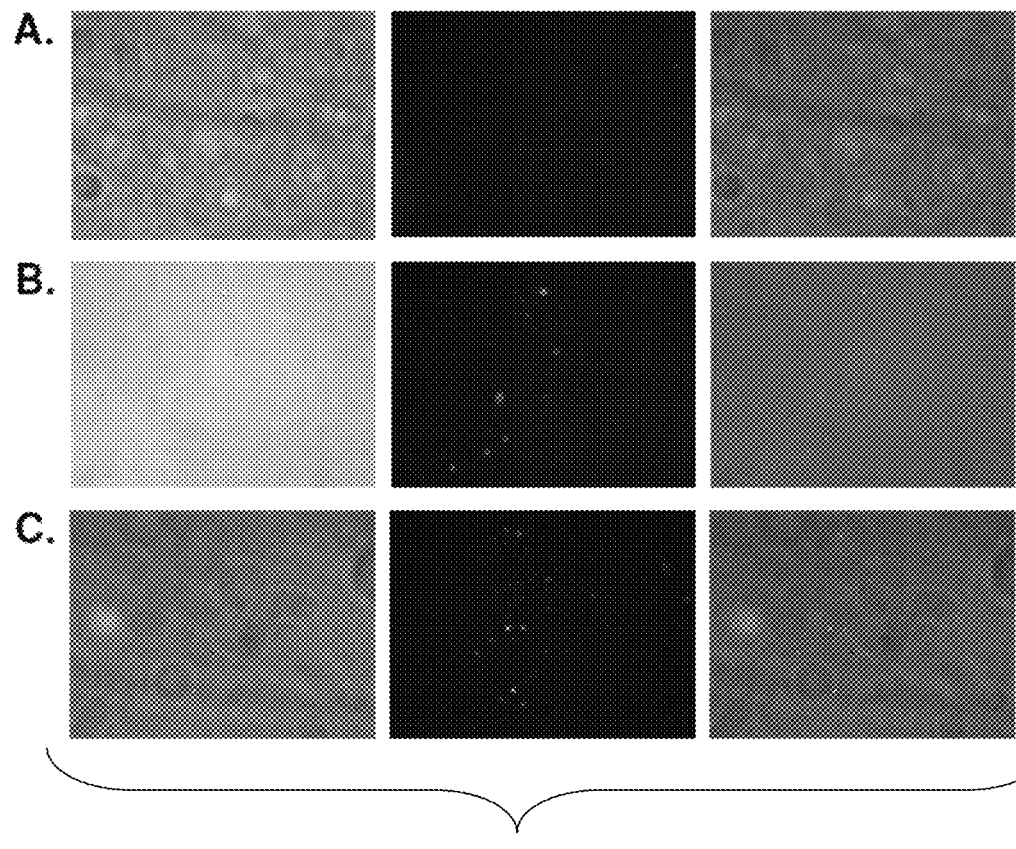
Figures 15A-15C

HR-MALDI-TOF of Glycopeptide Azide 8.

¹H-gCosy of 2-Azidoethyl α-L-rhamnopyranoside (12)

Scheme 4: Synthesis of Pam3Cys-MUC-1 VNTR conjugate 17.[a]

[a] [a]Reagents and conditions: (a) (i) 25% piperidine, DMF, r.t. 30 min; (ii) HOBt, DIC, NMP, FmocNH-Gly-OH, repeat steps with H, A, P, P, A, T, S, G, P, A, P, R, T, D, P, A, S, T, and 5-azido hexanoic acid; (b) 88% TFA, 3% thioanisole, 5% ethanedithiol, 2% water and 2% phenol; (c) 6, CuI, Na-ascorbate, TBTA, DIEA, water-THF-DMF (1:1:2), r.t., 16 h, (100%).

HPLC trace of peptide (16):

Scheme 5: Synthesis of Pam₃Cys-MUC-1 VNTR conjugate 21.ᵃ

ᵃReagents and conditions: (a) (i) 25% piperidine, DMF, r.t. 30 min; (ii) HOBt, DIC, NMP, FmocNH-Ser(Ot-Bu)-OH, repeat steps with , A, P, P, A, T, S, G, P, A, P, R, T(Ac₃α-GalNAc), D, P, A, S, T, 5-azido hexanioc acid; (b) 88% TFA, 3% thioanisole, 5% ethanedithiol, 2% water and 2% phenol; (c) NaOMe, MeOH, r.t., 2 h, 100%; (d) 6, CuI, Na-ascorbate, TBTA, DIEA, water-THF-DMF (1:1:2), r.t., 16 h.

HPLC trace of Glycopeptide (19):

SEQUENCE LISTING

<160> NUMBER OF SEQ ID NOS: 15

<210> SEQ ID NO 1

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Alpha-GalNAc-O-Thr(Tn) TACA

<400> SEQUENCE: 1

Pro Asp Thr Arg Pro Ala Pro Gly Ser Thr Ala Pro Pro Ala His Gly
1               5                   10                  15

Val Thr Ser Ala
            20

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dipalmitoyl-S-glyceryl-Cys

<400> SEQUENCE: 2

Cys Ser Lys Lys Lys Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tripalmitoyl-S-glyceryl-Cys

<400> SEQUENCE: 3

Cys Ser Lys Lys Lys Lys
1               5

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dipalmitoyl-S-glyceryl-Cys

<400> SEQUENCE: 4

Cys Gly Asn Asn Asp Glu Ser Asn Ile Ser Phe Lys Glu Lys
1               5                   10

<210> SEQ ID NO 5
<211> LENGTH: 20
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 5

Thr Ser Ala Pro Asp Thr Arg Pro Ala Pro Gly Ser Thr Ala Pro Pro
1               5                   10                  15

Ala His Gly Val
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Alpha-GalNAc-O-Thr(Tn) TACA

<400> SEQUENCE: 6

Thr Ser Ala Pro Asp Thr Arg Pro Ala Pro Gly Ser Thr Ala Pro Pro
1               5                   10                  15

Ala His Gly Val
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tripalmitoyl-S-glyceryl-Cys
<220> FEATURE:
<221> NAME/KEY: MOD_RES
<222> LOCATION: (11)..(11)
<223> OTHER INFORMATION: Alpha-GalNAc-O-Thr(Tn) TACA

<400> SEQUENCE: 7

Cys Pro Asp Thr Arg Pro Ala Pro Gly Ser Thr Ala Pro Pro Ala His
1               5                   10                  15

Gly Val Thr Ser Ala
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-azido hexanoic acid
<220> FEATURE:
<221> NAME/KEY: MOD_RES
<222> LOCATION: (11)..(11)
<223> OTHER INFORMATION: Thr(Ac3alpha-GalNAc)

<400> SEQUENCE: 8

Xaa Pro Asp Thr Arg Pro Ala Pro Gly Ser Thr Ala Pro Pro Ala His
1               5                   10                  15

Gly Val Thr Ser Ala
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-azido hexanoic acid
<220> FEATURE:
<221> NAME/KEY: MOD_RES
<222> LOCATION: (11)..(11)
<223> OTHER INFORMATION: Thr(Ac3alpha-GalNAc) or alpha-GalNAc-O-Thr(Tn)
      TACA

<400> SEQUENCE: 9

Xaa Pro Asp Thr Arg Pro Ala Pro Gly Ser Thr Ala Pro Pro Ala His
1               5                   10                  15

Gly Val Thr Ser Ala
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-azido hexanoic acid
<220> FEATURE:
<221> NAME/KEY: MOD_RES
<222> LOCATION: (11)..(11)
<223> OTHER INFORMATION: Alpha-GalNAc-O-Thr(Tn) TACA

<400> SEQUENCE: 10

Xaa Pro Asp Thr Arg Pro Ala Pro Gly Ser Thr Ala Pro Pro Ala His
1               5                   10                  15

Gly Val Thr Ser Ala
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-azido hexanoic acid

<400> SEQUENCE: 11

Xaa Thr Ser Ala Pro Asp Thr Arg Pro Ala Pro Gly Ser Thr Ala Pro
1               5                   10                  15

Pro Ala His Gly Val
            20

<210> SEQ ID NO 12
<211> LENGTH: 21
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tripalmitoyl-S-glyceryl-Cys

<400> SEQUENCE: 12

Cys Thr Ser Ala Pro Asp Thr Arg Pro Ala Pro Gly Ser Thr Ala Pro
1               5                   10                  15

Pro Ala His Gly Val
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-azido hexanoic acid
<220> FEATURE:
<221> NAME/KEY: MOD_RES
<222> LOCATION: (7)..(7)
<223> OTHER INFORMATION: Thr(Ac3alpha-GalNAc)

<400> SEQUENCE: 13

Xaa Thr Ser Ala Pro Asp Thr Arg Pro Ala Pro Gly Ser Thr Ala Pro
1               5                   10                  15

Pro Ala His Gly Val
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-azido hexanoic acid
<220> FEATURE:
<221> NAME/KEY: MOD_RES
<222> LOCATION: (7)..(7)
<223> OTHER INFORMATION: Thr(Ac3alpha-GalNAc) or alpha-GalNAc-O-Thr(Tn)
      TACA

<400> SEQUENCE: 14

Xaa Thr Ser Ala Pro Asp Thr Arg Pro Ala Pro Gly Ser Thr Ala Pro
1               5                   10                  15

Pro Ala His Gly Val
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Tripalmitoyl-S-glyceryl-Cys
<220> FEATURE:
<221> NAME/KEY: MOD_RES
<222> LOCATION: (7)..(7)
<223> OTHER INFORMATION: Alpha-GalNAc-O-Thr(Tn) TACA

<400> SEQUENCE: 15

Cys Thr Ser Ala Pro Asp Thr Arg Pro Ala Pro Gly Ser Thr Ala Pro
1               5                   10                  15

Pro Ala His Gly Val
            20
```

XENOANTIGEN-DISPLAYING ANTI-CANCER VACCINES AND METHOD OF MAKING

CROSS-REFERENCE TO RELATED APPLICATIONS

This is a divisional application of U.S. application Ser. No. 14/378,805, filed under 35 U.S.C. § 371 on Aug. 14, 2014, published; which is the national stage entry of international application PCT/US13/26271, filed under the authority of the Patent Cooperation Treaty on Feb. 15, 2013, published; which claims the benefit of U.S. Provisional Application No. 61/599,925, filed under 35 U.S.C. § 111(b) on Feb. 16, 2012. The entire disclosures of all the aforementioned applications are hereby expressly incorporated by reference for all purposes.

STATEMENT REGARDING FEDERALLY SPONSORED RESEARCH

The invention was made with U.S. Government support under Grant Number GM094734 awarded by the National Institutes of Health. The United States Government has certain rights in the invention.

SEQUENCE LISTING

The instant application contains a Sequence Listing which has been submitted via EFS-web and is hereby incorporated by reference in its entirety. The ASCII copy, created on Feb. 12, 2013, is named 420_53665_SEQ_LIST_D2012-14.txt, and is 6,494 bytes in size.

TECHNICAL FIELD AND INDUSTRIAL APPLICABILITY OF THE INVENTION

The invention relates to compositions having a xenoantigen that is incorporated onto a target antigen and method of making the same. In particular, there is provided herein a vaccine composition comprised of a lipid-linked antigen in non-covalent association with a lipid-linked xenoantigen, where both the lipid-linked antigen and the lipid-linked xenoantigen are independently embedded in liposomes in a liposomal formulation.

BACKGROUND

The use of vaccines against a variety of agents is an important objective for disease control worldwide. It is understood that the protective immunity afforded by vaccines against specific antigen is achieved by humoral, cellular and mucosal immune responses.

For example, humoral or antibody responses are important in pathogen neutralization and can be very effective in some conditions such as cancer and infectious diseases. These therapeutic cancer vaccines are a new class of active specific immunotherapy agents that trigger a targeted immune response against cancer. It would be useful to have efficient methods for the synthesis of such vaccines in addition to those presently available.

SUMMARY

In a first aspect, there is provided herein a composition comprising a first lipid ($lipid_a$) moiety and an alkyne amide moiety having a Formula IV.

In certain embodiments, the first lipid ($lipid_a$) moiety comprises a Toll-like receptor (TLR) agonist ligand selected from one or more of: TLR2, TLR1, TLR3, TLR4, TLR5, TLR6, TLR7, TLR8, TLR9, TLR10, TLR11, TLR12, TLR13, TLR14, TLR15 and TLR16.

In certain embodiments, the TLR2 ligand comprises: dipalmitoyl-S-glyceryl-cys-($Pam_2Cys$-); tripalmitoyl-S-glyceryl-cys-($Pam_3Cys$-); dipalmitoyl-S-glyceryl-cys-ser-lys-lys-lys-lys ($Pam_2Cys$-Ser-$(Lys)_4$) [SEQ ID NO: 2]; tripalmitoyl-S-glyceryl-cys-ser-lys-lys-lys-lys ($Pam_3Cys$-Ser-$(Lys)_4$) [SEQ ID NO: 3]; or MALP-2 dipalmitoyl-S-glyceryl-cys-gly-asn-asn-asp-glu-ser-asn-ile-ser-phe-lys-glu-lys ($Pam_2$CGNNDESNISFKEK)] [SEQ ID NO: 4].

In certain embodiments, the Formula IV comprises an alkyne-functionalized $Pam_3Cys$ amide composition (6), wherein Pam is a dipalmitoyl-S-glyceryl-moiety.

In another broad aspect, there is provided herein a method of synthesizing an alkyne-functionalized composition of claim 1, comprising: deprotecting an ester comprising a Fmoc moiety to form a free acid; coupling the free acid of step (a) with an amine; and, removing the Fmoc moiety, and coupling the remaining moiety with palmitic acid to yield an alkyne-functionalized composition.

In another broad aspect, there is provided herein a method of synthesizing an alkyne-functionalized Pam3Cys amide composition (6), comprising:

a) deprotecting O-palmitoylated Fmoc L-cystine tert-butyl ester (4) to form a free acid;

b) coupling the free acid of step (a) with propargyl amine in presence of benzotriazol-1-yl-oxytripyrrolidinophosphonium hexafluorophosphate (PyBOP), 1-hydroxy-benzotriazole (HOBt) and N,N-diisopropylethylamine (DIPEA) to yield composition (5); and, c) removing a Fmoc group of composition (5) by treatment with a mixture of acetonitrile-dichloromethane-diethyl amine, followed by subsequent palmitoylation by coupling with palmitic acid, PyBOP, HOBt and DIPEA to yield the alkyne-functionalized Pam3Cys amide composition (6).

In another broad aspect, there is provided herein a lipidated glycopeptide composition comprising: a first lipid (lipida) moiety, a first linker (linkera) moiety, and an antigen moiety having a Formula II.

In certain embodiments, the first lipid (lipida) moiety comprises a Toll-like receptor (TLR) agonist ligand selected from one or more of: TLR2, TLR1, TLR3, TLR4, TLR5, TLR6, TLR7, TLR8, TLR9, TLR10, TLR11, TLR12, TLR13, TLR14, TLR15 and TLR16.

In certain embodiments, the first lipid (lipida) moiety comprises a TLR2 ligand comprising:
dipalmitoyl-S-glyceryl-cys-(Pam2Cys-);
tripalmitoyl-S-glyceryl-cys-(Pam3Cys-);
dipalmitoyl-S-glyceryl-cys-ser-lys-lys-lys-lys (Pam2Cys-Ser-(Lys)4) [SEQ ID NO: 2];
tripalmitoyl-S-glyceryl-cys-ser-lys-lys-lys-lys
(Pam3Cys-Ser-(Lys)4) [SEQ ID NO: 3];
or MALP-2 dipalmitoyl-S-glyceryl-cys-gly-asn-asn-asp-glu-ser-asn-ile-ser-phe-lys-glu-lys
(Pam2CGNNDESNISFKEK)] [SEQ ID NO: 4].

In certain embodiments, the antigen moiety comprises: an anti-cancer composition, an anti-bacterial composition, an anti-viral composition, a protein, an isolated DNA, an isolated RNA, an isolated carbohydrate, or an isolated lipid.

In certain embodiments, the antigen moiety comprises a TACA that interacts with B-cell receptors.

In certain embodiments, the TACA comprises one or more glycoproteins and glycolipids on a cancer cell.

In certain embodiments, the composition comprises mucin 1 (MUC1) variable number tandem repeats (VNTRs) conjugated to tumor-associated carbohydrate antigens (TACA).

In certain embodiments, the TACA comprises: TF, Tn, sialyl Tn (sTn), or sialyl Lewis a (sLea) antigens.

In certain embodiments, the TACA comprises: an autologous or heterologous helper T-cell epitope, wherein the autologous or heterologous helper T-cell epitope comprises a sequence expressed on a tumor cell.

T In certain embodiments, the autologous or heterologous helper T-cell epitope comprises MUC1 VNTR having one of the following amino acid sequences:

PDTRPAPGST(Tn)APPAHGVTSA; [SEQ ID NO: 1]

TSAPDTRPAPGSTAPPAHGV; [SEQ ID NO: 5]
or,

TSAPDT(Tn)RPAPGSTAPPAHGV. [SEQ ID NO: 6]

In certain embodiments, the threonine in the sequence GST or PDT is synthetically modified to incorporate α-GalNAc-O-Thr (Tn) TACA.

In certain embodiments, the first linker (linkera) comprises a dialkyl-substituted heteroaryl C1-n alkyl of Formula VI, wherein the "A" group comprises: a chain of C1-n alkyl, dialkyl substituted aryl C1-n alkyl, or —CH2CH2 (OCH2CH2)n-; and n is a positive integer.

In certain embodiments, the "A" group comprises a C1-5 alkyl chain.

In another broad aspect, there is provided herein a composition comprising the compound (9).

In another broad aspect, there is provided herein a composition comprising the compound (17).

In another broad aspect, there is provided herein a composition comprising the compound (21).

In another broad aspect, there is provided herein a method of synthesizing a lipidated glycopeptide composition, comprising reacting a composition of Formula IV, with a composition Formula V.

In another broad aspect, there is provided herein a method of synthesizing a Pam3Cys-MUC-1 VNTR-TACA conjugate, comprising: synthesizing a 20-amino acid tandem repeat of MUC1; and modifying a glycopeptide with a terminal azido group to make a 'click' conjugation to a Pam3Cys alkyne.

In certain embodiments, the 20-amino acid tandem repeat of MUC1 comprises a GS(α-GalNAc-O-T)A epitope.

In certain embodiments, the 20-amino acid tandem repeat of MUC1 comprises a PD(α-GalNAc-O-T)R epitope.

In another broad aspect, there is provided herein a composition comprising a second lipid (lipidb) moiety, a second linker (linkerb) moiety, and a xenoantigen moiety, having the Formula VII.

In certain embodiments, the second lipid (lipidb) moiety contains a structure of the Formula IX.

In certain embodiments, the second linker (linkerb) comprises: a chain of C1-n alkyl, dialkyl substituted aryl C1-n alkyl, or —CH2CH2(OCH2CH2)n-; wherein n is a positive integer.

In certain embodiments, the second linker (linkerb) comprises a tetraethyleneglycol (TEG) of Formula VIII.

In certain embodiments, the xenoantigen moiety comprises a xenoantigen linked to a lipid.

In certain embodiments, the xenoantigen binds a natural antibody (NA).

In certain embodiments, the NA comprises an autoantigen that is present in blood.

In certain embodiments, the NA comprises IgM, IgG, or IgA isotypes in human blood.

In certain embodiments, the NA comprises an anti-carbohydrate NA in human serum.

In certain embodiments, the xenoantigen moiety contains a structure comprising: an α- or β-linked L-rhamnose epitope, a β-linked α-Gal disaccharide epitope, or an α- or β-linked Forssmann disaccharide epitope:

In another broad aspect, there is provided herein a vaccine composition, comprising: an antigen composition comprising:
1) a first lipid (lipida) moiety, a first linker (linkera) moiety, and an antigen moiety;
2) a xenoantigen composition comprising: a second lipid (lipidb) moiety, a second linker (linkerb) moiety, and a xenoantigen moiety; and,
3) at least one liposomal formulation.

In another broad aspect, there is provided herein a vaccine composition, wherein a lipid-linked antigen is in non-covalent association with a lipid-linked xenoantigen, and wherein both the lipid-linked antigen and the lipid-linked xenoantigen are independently embedded in liposomes in a liposomal formulation.

In certain embodiments, there is no chemically synthesized complex xenoantigen-antigen conjugate molecule.

In certain embodiments, the liposomal formulation comprises 1,2-dipalmitoyl-sn-glycero-3-phosphocholine (DPPC) and cholesterol in a ratio of from about 80:20 to about 70:30, respectively.

In another broad aspect, there is provided herein a vaccine composition of claim 37, wherein: the antigen composition comprises a Pam3Cys-MUC1 VNTR-TACA conjugate; the second linker (linkerb) moiety comprises a tetraethyleneglycol (TEG) portion; and the xenoantigen moiety comprises α- or β-linked L-rhamnose.

In another broad aspect, there is provided herein an anti-cancer vaccine comprising a vaccine composition as described herein In another broad aspect, there is provided herein an anti-viral vaccine comprising a vaccine composition as described herein.

In another broad aspect, there is provided herein an anti-bacterial vaccine comprising a vaccine composition as described herein.

In certain embodiments, the vaccine composition further includes at least one immunologic adjuvant.

In certain embodiments, the immunologic adjuvant comprises one or more of: a saponin, monophosphoryl lipid A, 3'-O-deacylated monophosphoryl lipid A, and interleukin 12.

In another broad aspect, there is provided herein a method for eliciting an immune response to a cancer cell surface antigen in a subject with cancer, comprising administering to the subject an antigen-xenoantigen-liposome composition of claim 37 in sufficient dose to elicit the immune response to the cancer cell surface antigen, wherein the antigen-liposome-xenoantigen composition comprises the cancer cell surface antigen, and wherein the immune response is sufficient for treating the cancer.

In certain embodiments, the both the lipid-linked antigen and the lipid-linked xenoantigen are independently embedded in liposomes in the liposomal formulation.

In certain embodiments, the cancer cell surface antigen is expressed only in cancer cells in the subject.

In certain embodiments, the cancer cell surface antigen is expressed only by cancer cells.

In certain embodiments, the cancer cell surface antigen comprises a peptide epitope.

In certain embodiments, the cell surface antigen comprises MUC1 mucin.

In certain embodiments, the subject is a human or non-human mammal.

In certain embodiments, the antigen-liposome-xenoantigen composition is administered intranasally, intramuscularly, subcutaneously, intravenously, or orally to the subject.

In certain embodiments, the method further comprises measuring humoral and/or cellular immune responses to the cancer cell surface antigen, and administering a further dose to elicit the immune response, if necessary.

In another broad aspect, there is provided herein a method for selectively killing cancer cells expressing a cancer cell surface antigen in a subject in need thereof, comprising administering to the subject an antigen-liposome-xenoantigen composition of claim 27, under conditions that result in production in the subject of antibodies against the cancer cell surface antigen, wherein the antibodies produced bind the cancer cell surface antigen on cancer cells in the subject, thereby killing cancer cells that express the cancer cell surface antigen.

In certain embodiments, both the lipid-linked antigen and the lipid-linked xenoantigen are independently embedded in liposomes in the liposomal formulation.

In certain embodiments, the cancer cell surface antigen is expressed only in cancer cells in the subject.

In certain embodiments, the cancer cell surface antigen is expressed only by cancer cells.

In another broad aspect, there is provided herein a method for improving immunogenicity of vaccines, the method comprising incorporating at least one α- or β-linked L-Rha epitope by direct conjugation or by non-covalent association with at least one liposomal vaccine formulation to increase the immunogenicity of the vaccine by a NA-dependant antigen uptake mechanism.

In another broad aspect, there is provided herein a method of synthesizing an alkyne functionalized composition (IV), comprising: deprotecting an ester having a Fmoc moiety to form a free acid; coupling the free acid with an amine; and, removing the Fmoc moiety, and coupling the remaining moiety with palmitic acid to yield the alkyne functionalized composition.

In certain embodiments, the antigen moiety comprises: an anti-cancer composition, an anti-bacterial composition, or an anti-viral composition.

In certain embodiments, the antigen moiety comprises: a TACA that interacts with B-cell receptors. In certain embodiments, the TACA comprises an autologous helper T-cell epitope.

In one broad aspect, there is provided herein a method of synthesizing component 1) above, comprising reacting an alkyne-functionalized amide derivative with a modified peptide antigen.

In another broad aspect, there is provided herein the composition (VII), where the xenoantigen binds a natural antibody (NA). In certain embodiment, the xenoantigen contains a structure comprised of: α- or β-linked L-rhamnose, a β-linked α-Gal epitope, or an α- or β-linked Forssmann disaccharide epitope.

In another broad aspect, there is provided herein a method for eliciting an immune response to a cancer cell surface antigen in a subject with cancer, comprising administering to the subject an antigen-liposome-xenoantigen composition described herein, in sufficient dose to elicit the immune response to the cancer cell surface antigen.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 13A—Batch 1 liposomes; FIG. 13B—Batch 2 liposomes; and FIG. 13C—Batch 3 liposomes.

FIGS. 14A-14B: Photographs showing size characterization of liposomes: SEM images at 5 kV acceleration voltage. FIG. 14A: Batch 1 liposomes under 50,000× magnification. FIG. 14B: Batch 1 liposomes under 250,000× magnification.

FIGS. 15A-15C: Fluorescence microscope images with Batch 1 liposomes under 60× magnification. FIG. 15A: Images with control antibodies (antibodies isolated from preimmunization serum) 1st, 2nd and 3rd images: brightfield, FITC and overlay. FIG. 15B: Images with anti-rhamnose antibodies, 1st, 2nd and 3rd images: brightfield, FITC and overlay. FIG. 15C: Images with anti-MUC 1 antibodies, 1st, 2nd and 3rd images: brightfield, FITC and overlay.

FIG. 38A) T-cell proliferation measured by [$^3$H]thymidine incorporation in T-cells from mice spleens primed with MUC1-Tn (8) and challenged with Pam$_3$Cys-MUC1-Tn (9)+Rha liposomes in the presence of anti-Rha antibodies (abs) or control abs [anti Rha(OVA) and anti Rha(Ficoll) abs are the antibodies isolated from the serum of Rha-OVA and Rha-Ficoll immunized mice, respectively]. FIG. 38B) Stepwise immunization plan. Groups A1, A2, B1, and B2 each represent four groups of female BALB/c mice. Stage I: groups A2 and B2 were immunized with Rha-Ficoll/Alum whereas groups A1 and B1 were non-immunized. Stage II: vaccination; groups A1 and A2 vaccinated and boosted with Pam$_3$Cys-MUC1-Tn liposomes whereas groups B2 and B2 were vaccinated with Pam$_3$Cys-MUC1-Tn+Rha liposomes.

FIG. 39A) Group average of anti-Rha antibody titers after fourth boost with Rha-Ficoll/Alum. FIG. 39B) Group average of anti-MUC1-Tn antibody titers after first boost with Pam$_3$Cys-MUC1-Tn liposomes or Pam$_3$Cys-MUC1-Tn+Rha liposomes.

FIG. 41A) Competitive binding of anti-MUC1-Tn antibodies with bound MUC1-Tn in presence of free MUC1-Tn (8). FIG. 41B) Groups average of anti-Tn antibody titer after first boost with Pam$_3$Cys-MUC1-Tn liposomes or Pam$_3$Cys-MUC1-Tn+Rha liposomes.

FIG. 42A) Second antibody alone and with mouse anti-human MUC1 antibodies; FIG. 42B) with 1/5 dilution of non-immunized mouse serum, and with 1/5 dilution of group B2 mouse serum.

DETAILED DESCRIPTION

Figure 1:
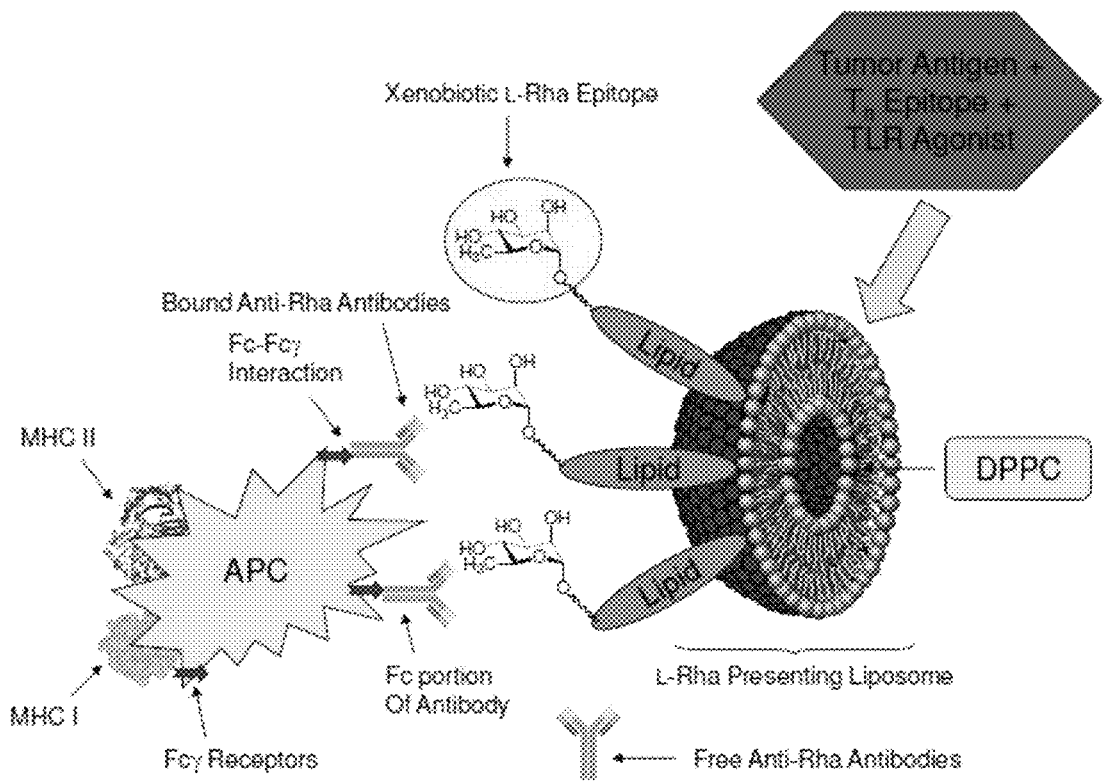
FIG. 1: Schematic representation of Fc-Fcγ receptor interaction in the in vivo generated immune complex and APC leading to enhanced antigen uptake and presentation on MHC I or MHC II (APC=antigen presenting cells, e.g., a dendritic cell).
Figure 2:
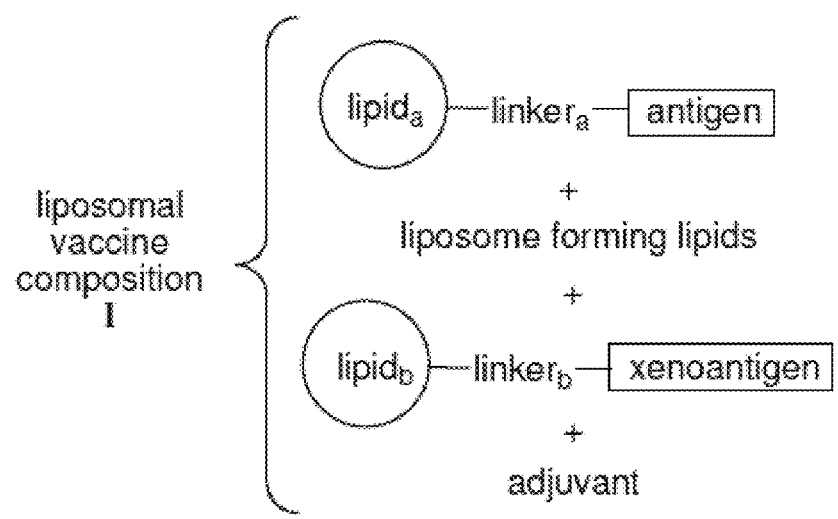
FIG. 2: Schematic illustration of a liposomal vaccine composition comprised of: an antigen composition comprised of a first lipid ($lipid_a$) moiety, a first linker ($linker_a$) moiety, and an antigen moiety; and, a second lipid ($lipid_b$) moiety, a second linker ($linker_b$) moiety, and a xenoantigen moiety; at least one liposome forming lipid; and, optionally, one or more adjuvants.
Figure 3:
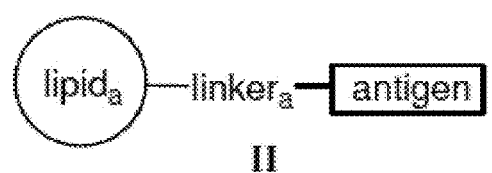
FIG. 3: Schematic illustration of a lipid-linked antigen component.
Figure 4:
FIG. 4: Schematic illustration of a dialkyl-substituted heteroaryl $C_{1-n}$ alkyl component.
Figure 5:
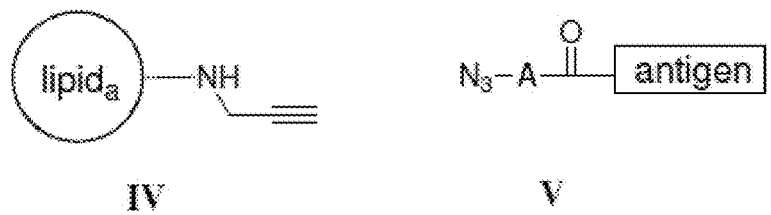
FIG. 5: Schematic illustration of a composition IV reacting with a composition V to form a composition II.
Figure 5:
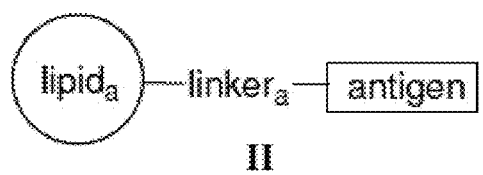

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

General Definitions

The terms "a," "an," and "the" include the plural referents unless the context clearly dictates otherwise.

The term "antibody" broadly refers to monoclonal antibodies (including full length monoclonal antibodies) and "antibody fragments" that exhibit a desired biological activity. "Antibody fragments" can comprise a portion of a full length antibody, generally the antigen binding or variable region thereof. Non-limiting examples of antibody fragments include Fab, Fab', and Fv fragments; diabodies; linear antibodies; and single-chain antibody molecules.

The term "monoclonal antibody" broadly refers to antibodies that are highly specific, being directed against a single antigenic site.

The term "antibody" also broadly includes naturally occurring antibodies (NAs) as well as non-naturally occurring antibodies, including, for example, single chain antibodies, chimeric, bifunctional and humanized antibodies, as well as antigen-binding fragments thereof. For example, such non-naturally occurring antibodies can be constructed using solid phase peptide synthesis, can be produced recombinantly or can be obtained, for example, by screening combinatorial libraries consisting of variable heavy chains and variable light chains.

The term "subject/s" generally refers to any animal that generates an adaptive immune response and can include mammals, birds and reptiles. Examples of subjects can include, but are not limited to, humans, non-human primates, dogs, cats, horses, cows, goats, guinea pigs, mice, rats and rabbits, as well as any other domestic or commercially valuable animal.

The term/s "nucleic acid/s" generally encompass both RNA and DNA, including cDNA, genomic DNA, mRNA, synthetic (e.g., chemically synthesized) DNA and chimeras of RNA and DNA. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

It is to be further understood that the term "$C_{1-n}$ alkyl" can be any linear or branched alkyl group containing 1 to n carbon atoms. For example, the term "$C_{1-6}$ alkyl" can comprise groups such as methyl, ethyl, propyl, isopropyl, butyl, isobutyl, sec-butyl, tert-butyl, pentyl, isopentyl (3-methylbutyl), neopentyl (2,2-dimethylpropyl), hexyl, isohexyl (4-methylpentyl) and the like.

The term "$C_{2-n}$ alkyl" is to be understood to mean any linear or branched alkyl group containing 2 to n carbon atoms. For example, the term "$C_{2-6}$ alkyl" can comprise groups such as ethyl, propyl, isopropyl, butyl, isobutyl, sec-butyl, tert-butyl, pentyl, isopentyl (3-methylbutyl), neopentyl (2,2-dimethylpropyl), hexyl, isohexyl (4-methylpentyl) and the like.

The term "dialkyl-substituted aryl $C_{1-n}$ alkyl" is to be understood to mean an aryl group substituted at two positions wherein the substituents are composed of a $C_{1-n}$ alkyl group, as defined above. The aryl group may be optionally substituted with at least one substituent selected from the group consisting of hydroxyl, $C_{1-2}$ alkoxy and halogen. Examples of dialkyl-substituted aryl $C_{1-n}$ alkyl groups include, but are not limited to:

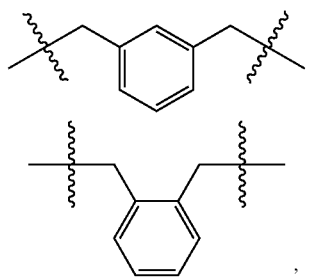

,

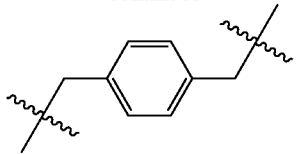

The term "dialkyl-substituted heteroaryl $C_{1-n}$ alkyl" is to be understood to mean a heteroaryl group substituted at two positions wherein the substituents are composed of a $C_{1-n}$ alkyl group, as defined above. The aryl group may be optionally substituted with at least one substituent selected from the group consisting of hydroxyl, $C_{1-2}$ alkoxy and halogen. Examples of substituted heteroaryl $C_{1-n}$ alkyl groups include, but are not limited to:

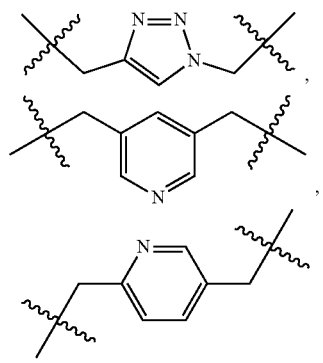

Accordingly, the term "xenoantigen" is to be understood to mean at least one foreign antigen capable of binding natural antibodies. Examples of xenoantigens include, but are not limited to, the α-gal epitope, L-Rha, and the Forssman disaccharide.

The term "peptide" may be any peptide comprising natural or non-natural amino acids; and if chiral, in its L or D configurations or as racemate. Examples of non-natural amino acids include, but are not limited to: homocysteine, homoarginine, cylcohexylalanine, ornithine, and $C^α$ α-dibenzylglycine.

As used herein, the term "lipid" is defined to include any of a broad range of substances that is characteristically insoluble in water and extractable with an organic solvent. This broad class of compounds is known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). Biological lipids are well known in the art and include, for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods described herein.

General Description

In a first broad aspect, there is provided herein a composition having xenoantigen that is incorporated onto a target antigen.

In another broad aspect, there is provided herein a vaccine composition comprising a lipid-linked antigen in non-covalent association with a lipid-linked xenoantigen, where both the lipid-linked antigen and the lipid-linked xenoantigen are independently embedded in liposomes in a liposomal formulation.

In another broad aspect, there is provided herein tumor-associated carbohydrate antigens (TACAs) that are on the heavily glycosylated glycoprotein mucin 1 (MUC1).

In another aspect, the tumor-associated carbohydrate antigens (TACAs) that are on the heavily glycosylated glycoprotein mucin 1 (MUC1) are useful as targets for anticancer active immunotherapy.

In another aspect, there is provided herein the non-covalent association of the L-Rhamnose xenoantigen in a liposome with the other components of a vaccine independently embedded in the liposome. This non-covalent association eliminates the need to chemically synthesize a complex xenoantigen-antigen conjugate molecule.

The peptide sequences described herein act as an autologous helper T-cell epitope. The use of foreign carrier proteins and peptides as conjugates provide helper T-cell epitopes unrelated to the tumor and act as heterologous helper T-cell epitopes.

In one embodiment, the MUC1 sequence described herein is shown to be a potent candidate for generating antibodies.

The glycoconjugates on the surface of cancer cells are expressed in abnormal quantities and show modifications in the structure of the carbohydrate moieties linked to the peptide or lipid components of the conjugates. These aberrant carbohydrate epitopes are specifically known as tumor associated carbohydrate antigens (TACAs). TACAs demonstrate potential as markers for cancer detection and disease progression and therefore are under intense investigation for their role in the development of anti-cancer vaccines.

The TACAs found on the heavily glycosylated glycoprotein mucin 1 (MUC1) are useful targets for anticancer active immunotherapy. In most cancers of epithelial origin, e.g., breast, colorectal, and prostate, this glycoprotein becomes highly over expressed and loses its apical distribution, becoming expressed over the entire cell surface. In the transformed state, the glycan chains of MUC1 are typically shorter and show increased sialylation relative to normal. A number of TACAs have been identified from MUC1. TACAs includes TF, Tn, STn, sLe$^a$ antigens:

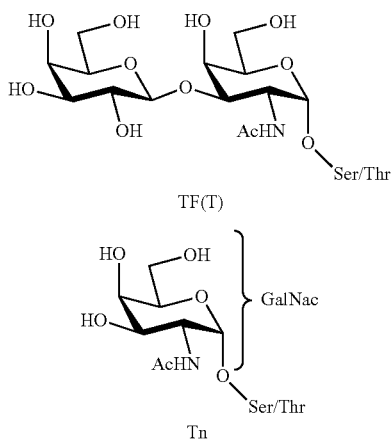

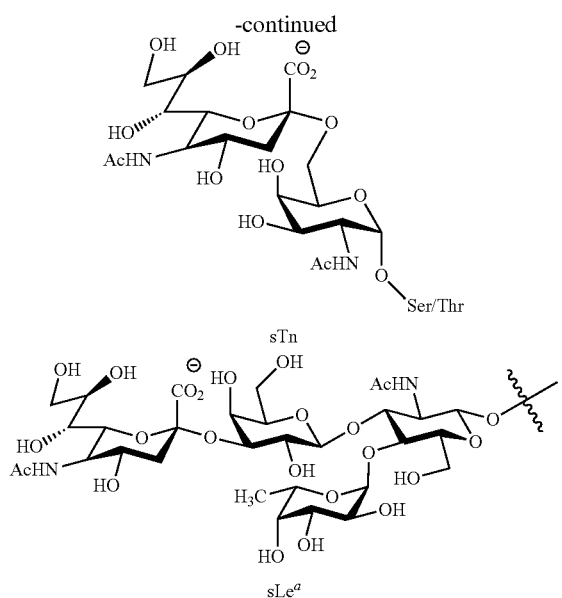

In certain embodiments, the above TACAs (which are found on tumor cells) are useful as the "B-cell epitopes" in the design of the vaccines described herein.

The MUC1 glycoprotein is also shed into the serum and is a tumor marker for cancer. For example, patients possessing naturally occurring anti-MUC1 antibodies demonstrate better disease-specific survival. It is believed that anti-MUC1 antibodies control hematogenous tumor dissemination and outgrowth. It is also now believed that that TACAs present on MUC1 variable number tandem repeat (VNTR) domain may help to break the immune system's self tolerance to MUC1, at least in human MUC1-expressing transgenic mice while unglycosylated human MUC1 VNTRs generated a weaker immune response. While not wishing to be bound by theory, it is now also believed that this is because the glycopeptide is possibly seen by the immune system as a more foreign epitope in comparison to the unglycosylated MUC1 which is more self-like.

Xenoantigens:

Many carbohydrate antigens are not highly immunogenic. One approach to increasing the immunogenicity of antigens is to target the antigens to antigen presenting cells (APCs). The effectiveness of vaccines can be increased by the incorporation of a xenoantigen. For example, the xenoantigen Galα1-3Galβ1 (αGal) can be used as an in vivo generated immune complex between the αGal epitopes and the natural antibodies (NA) against αGal in serum. The Fc portion on this immune complex is recognized by the Fcγ receptors on the APCs, thereby leading to the overall internalization of the antigen facilitating presentation by the major histocompatibility complex (MHC) on APCs. NA can also enhance uptake by APCs using other receptors such as complement receptors. Also, there are a variety of NAs that can bind antigens, including autoantigens, normally present in the blood.

The NAs, which can be of the IgM, IgG, or IgA isotype in humans, exhibit specific binding to a variety of different antigens, including proteins, DNA, numerous neutral and anionic phospholipids, carbohydrates, and a variety of other lipids, including neutral and anionic glyco-lipids, cholesterol, and squalene. For example, a large fraction of NAs-to-phospholipid is circulating in vivo as immune complexes to phospholipids. Thus, not only can the xenoantigens complex NAs, but also the lipids and phospholipids present in liposomes can complex NAs as well.

In addition, there are other, and highly abundant, anti-carbohydrate NAs in human serum. The most abundant NA detectable was specific for β-linked L-rhamnose (L-Rha) with the fourth most abundant being against α-linked L-Rha; for example:

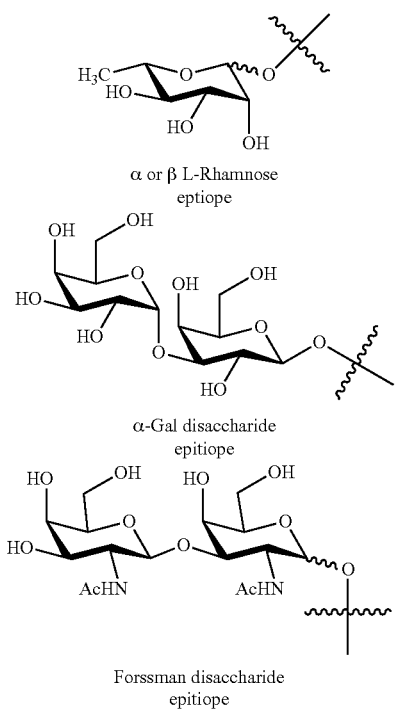

α or β L-Rhamnose epitope

α-Gal disaccharide epitope

Forssman disaccharide epitope

Antibodies against both α/β L-Rha are more prevalent than those against α-Gal.

In one aspect, there is described herein a method where the incorporation of α/β-linked L-Rha epitopes into vaccines (by direct conjugation or by non-covalent association with liposomal vaccine formulations) increases immunogenicity by NA-dependant antigen uptake mechanism.

In another aspect, there is described herein a vaccine composition that incorporates the non-covalent association of the L-Rha xenoantigen in a liposome with one or more other components of the vaccine composition that are independently embedded in the liposome. This incorporation eliminates the need to chemically synthesize a complex xenoantigen-antigen conjugate molecule. Thus, any lipidated antigen can be introduced into the vaccine composition. One non-limiting example is the L-Rha motif which binds anti-L-Rha NAs.

The Fc portion of the NA of an in vivo generated immune complex is recognized by the Fcγ receptors located on the surface of the APCs or by complement and complement receptors, thereby leading to the better internalization of the vaccine.

Also, the T-cell proliferation is enhanced when the antigen and xenoantigen are co-localized on a liposome in the presence of APCs and anti L-Rha antibodies.

In one embodiment described herein, the xenoantigen is conjugated to a lipid (such as cholesterol) by means of a linker (such as tetraethylene glycol (TEG)), which allows the xenoantigen to be displayed on the surface of the liposome along with the lipidated-tumor, bacterial or viral antigen.

In such embodiments, the linker between the xenoantigen and the cholesterol lipid allows for a xenoantigen-NA binding interaction.

Antigens:

For the development of a vaccine (e.g., an anti-cancer vaccine, an anti-viral vaccine, or an anti-bacterial vaccine), an antigen is required. Broadly, an antigen is defined as an entity or foreign molecule that, when introduced into the body, triggers the production of an antibody by the immune system. The term "antigen" also refers to any molecule or molecular fragment that can be bound by a major histocompatibility complex (MHC) and presented to a T-cell receptor.

Tumors of epithelial origin provide a variety of TACAs that can act as antigens by interacting with B-cell receptors. These include TACAs identified on the glycoproteins and glycolipids that decorate the cancer cells. Non-limiting examples of TACAs include: the TF, Tn, sialyl Tn (sTn) and sialyl Lewis a (sLe$^a$) antigens, whose structures are shown above. These structures as well as many other TACAs can produce a considerable humoral immune response.

In addition, peptides and glycopeptides can interact with B-cell receptors to produce antibodies.

One of the major disadvantages of using TACAs alone as cancer vaccines, however, is their weak immunogenicity. Generation of high amounts of high affinity IgG antibodies against the cancer antigen depends upon the combined interaction of the B-cells and the helper T-cells, and therefore requires the vaccine to contain a peptide epitope which can be displayed on the major histocompatibility complex (MHC) class-II or class-I molecules that are present on the surface of APCs, such as DCs. In general, TACAs alone cannot activate the helper T-cells, resulting in poor immunogenicity. Previous efforts to counteract this problem involved the conjugation of TACAs to large carrier proteins like keyhole limpet hemocyanin (KLH), bovine serum albumin (BSA), TLR agonists and zwitterionic polysaccharides. However, one drawback to the protein conjugation strategy is that the major immune response is towards the carrier protein, thus resulting in a suppressed immune response for the cancer antigen.

The protein conjugates provide the peptide sequences, which protein sequences can then be displayed as helper T-cell epitopes on MHC class-II molecules. The resulting complexes activate CD4$^+$ helper T-cells which then interact with antibody-producing B-cells allowing the B-cells to produce higher affinity antibodies.

For example, smaller 20-amino acid peptides which can bind MHC class-II can be conjugated to TACAs. These conjugates can produce high amounts of high affinity IgG anti-TACA antibodies. This strategy provides an advantage over the use of large carrier proteins as helper T-cell epitope, as the immune system can now focus more resources on the available TACA antigens rather than producing antibodies to the carrier protein.

In one aspect, the use of peptide sequences acts as an "autologous helper T-cell epitope." Such autologous helper T-cell epitopes can be sequences expressed on the tumor. The use of foreign carrier proteins and peptides as conjugates thus provide helper-T cell epitopes unrelated to the tumor, and thus act as "heterologous helper T-cell epitopes."

One non-limiting example of an autologous helper T-epitope is the MUC1 VNTR consisting of the 20 amino acid sequence PDTRPAPGST(Tn)APPAHGVTSA [SEQ ID NO: 1]. In a particular example, the threonine in the sequence GST is synthetically modified to incorporate the α-GalNAc-O-Thr (Tn) TACA. This region in the MUC1 sequence is a more potent candidate for generating high antibody titers against Tn than the unglycosylated MUC1 VNTR.

Lipid Attachment to Antigen

Glycopeptides formed by the conjugation of B-cell epitopes and helper T-cell epitopes often show moderate immunogenicity. A major reason for such moderate immunogenicity is the inappropriate maturation of the DCs.

Described herein is a method which overcomes this problem, where a lipid component is incorporated into a vaccine capable of imparting self adjuvanating properties. Toll-like receptor (TLR) agonists interact with TLRs to facilitate the maturation of dendritic cells. The maturation of the dendritic cells can be achieved by the involvement of a variety of TLR subclasses, as for example: TLR1, TLR2, TLR3, TLR4, TLR5, TLR6, TLR7, TLR8, TLR9, TLR10, TLR11, TLR12, TLR13, TLR14, TLR15 and TLR16.

Non-limiting examples of TLR2 interactive lipopeptides include: dipalmitoyl-S-glyceryl-cys-(Pam$_2$Cys); tripalmitoyl-S-glyceryl-cys-(Pam$_3$Cys-); dipalmitoyl-S-glyceryl-cys-ser-lys-lys-lys-lys (Pam$_2$Cys-Ser-(Lys)$_4$) [SEQ ID NO: 2], tripalmitoyl-S-glyceryl-cys-ser-lys-lys-lys-lys (Pam$_3$Cys-Ser-(Lys)$_4$) [SEQ ID NO: 3], and MALP-2 dipalmitoyl-S-glyceryl-cys-gly-asn-asn-asp-glu-ser-asn-ile-ser-phe-lys-glu-lys (Pam$_2$CGNNDESNISFKEK)] [SEQ ID NO: 4].

Non-limiting examples of palmitoylated lipids [SEQ ID NOS: 3, 2 and 4], respectively, in order of appearance, that may interact with TLR2 thus include:

Pam$_2$Cys-Ser-(Lys)$_4$ [SEQ ID NO:2], for example, acts as TLR2/TLR6 agonists, while Pam$_3$Cys-Ser-(Lys)$_4$ [SEQ ID NO:3] acts as a TLR2/1 agonist. Lipopeptide MALP-2 acts a TLR2/6 ligand. Tripalmitoyl-S-glyceryl-cys (Pam$_3$Cys), and dipalmitoyl-S-glyceryl-cys (Pam$_2$Cys), are minimal structural epitopes common to palmitoylated TLR2 ligands.

Synthesis of Two-Component Vaccine

Lipid Components

In certain embodiments, the lipid component of a vaccine composition serves three purposes: first, the lipid component acts as a vaccine adjuvant capable of interacting with Toll-Like receptors; second, the lipid component facilitates the formulation of the glycolipopeptide into liposomes anchoring the glycopeptide epitope to the inner and outer surfaces of the liposomes; and third, the lipidation facilitates cross-presentation of peptide antigens by APCs.

Xenoantigen Component

Another aspect is the ability to bind natural antibodies (NAs) specific for a desired target epitope (e.g., the xenoantigen L-Rha epitope). The bound NAs thus facilitate the opsonization of the liposomal vaccine by APCs. Covalent attachment of xenoantigens to lipids through the use of a suitable linker thus facilitates the incorporation of these epitopes into the liposomes.

Linker Components

In some embodiments, the xenoantigen is covalently attached to a lipid through the use of a suitable linker. Further, in particular embodiments, the length of the linker between the xenoantigen and lipid can be optimized to achieve a desired xenoantigen-NA interaction. The conjugation of a lipid to the xenoantigen allows for the display of

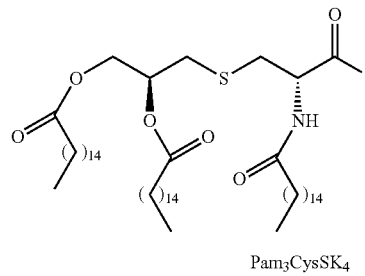

Pam$_3$CysSK$_4$

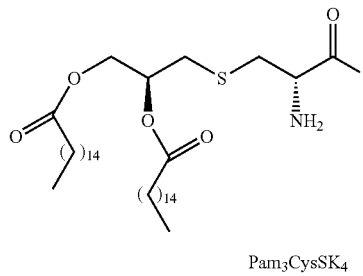

Pam$_3$CysSK$_4$

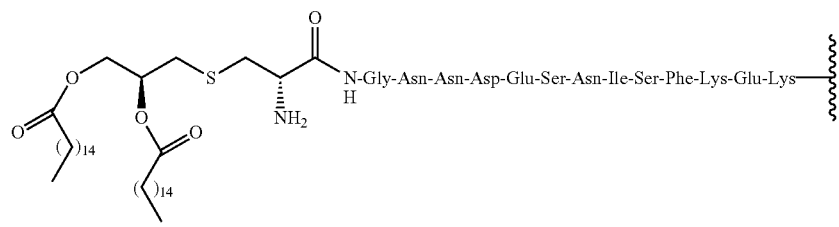

MALP-2

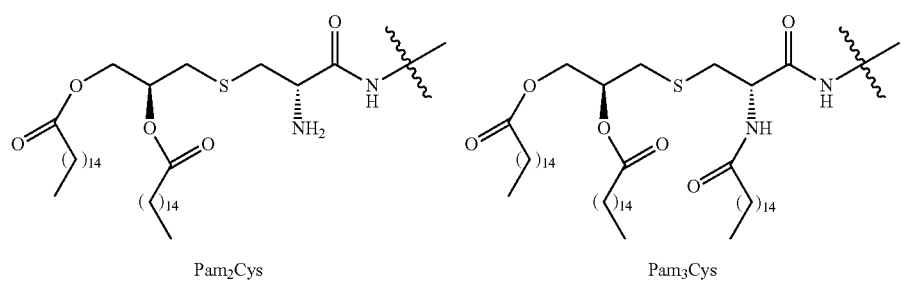

Pam$_2$Cys          Pam$_3$Cys multiple xenoantigens on the surface of the liposomes, thereby facilitating multivalent NA-antibody binding to the liposome.

The Fc portion of the NA in the in vivo generated immune complex is thus recognized by the Fcγ receptors on APCs, thereby leading to opsonization of the vaccine by APCs.

Vaccine Compositions

In certain embodiments, the composition of the vaccine contains non-covalently associated components: i) a lipid-linked antigen; ii) a composition of lipids capable of forming liposomes; iii) a lipid-linked xenoantigen; and, optionally, iv) one or more independent adjuvant molecules. These components form a well defined liposomal vaccine composition I, as shown in FIG. 2. The lipid-linked antigen is comprised of an antigen linked to a first lipid (also called lipid$_a$ herein). In certain embodiments, the antigen can be a peptide or glycopeptide of 1 to 100 amino acids in length. The antigen may also include a B-cell epitope conjugated to a peptide or glycopeptide sequence that is capable of providing a T-cell epitope. The peptide, glycopeptide, peptide-B-cell, or glycopeptides-B-cell epitope conjugate is linked to lipid$_a$.

The generalized composition of the lipid$_a$-linked antigen component is the structure of composition II, shown in FIG. 3.

peptides having the 20 amino acid sequence TSAPDT(Tn) RPAPGSTAPPAHGV [SEQ ID NO: 6]. The T(Tn) in the sequence is the α-GalNAc-O-T (Tn) TACA.

The linker$_a$ component can be: a chain of $C_{2-n}$ alkyl, dialkyl-substituted aryl $C_{1-n}$ alkyl, dialkyl-substituted heteroaryl $C_{1-n}$ alkyl, or $—CH_2CH_2(OCH_2CH_2)_n—$, where n is a positive integer. In one embodiment, the linker$_a$ component comprises a dialkyl-substituted heteroaryl $C_{1-n}$ alkyl of formula III, as shown in FIG. 4. In certain embodiments, the lipid$_a$ portion of the formula III contains a lipid of one of the following structures: $Pam_2Cys$-Ser-$(Lys)_4$, $Pam_3Cys$-Ser-$(Lys)_4$, MALP-2, $Pam_3Cys$, or $Pam_2Cys$. In particular embodiments, the first lipid (lipid$_a$) component of the formula III can contain a lipid having the structure $Pam_3Cys$, or the structure $Pam_2Cys$.

Synthesis of Toll-Receptor Ligands

Another aspect is the synthesis of a composition IV (shown in FIG. 5) which, when reacted with an appropriate catalyst in the presence of a modified peptide antigen of composition V, forms a composition of composition II.

In certain embodiments, the lipid$_a$ moiety of the composition IV can be a structure of the Formulae [SEQ ID NOS: 3, 2 and 4], respectively, in order of appearance:

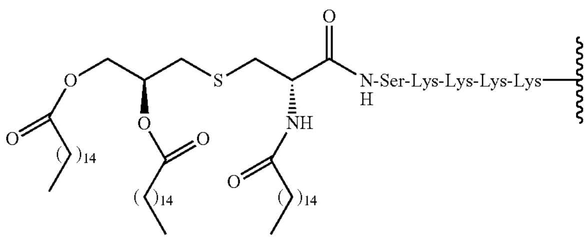

$Pam_3CysSK_4$ 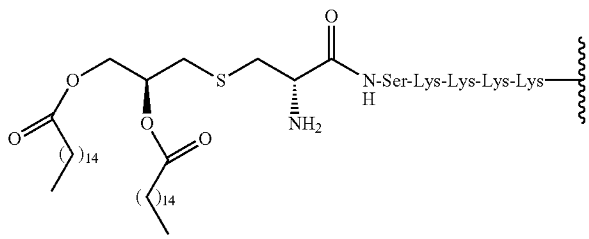 $Pam_3CysSK_4$

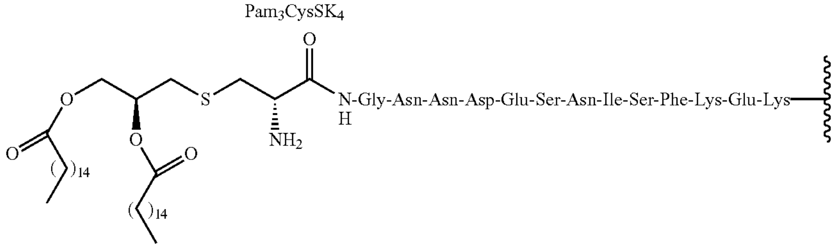

MALP-2

$Pam_2Cys$ 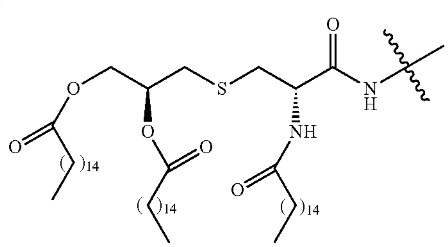 $Pam_3Cys$

In one embodiment, the antigen contains a glycopeptide having the 20 amino acid sequence PDTRPAPGST(Tn) APPAHGVTSA [SEQ ID NO:1]. The T(Tn) in the sequence is the α-GalNAc-O-T (Tn) TACA. In another embodiment, the antigen contains a glycopeptide having the 20 amino acid sequence TSAPDTRPAPGSTAPPAHGV [SEQ ID NO: 5]. In another embodiment, the antigen contains a glyco- Referring again to FIG. 5 and the composition V, the "A" group therein represents a linker. In certain embodiments, the linker can be comprised of: a chain of $C_{1-n}$ alkyl, dialkyl substituted aryl $C_{1-n}$ alkyl, or $—CH_2CH_2(OCH_2CH_2)_n—$; n is a positive integer. In a particular embodiment, A comprises a $C_{1-5}$ alkyl chain.

Further, in composition V, the antigen moiety can be a peptide or glycopeptide that is covalently bonded at the N-terminus to a carbonyl group on the linker, thus forming an amide bond. In a particular embodiment, the antigen contains a glycopeptide having a 20 amino acid sequence PDTRPAPGST(Tn)APPAHGVTSA [SEQ ID NO:1], where the T(Tn) in the sequence GSTA is the α-GalNAc-O-Thr TACA. In another embodiment, the antigen contains a glycopeptide having the 20 amino acid sequence TSAP-DTRPAPGSTAPPAHGV [SEQ ID NO: 5]. In another embodiment, the antigen contains a glycopeptide having the 20 amino acid sequence TSAPDT(Tn)RPAPG-STAPPAHGV [SEQ ID NO: 6]. The T(Tn) in the sequence is the α-GalNAc-O-T (Tn) TACA.

Figure 6:
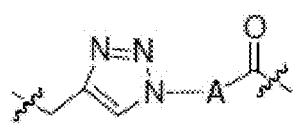
FIG. 6: Schematic illustration of a $linker_a$ component.

Upon reaction of composition IV with composition V in the presence of an appropriate catalyst, a composition II is formed. In certain embodiments, the linker$_a$ moiety can be a dialkyl-substituted heteroaryl $C_{1-n}$ alkyl of formula VI, as shown in FIG. 6.

In formula VI, the "A" group can be a linker comprised of: a chain of $C_{1-n}$ alkyl, dialkyl substituted aryl $C_{1-n}$ alkyl, or —$CH_2CH_2(OCH_2CH_2)_n$—; n is a positive integer. In a particular embodiment, the "A" group comprises a $C_{1-5}$ alkyl chain.

Figure 7:
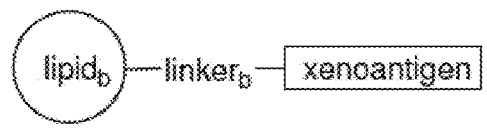
FIG. 7: Schematic illustration of a lipid-linked xenoantigen component.

Referring now to FIG. 7, the lipid-linked xenoantigen can be a xenoantigen linked to a lipid. The xenoantigen can be any structure which binds NAs. The xenoantigen is linked to a second lipid (lipid$_b$) through a second linker (linker$_b$). The generalized composition of the lipid-linked xenoantigen component is structure of composition VII as shown in FIG. 7.

In one embodiment, the xenoantigen contains a structure comprised of: alpha- or beta-linked L-rhamnose, a beta-linked alpha-gal epitope, or an alpha- or beta-linked Forssmann disaccharide epitope. In a particular embodiment, the xenoantigen contains a structure consisting of alpha- or beta-linked L-rhamnose.

Figure 8:
FIG. 8: TEG composition used in a $linker_b$ component.

The linker$_b$ component can be comprised of: a chain of $C_{1-n}$ alkyl, dialkyl substituted aryl $C_{1-n}$ alkyl, or —$CH_2CH_2$ $(OCH_2CH_2)_n$—; where n is a positive integer. In a particular embodiment, the linker$_b$ component has a tetraethyleneglycol (TEG) of formula VIII, as shown in FIG. 8.

Figure 9:
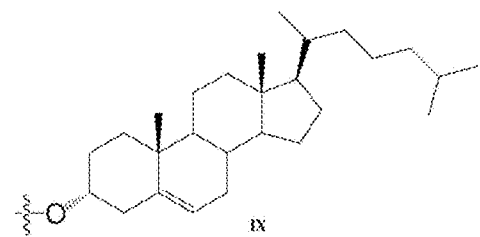
FIG. 9: Schematic illustration of a structure contained in a $lipid_b$ portion of a lipid-linked xenoantigen component.

In a particular embodiment, the lipid$_b$ portion can contain a structure of the formula IX, as shown in FIG. 9. In one particular embodiment, the liposomal forming lipids can be comprised of 1,2-dipalmitoyl-sn-glycero-3-phosphocholine (DPPC) and cholesterol in a ratio of from about 80:20 to about 70:30, respectively.

It is to be understood that, in certain embodiments, an immunologic adjuvant may or may not be included as part of the composition of the vaccine. For example, in certain embodiments, the immunologic adjuvants may be, but are not limited to: a saponin (e.g., QS21), monophosphoryl lipid A, 3'-O-deacylated monophosphoryl lipid A, or interleukin 12.

Pharmaceutical Preparations

Pharmaceutical compositions of the present invention comprise an effective amount of a compound(s) or composition(s) disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, general safety and purity standards as required by FDA Office of Biological Standards.

A vaccine composition disclosed herein may comprise different types of carriers depending on whether it is to be administered in solid, liquid or aerosol form, and whether it need to be sterile for such routes of administration as injection. Vaccine compositions disclosed herein can be administered intravenously, intradermally, transdermally, intrathecally, intraarterially, intraperitoneally, intranasally, intravaginally, intrarectally, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a vaccine composition herein and/or additional agents is formulated to be administered via an alimentary route Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, or they may be compressed into tablets, or they may be incorporated directly with the food of the diet.

In further embodiments, a vaccine composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the vaccine compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the vaccine compositions in the required amount in the appropriate solvent with various of the other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the vaccine compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the vaccine compositions formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the vaccine composition and provide for a homogenous mixture. Transdermal administration of the vaccine compositions may also comprise the use of a "patch." For example, the patch may supply one or more vaccine compositions at a predetermined rate and in a continuous manner over a fixed period of time.

In certain embodiments, the vaccine compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the vaccine compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the vaccine compositions described herein.

It is further envisioned the vaccine compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain embodiments of the invention and should not be interpreted to limit the scope of the invention as defined in the claims, unless so specified.

General Methods

All fine chemicals such as L-rhamnose, cholesterol, p-toluene sulfonyl chloride, copper sulfate, etc., and anhydrous solvents, such as anhydrous methanol, were purchased from Acros Organics. 1,2-dipalmitoyl-sn-glycero-3-phosphocholine (DPPC) was obtained from Avanti Polar Lipids Inc. (Alabaster, Ala.). Boron trifluoride etherate was obtained from Aldrich. The chemicals were used without further purification. All solvents were obtained from Fisher and used as received except dichloromethane, which was dried and distilled following the standard procedures. Silica (230-400 mesh) for flash column chromatography was obtained from Sorbent Technologies; thin-layer chromatography (TLC) precoated plates were from EMD. TLCs (silica gel 60, $f_{254}$) were visualized under UV light or by charring (5% $H_2SO_4$-MeOH). Flash column chromatography was performed on silica gel (230-400 mesh) using solvents as received.

$^1$H NMR was recorded either on a Varian VXRS 400 MHz or an INOVA 600 MHz spectrometer in $CDCl_3$ or $CD_3OD$ using residual $CHCl_3$ and $CHD_2OH$ as internal references, respectively.

$^{13}$C NMR was recorded on a Varian VXRS 100 MHz or an INOVA 150 MHz in $CDCl_3$ using the triplet centered at δ 77.23 or $CD_3OD$ using the septet centered at δ 49.0 as internal reference. High resolution mass spectrometry (HRMS) was performed on a TOF mass spectrometer. The peptide was synthesized on a Omega 396 synthesizer (Advanced ChemTech, Louisville, Ky.). Tris [(1-benzyl-1H-1, 2,3-triazol-4-yl)methyl] amine (TBTA), preloaded Fmoc-L-Ala-Wang resin and all other Fmoc-L-amino acids were procured from Anaspec (San Jose, Calif.). FITC goat anti-mouse IgG/IgM and purified mouse anti-human CD227 (anti-human MUC1) were obtained from BD-biosciences (San Jose, Calif.). Scanning electron microscope imaging was done on a JEOL JSM-7500F field scanning electron microscope. Dynamic light scattering measurements was done DynaPro Titan temperature controlled microsampler (Wyatt Technology Corporation). Fluorescence microscopy was done on a Nikon TiU microscope.

Example 1

Synthesis of L-Rhamnose-TEG-Cholesterol (3)

Figure 10:
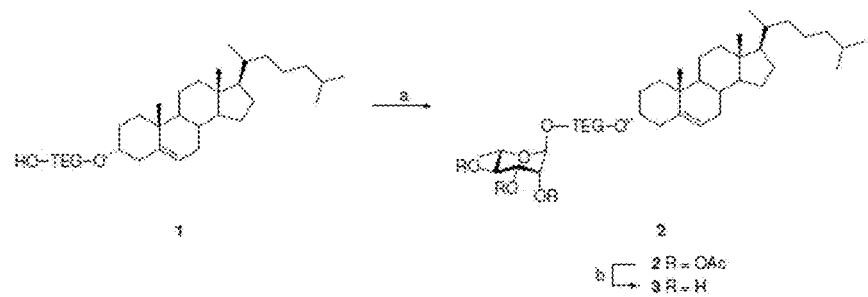
FIG. 10: Scheme 1: Schematic illustration of synthesis of a L-Rhamnose-TEG-Cholesterol (3).

Cholesterol tetraethylene glycol (1) was glycosylated with peracetyl L-rhamnose in presence of boron trifluoride etherate to afford peracetyl rhamnose-TEG-cholesterol (2) (32%) which was deacetylated under Zémplen conditions to generate L-rhamnose-TEG-cholesterol (3) (85%). See FIG. 10, illustrating Scheme 1. Compound (3) anchors the Rha epitopes on the surface of the liposomes thereby facilitating anti-Rha antibody binding.

(5-Cholesten-3α-yloxy)-3n$^3_9$-trixaundecanyl-2,3,4-tri-O-acetyl-α-L-Rhamnopyranoside (2)

To a solution of 1,2,3,4-tetra-O-acetyl rhamnopyranose (0.64 g, 1.92 mmol) in $CH_2Cl_2$ (3 mL) was added (5-cholesten-3α-yloxy)-3n$^3_9$-trixaundecan-1-ol (1) (1.30 g, 2.30 mmol) in $CH_2Cl_2$ and the mixture was cooled to 0° C. $BF_3.OEt_2$ (486 mL, 3.84 mmol) was added dropwise to the reaction mixture and the resulting solution was stirred at ambient temperature under $N_2$ atmosphere. The reaction was monitored by TLC (EtOAc:hexanes=1:1) and appeared complete after 18 h. The reaction mixture was diluted with $CH_2Cl_2$ (25 mL) and washed with saturated $NaHCO_3$ (25 mL), water (25 mL) and brine (25 mL) after which the organic layer was dried over anhydrous $Na_2SO_4$. Excess solvent was evaporated under reduced pressure and the residue was purified by silica gel flash column chromatography using 30% EtOAc in hexanes as solvent to afford (2) as a light yellow solid (0.51 g, 32%). $^1$H NMR (600 MHz, $CDCl_3$): δ 0.67 (s, 3H, cholesterol), 0.85-1.15 (23H, cholesterol), 1.21 (d, 3H, J=6 Hz, C-5 $CH_3$), 1.24-1.52 (12H, cholesterol), 1.80-1.95 (5H, cholesterol), 1.98 (s, 3H, $COCH_3$), 2.05 (s, 3H, $COCH_3$), 2.15 (s, 3H, $COCH_3$), 3.17 (m, 1H, —OCH-cholesterol), 3.63-3.66 (16H, —$CH_2$—$CH_2O$-TEG), 3.92 (m, 1H, H-5), 4.77 (d, 1H, J=1.8 Hz, H-1), 5.06 (t, 1H, J=10.2 Hz, H-4), 5.26 (dd, 1H, J=1.8, 3.6 Hz, H-2), 5.30 (dd, 1H, J=4.2, 9.9 Hz, H-3), 5.33 (m, 1H, —C=CH-cholesterol). $^{13}$C NMR (100.56 MHz, $CDCl_3$): δ 12.04, 17.61, 18.90, 19.58, 20.95, 21.03, 21.14, 21.25, 22.76, 23.02, 24.01, 24.48, 28.21, 28.43, 28.53, 29.90, 32.07, 32.13, 35.97, 36.37, 37.07, 37.42, 39.23, 39.70, 39.96, 42.50, 50.36, 53.63, 56.32, 56.96, 66.46, 67.30, 67.46, 69.30, 70.03, 70.24, 71.35, 79.68, 97.74 (C-1), 121.74 (C=C), 141.15 (C=C), 170.18 ($COCH_3$), 170.25 ($COCH_3$), 170.32 ($COCH_3$). HRMS [M+Na] m/z: calcd for $C_{47}H_{78}NaO_{12}$, 857.5391; found, 857.5396.

(5-Cholesten-3α-yloxy)-3n$^3_9$-trixaundecanyl Rhamnopyranoside (3)

To a solution of (2) (0.45 g, 0.54 mmol) in MeOH (10 mL) was added metallic sodium (0.03 g) and the resulting solution was stirred at ambient temperature under $N_2$ atmosphere. The reaction was monitored by TLC (5% MeOH in $CH_2Cl_2$) and appeared complete after 1 h. The solution was neutralized by Amberlite H$^+$ exchange resin. Excess solvent was evaporated under reduced pressure and the residue was purified by silica gel flash column chromatography using 5% MeOH in CH$_2$Cl$_2$ as solvent to afford (3) as a yellowish white solid (0.32 g, 85%). $^1$H NMR (600 MHz, CDCl$_3$): δ 0.68 (s, 3H, cholesterol), 0.86-1.25 (24H, cholesterol), 1.32 (d, 3H, J=6 Hz, C-5 CH$_3$), 1.44-1.53 (16H, cholesterol), 2.83 (s, 1H, C-4 OH), 3.08 (d, 1H, J=3 Hz, H-1), 3.20 (m, 1H, —O—CH-cholesterol), 3.43 (t, 1H, J=9.6 Hz, H-4), 3.62-3.71 (16H, —CH$_2$—CH$_2$O-TEG), 3.73 (m, 1H, H-5), 3.83 (dd, 1H, J=3, 6.9 Hz, H-3), 3.98 (s, 1H, H-2), 4.87 (s, 1H, C-2 OH), 5.31 (s, 1H, C-3 OH), 5.35 (m, 1H, —C=CH-cholesterol). $^{13}$C NMR (100.56 MHz, CDCl$_3$): δ 12.07, 17.83, 18.92, 19.60, 21.27, 22.78, 23.04, 24.03, 24.50, 28.23, 28.44 (2), 32.08, 32.15, 35.99, 36.39, 37.06, 37.39, 39.09, 39.73, 39.97, 42.53, 50.36, 56.34, 56.97, 66.74, 67.32, 68.07, 70.48, 70.63, 70.75, 70.81, 70.93, 70.97, 71.05, 71.80, 73.81, 79.87, 99.98 (C-1), 121.96 (C=C-cholesterol), 140.98 (C=C-cholesterol). HRMS [M+Na] m/z: calcd for C$_{41}$H$_{72}$NaO$_9$, 731.5074; found, 731.5090.

Example 2

Synthesis of Alkyne Functionalized Pam$_3$Cys (6)

Figure 11:
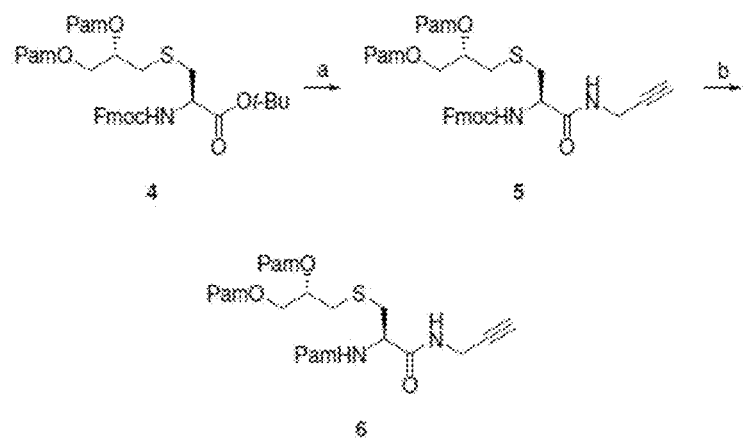
FIG. 11: Scheme 2: Schematic illustration of synthesis of an alkyne functionalized $Pam_3Cys$ composition (6).

O-palmitoylated Fmoc L-cystine tert-butyl ester (4) was deprotected by a brief treatment with trifluoroacetic acid (TFA). The free acid was coupled with propargyl amine in the presence of benzotriazol-1-yl-oxytripyrrolidinophosphonium hexafluorophosphate (PyBOP), 1-hydroxy-benzotriazole (HOBt) and N,N-diisopropylethylamine (DIPEA) to yield (5) (66% over 2 steps). Fmoc group in compound (5) was removed by treatment with a mixture of acetonitrile-dichloromethane-diethyl amine (2:1:2) followed by subsequent palmitoylation by coupling with palmitic acid, PyBOP, HOBt and DIPEA to afford our target alkyne functionalized Pam$_3$Cys amide derivative (6) (80% over 2 steps), as shown in FIG. 11, Scheme 2. Compound (6), which is a TLR-2 agonist, serves the purpose of an immunoadjuvant for a vaccine, and also anchors the MUC1-Tn conjugate on the surface of the liposome.

N-propargyl Pam$_2$FmocCys Amide Derivative (5)

Pam$_2$FmocCys tertiary butyl ester (0.30 g, 0.32 mmol) was dissolved in minimum volume of neat TFA (1 mL) and stirred at ambient temperature under N$_2$ atmosphere. TLC (EtOAc:hexanes=1:4) indicated the completion of the reaction after 1 h. The reaction mixture was evaporated to dryness under vacuum and the residue was dissolved in CH$_2$Cl$_2$ (3 mL). PyBOP (198 m g, 0.38 mmol), HOBt (58 mg, 0.38 mmol), DIPEA (78 μL, 0.47 mmol) and 4 Å mol. sieves (2-3 beads) were added sequentially and the mixture was stirred for 5 minutes at room temperature followed by the addition of propargyl amine (25 μL, 0.38 mmol) and stirred at ambient temperatures under N$_2$ atmosphere. The reaction was monitored by TLC (EtOAc:hexanes=1:4) and appeared complete after 4 h. The reaction mixture was filtered, washed with phosphate buffer (10 mL) and extracted with CH$_2$Cl$_2$ (3×10 mL). The organic layer was dried over anhydrous Na$_2$SO$_4$ and concentrated. The residue was purified by silica gel flash column chromatography using EtAc-hexanes (1:4) as solvent to afford (5) as a white solid (192 mg, 66%). $^1$H NMR (600 MHz, CDCl$_3$): δ 0.87 (t, 6H, J=7.2 Hz, Pam-CH$_3$), 1.14-1.65 (m, 52H, Pam-CH$_2$), 1.68 (s, 1H, alkyne-CH), 2.18-2.35 (m, 4H, COCH$_2$), 2.83 (m, 1H, Cys-CHH), 2.89 (dd, 1H, J=7.2, 14.4 Hz, S-glyc-eryl-OCHH), 3.01 (dd, 1H, J=6, 14.4 Hz, cys-CHH), 4.06 (dd, 1H, J=3, 4.8 Hz, S-glycerylO-CHH), 4.08 (s, 2H, CO—NH—CH2), 4.18 (dd, 1H, J=6, 11.4 Hz, S-glyceryl-O—CHH), 4.23 (t, 1H, J=7.2 Hz, Fmoc-CH), 4.39 (m, 1H, NH—CH—CO), 4.42 (m, 2H, Fmoc-CH2), 5.12 (m, 1H, S-glyceryl-O—CH), 5.73 (d, 1H, J=7.8 Hz, Pam-NH), 6.89 (s, 1H, CO—NHCH2), 7.31-7.81 (m, 8H, Fmoc-ArH). $^{13}$C NMR (150.84 MHz, CDCl3): δ 14.35-36.70 (30C, Pam-C), 47.29 (2), 53.32, 63.58, 67.48, 70.61, 71.78, 72.07, 79.09, 79.85, 120.22, 125.30, 127.30 (2), 127.97 (2) 141.49, 141.50, 143.85, 143.89 (Aromatic-C), 170.07, 173.66 (2), 174.04 (Cys-CO). HRMS [M+Na] m/z: calcd for C$_{56}$H$_{86}$N$_2$NaO$_7$S, 953.6053. found, 953.6073.

N-propargyl Pam$_3$Cys Amide Derivative (6)

Composition (5) (192 mg, 0.21 mmol) was dissolved in a mixture of CH$_3$CN—CH$_2$Cl$_2$-Et$_2$NH (2:1:2, 2.50 mL) and stirred at ambient temperature under N$_2$ atmosphere. TLC (EtOAc:hexanes=1:4) indicated the complete deprotection of the Fmoc group after 2 h. The reaction mixture was evaporated to dryness under vacuum. Palmitic acid (64 mg, 0.25 mmol), PyBOP (128 mg, 0.25 mmol), HOBt (38 mg, 0.25 mmol) were dissolved in CH$_2$Cl$_2$ (3 mL) followed by the addition of DIPEA (51 μL, 0.31 mmol). The mixture was stirred for 5 minutes and added to the residue of the Fmoc deprotected product from compound (5) containing 4 Å mol. sieves (2-3 beads). The reaction mixture was stirred at ambient temperature under N$_2$ atmosphere. The reaction was monitored by TLC (EtOAc:hexanes=1:4) and appeared complete after 4 h. The reaction mixture was diluted with CH$_2$Cl$_2$ (15 mL), filtered and evaporated to dryness. The residue was purified by silica gel flash column chromatography using EtOAC-hexanes (1:4) as solvent to afford (6) as a pale yellow solid (156 mg, 80%). $^1$H NMR (600 MHz, CDCl$_3$): δ 0.88 (t, 12H, J=6.6 Hz, Pam-CH$_3$), 1.10-1.63 (m, 78H, Pam-CH$_2$), 2.23 (s, 1H, Alkyne-CH), 2.24-2.36 (m, 6H, COCH$_2$), 2.71 (dd, 1H, J=7.8, 14.4 Hz, Cys-CHH), 2.86 (m, 6H, COCH$_2$), 2.95 (dd, 1H, J=6, 14 Hz, Cys-CHH), 4.06 (m, 2H, CO—NH—CH$_2$), 4.18 (dd, 1H, J=6.6, 12 Hz, S-glyceryl-O—CHH), 4.40 (dd, 1H, J=3, 12 Hz, S-glyceryl-O—CHH), 4.64 (q, 1H, J=6 Hz, NH—CH—CO), 5.12 (m, 1H, Sflyceryl-OCH), 6.64 (d, 1H, J=8.4 Hz, Pam-NH), 7.02 (t, 1H, J=5.4 Hz, CO—NH—CH$_2$). $^{13}$C NMR (150.84 MHz, CDCl$_3$): δ 14.35-42.19 (48C, Pam-C, Cys-C$_R$, S-glyceryl-C, NH—C), 51.30 (Cys-Ca), 63.65, 70.61, 71.98, 79.08, 170.40 (Cys-CO), 173.70, 173.86, 174.06 (Pam-CO). HRMS [M+Na] m/z: calcd for C$_{57}$H$_{106}$N$_2$NaO$_6$S, 969.7669. found, 969.7682.

Example 3

Synthesis of Pam$_3$Cys-MUC-1 VNTR-TACA Conjugate (9)

Figure 12:
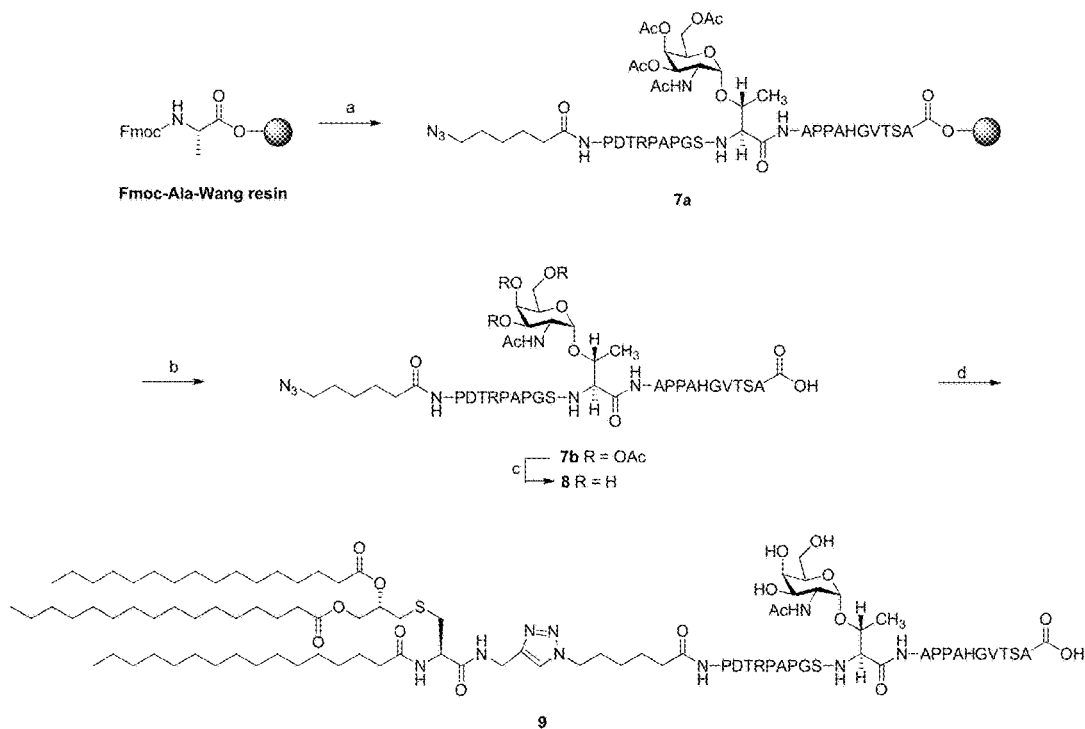
FIG. 12: Scheme 3: Schematic illustration of synthesis of a $Pam_3Cys$-MUC-1 VNTR-TACA conjugate (9) [SEQ ID NOS: 8, 9 and 7], respectively, in order of appearance.

A 20-amino acid tandem repeat of MUC1 which included the GS(α-GalNAc-O-T)A epitope was synthesized. The glycopeptide was modified with a terminal azido group in order to make a 'click' conjugation to the Pam$_3$Cys alkyne. The glycopeptide azide was synthesized by Fmoc strategy on an Omega 396 synthesizer (Advanced ChemTech, Louisville, Ky.) starting from preloaded Fmoc-L-Ala Wang resin using solid-phase chemistry, as shown in FIG. 12, Scheme 3.

The peptide synthesis was performed by coupling amino acid esters of HOBt using DIC as the coupling agent. A six-fold excess of N$^α$-Fmoc amino acid esters of HOBt in NMP were used in the synthesis. A 1:1 ratio of amino acid to DIC was used in all the coupling reactions. Deprotection of $N^\alpha$-Fmoc group was accomplished by treatment with piperidine in DMF. After the synthesis was complete, the peptide was cleaved from the solid support and deprotected using a modified reagent K cocktail consisting of TFA-thioanisole-ethanedithiol-water-phenol (88:3:5:2:2). The cocktail mixture was filtered through a Quick Snap column, purified by C18 reverse phase HPLC and lyophilized to afford composition (7b).

The acetyl groups in composition (7b) were deprotected by treatment with 6 mmol sodium methoxide in methanol. The product was purified by Bio-Gel (P-2, fine 45-90 µm) size exclusion chromatography using deionized water as solvent. Lyophilization of the fractions afforded composition (8) (100%) as a white powder.

Conjugation of the composition (8) (1 eqv) with the composition (6) (3 eqv) in the presence of copper sulfate pentahydrate (12 eqv), Tris [(1-benzyl-1H-1,2,3-triazol-4-yl)methyl] amine (TBTA) (12 eqv) and sodium ascorbate (12 eqv) in $H_2O$-MeOH-THF (1:1:2) as solvent at ambient temperatures thus afforded the target, $Pam_3Cys$-MUC1 VNTR-TACA conjugate (9), after 40 h.

Composition (9) was purified by LH20 using MeOH-dichloromethane (1:1) as solvent. The eleutants were lyophilized to afford composition (9) as a white solid (100%).

Synthesis of Azide (7b)

The glycopeptide azide was synthesized by Fmoc strategy on an Omega 396 synthesizer (Advanced ChemTech, Louisville, Ky.) using solid phase chemistry. The peptide synthesis was performed by coupling amino acid esters of HOBt using DIC as the coupling agent starting with a preloaded Fmoc-alanyl-Wang resin. A six-fold excess of $N^\alpha$-Fmoc amino acid esters of HOBt in NMP were used in the synthesis. A 1:1 ratio of amino acid to DIC was used in all the coupling reactions. Deprotection of $N^\alpha$-Fmoc group was accomplished by treatment with 25% piperidine in dimethylformamide twice; first for 5 minutes and then a second time for 25 minutes to afford composition (7a).

After the synthesis was complete, the peptide was cleaved from the solid support and deprotected using a modified reagent K cocktail consisting of 88% TFA, 3% thioanisole, 5% ethanedithiol, 2% water and 2% phenol. 4 mL of cleavage cocktail was added to the dried peptide-resin in a 15 mL glass vial blanketed with nitrogen. Cleavage was carried out for 2.5 hrs with gentle magnetic stirring. At the end cleavage time, the cocktail mixture was filtered on a Quick-Snap column. The filtrate was collected in 20 mL ice-cold butane ether. The peptide was allowed to precipitate for an hour at −200° C., centrifuged, and washed twice with ice-cold methyl-t-butyl ether. The precipitate was dissolved in 25% acetonitrile and lyophilized to complete dry powder affording composition (7b). Quality of peptides was analyzed by analytical reverse phase HPLC and MALDI-TOF (matrix assisted laser desorption ionization time-of-flight) mass spectrometer, model 4800 from Applied Biosystems. HR-MALDI-MS: [M+H] m/z calcd for $C_{100}H_{155}N_{29}O_{37}$, 2355.1172. found, 2355.1753.

Synthesis of Azide (8)

Composition (7b) (5 mg, 2.24 µmol) was dissolved in 2 mL of dry methanol and 12 µL of freshly prepared 1 M sodium methoxide was added and the reaction mixture was stirred at ambient temperature under $N_2$ atmosphere for 2 h. The reaction mixture was neutralized with solid carbon dioxide. The reaction mixture was concentrated and purified by Bio-Gel (P-2, fine 45-90 µm) size exclusion chromatography using deionized water as solvent. Lyophilization of the eleutants afforded composition (8) as a white powder (4.7 mg, 100%). HR-MALDI-MS: [M+H] m/z calcd for $C_{94}H_{149}N_{29}O_{34}$, 2229.0895. found 2229.0959.

Synthesis of Glycolipopeptide (9)

$CuSO4.5H_2O$ (134 µg, 0.54 µmol) and TBTA (2.14 mg, 4.04 µmol) were dissolved in $H_2O$-THF (1:1, 0.40 mL) and to it Na-ascorbate (0.80 mg, 4.04 µmol) was added and stirred for 5 minutes. Composition (6) (1.27 mg, 1.35 µmol) in THF (0.40 mL) was added to the reaction mixture and stirred for 15 minutes followed by the addition of a solution of composition (8) (1 mg, 0.45 µmol) in $H_2O$-MeOH (1:3, 0.4 mL). The reaction mixture was stirred at ambient temperature under $N_2$ atmosphere for 40 h. The reaction mixture was concentrated, dissolved in $CH_2Cl_2$-MeOH (1:1) and purified by a short LH 20 size exclusion column using $CH_2Cl_2$-MeOH (1:1) as solvent. Lyophilization of the eleutants afforded composition (9) as a white solid (1.9 mg, 100%). HR-MALDI-MS: [M+H] m/z calcd for $C_{151}H_{255}N_{31}O_{40}S$, 3175.593. found 3175.425. A mass peak corresponding to a protonated methyl ester of the product was also observed.

Example 4

Synthesis of a Liposomal Vaccine of Composition I and Control Compositions

The liposomes were formulated by the extrusion method in a total lipid concentration of 30 mM. For the preparation of the liposomes, 1,2-dipalmitoyl-sn-glycero-3-phosphocholine (DPPC) was used. Lipid stock solutions were prepared by dissolving each lipid into chloroform inside glass vials. Aliquots of the stock solutions were mixed in proportions in another small glass vial to give a solution with a total lipid concentration of 30 mM in a total volume of 2 mL.

Batch 1: DPPC 80%, Cholesterol 10%, Rha-cholesterol 10% and $Pam_3cys$-MUC1-Tn (9) 2 nM.

Batch 2: DPPC 80%, cholesterol 20%, $Pam_3cys$-MUC1-Tn (9) 2 nM.

Batch 3: DPPC 80%, cholesterol 20%.

Chloroform was removed by subjecting the lipid solutions to a constant stream of nitrogen. The resulting lipid films were dried under vacuum overnight. The dried lipid films were hydrated with 2 mL of HEPES buffer (pH=7.4). The suspensions of the lipids in the buffer were agitated at 43° C. for 40 mins. The suspensions were subjected to 10 freeze-thaw cycles (dry ice/acetone and water at 40° C.). Final liposomes were prepared by extrusion (21 times) using a LipoFast Basic fitted with a 100 nm polycarbonate membrane to control the liposome size.

Figure 13A:
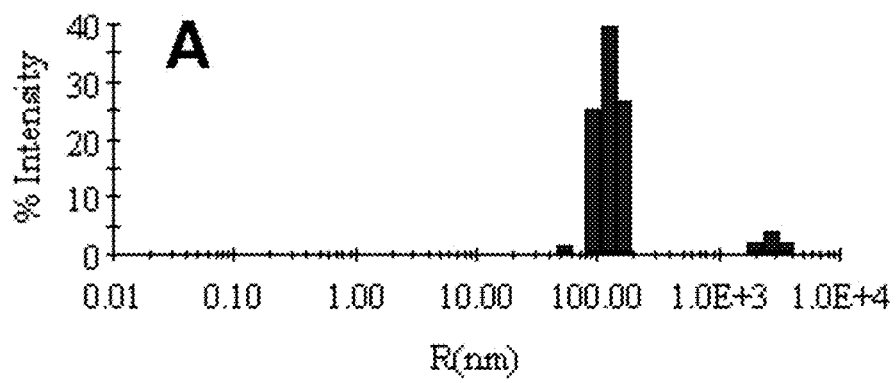
FIGS. 13A-13C: Size characterization of liposomes at 1/10,000 dilution.
Figure 13B:
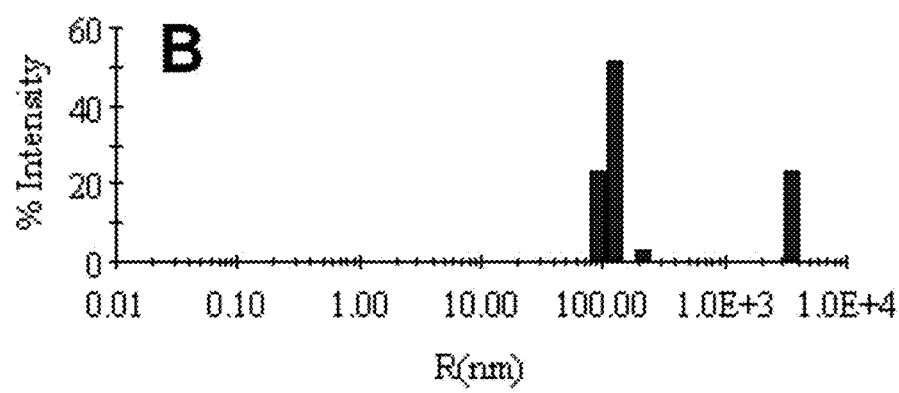
Figure 13C:
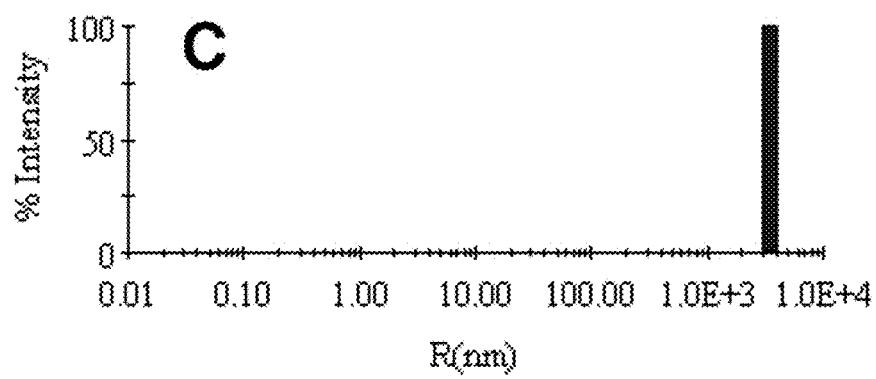

General Characterization of Liposomal Vaccine of Composition I and Control Compositions The homogeneity, stability as well as size characterization of the liposomes were evaluated by scanning electron microscope (SEM) imaging (FIGS. 14A-14B) and dynamic light scattering (DLS) measurements (FIGS. 13A-13C).

All batches of liposomes were found to be stable at 4° C. for 2 days and were around 100 nm in diameter. Antibody binding study showed positive binding of the Batch 1 liposomes with anti-rhamnose antibodies as well as mouse anti-human-MUC1 (CD 227, BD Biosciences, San Jose, Calif.) antibodies using FITC goat anti-mouse IgG/IgM secondary antibodies and fluorescence imaging of the coated liposomes, as shown in FIG. 15.

The binding assay proved that the L-rhamnose and the MUC1 VNTR-TACA conjugate were displayed on the surface of the liposomes. No such antibody binding (both anti-rhamnose and mouse anti-human-MUC1) were observed for the control Batch 3 liposomes.

Batch 2 liposomes only demonstrated mouse anti-human-MUC1 antibody binding.

Example 5

Liposome Characterization

Size Characterization

Size determination of the liposomes was done by scanning electron microscope (SEM) imaging and dynamic light scattering (DLS) measurements. For SEM characterization the liposome samples were diluted 1000 times with HEPES buffer (pH=7.4) and freeze dried over copper studs fitted with a carbon conducting tape and the images recorded at an acceleration voltage of 5 kV. DLS measurements were done after dilution of the liposome samples 10000 times with HEPES buffer (pH=7.4).

Anti-Rha and Anti-MUC1 Antibody Binding to Surface Exposed Rha and MUC1 Epitopes on Liposomes $10^6$ liposomes from each batch in 50 µL, 1×PBS (pH=7.4) were added separately into a 1.5 mL Eppendrof tube followed by 50 µL of primary antibody solution in deionized water containing 5-50 µg/mL of antibodies [either control antibodies (isolated from the serum of non-immunized mice) or anti-Rha antibodies or mouse anti-human CD227 antibodies (anti-human MUC1)] and incubated on ice for 30 mins. 1 mL PBS-0.1% Tween was added to each tube and vortexed. Liposomes were spun at 14000 rpm in Eppendorf centrifuge at 4° C. for 5 mins. The supernatants were carefully discarded and the washing and centrifugation steps were repeated 2 more times for a total of 3 washes. Liposomes were then resuspended in 50 µL of PBS-0.1% Tween. 50 µL of diluted FITC goat anti-mouse IgG/IgM secondary antibody were added (2-30 µg/mL) to the tubes, mixed and covered with aluminum foil to protect from light and incubated on ice for 30 mins. After washing 3 times with PBS-0.1% Tween and centrifugation, the supernatants were removed and pellets were resuspended in 1 mL PBS-0.1% Tween. 10 µL of the resuspended solutions were put on glass slides and imaged under a fluorescent microscope.

Example 6

NMR spectra and HRMS data of compositions (2), (3), (5) and (6) are shown in FIG. 16 through FIG. 31.

Figure 16:
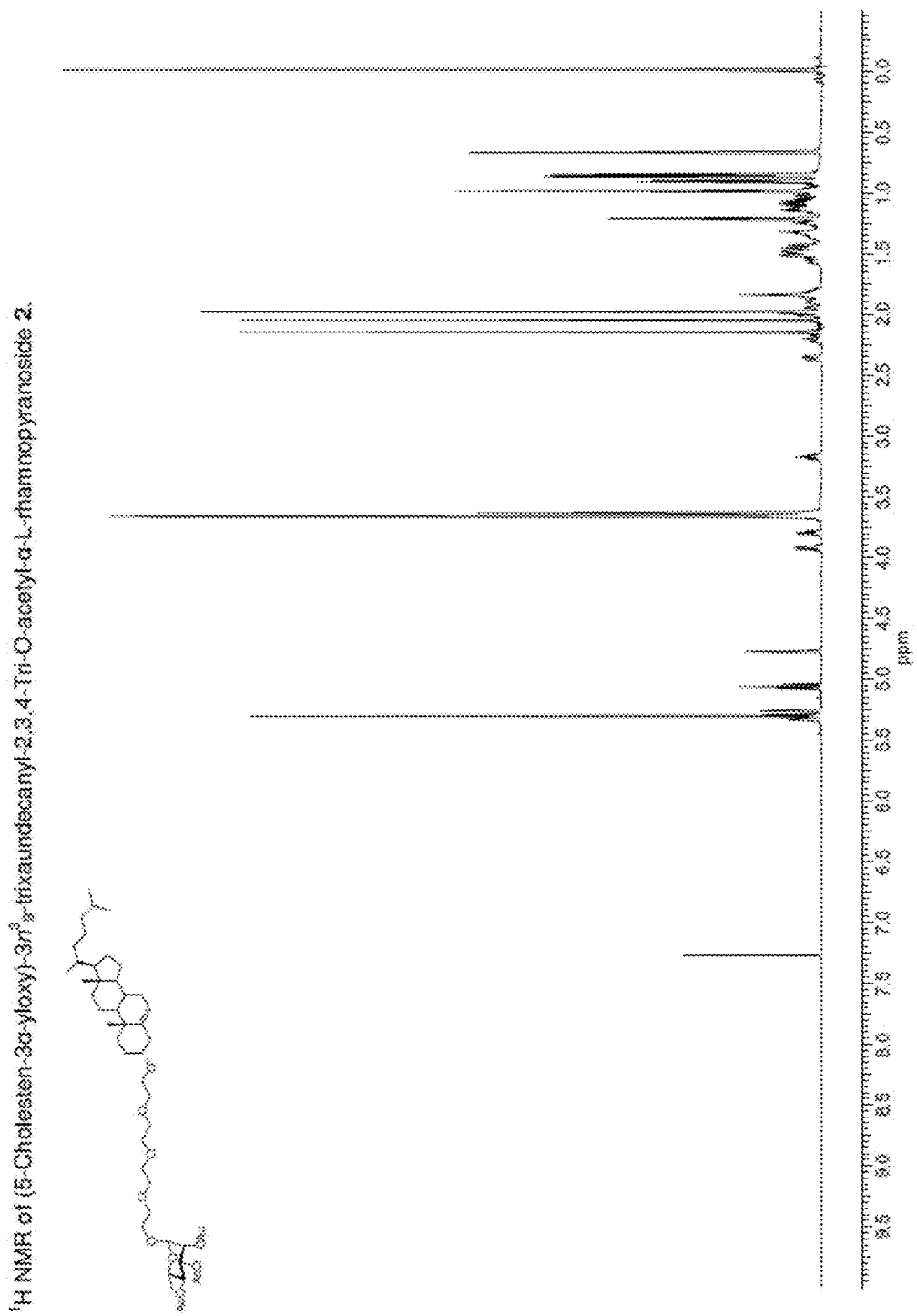
FIG. 16: $^1$H NMR of (5-Cholesten-3α-yloxy)-3n$^3{}_9$-trix-aundecanyl-2,3,4-tri-O-acetyl-α-L-Rhamnopyranoside (2).

FIG. 16: $^1$H NMR of (5-Cholesten-3α-yloxy)-3n$^3$$_9$-trix-aundecanyl-2,3,4-tri-O-acetyl-α-L-Rhamnopyranoside (2).

Figure 17:
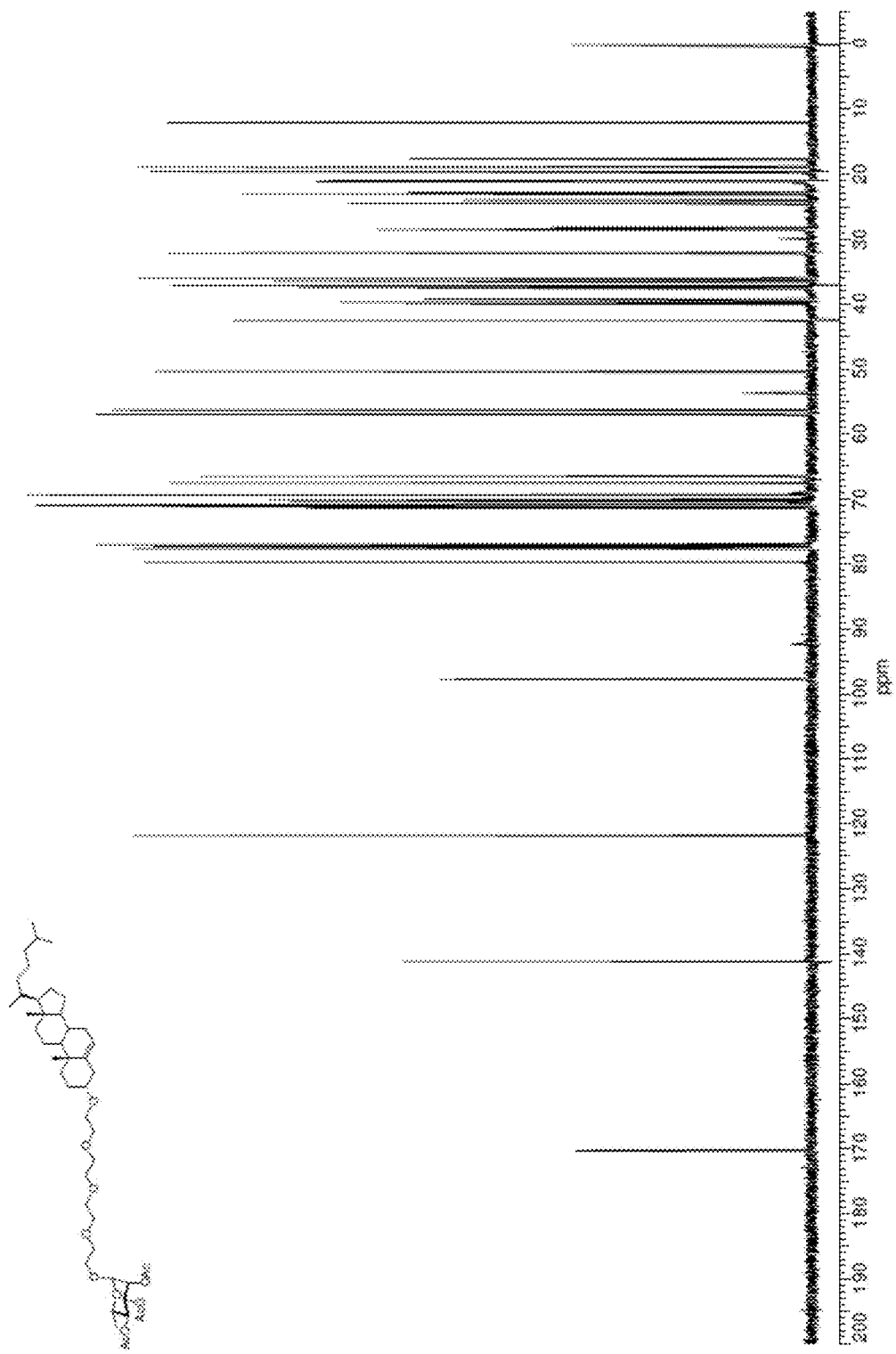
FIG. 17: $^{13}$C NMR of (5-Cholesten-3α-yloxy)-3n$^3{}_9$-trix-aundecanyl-2,3,4-tri-O-acetyl-α-L-Rhamnopyranoside (2).

FIG. 17: $^{13}$C NMR of (5-Cholesten-3α-yloxy)-3n$^3$$_9$-trix-aundecanyl-2,3,4-tri-O-acetyl-α-L-Rhamnopyranoside (2).

Figure 18:
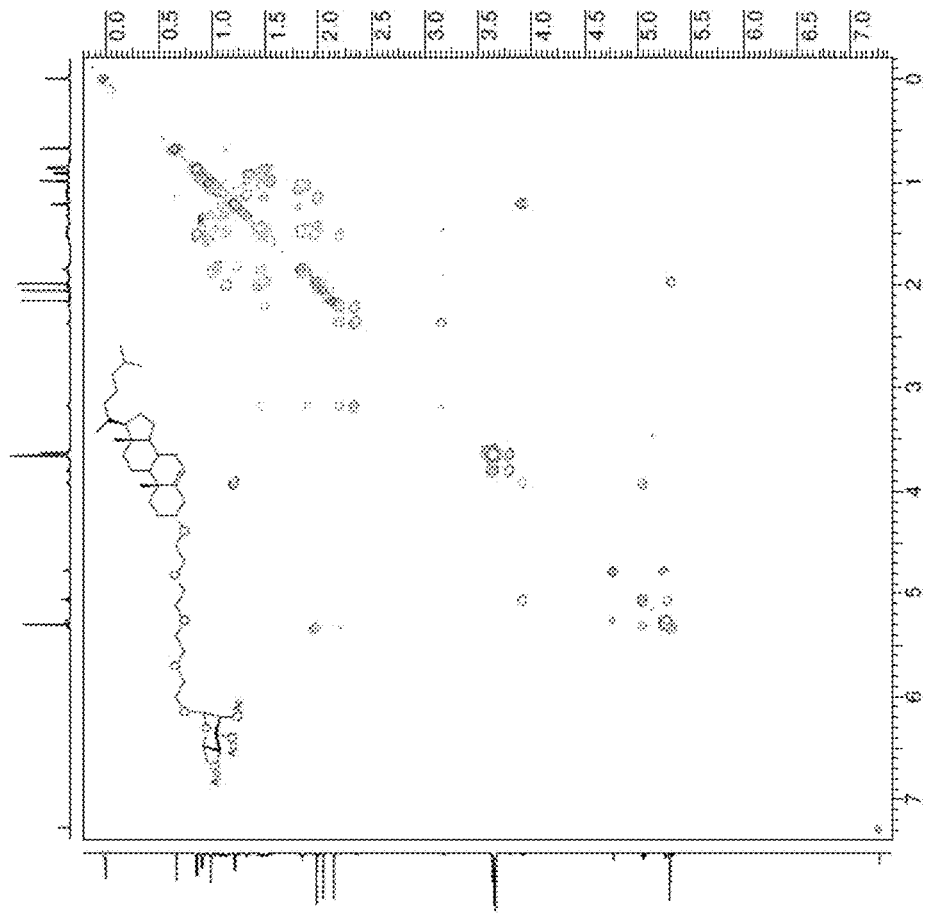
FIG. 18: $^1$H-gCosy of (5-Cholesten-3α-yloxy)-3n$^3{}_9$-trix-aundecanyl 2,3,4-tri-O-acetyl-α-L-Rhamnopyranoside (2).

FIG. 18: $^1$H-gCosy of (5-Cholesten-3α-yloxy)-3n$^3$$_9$-trix-aundecanyl 2,3,4-tri-O-acetyl-α-L-Rhamnopyranoside (2).

Figure 19:
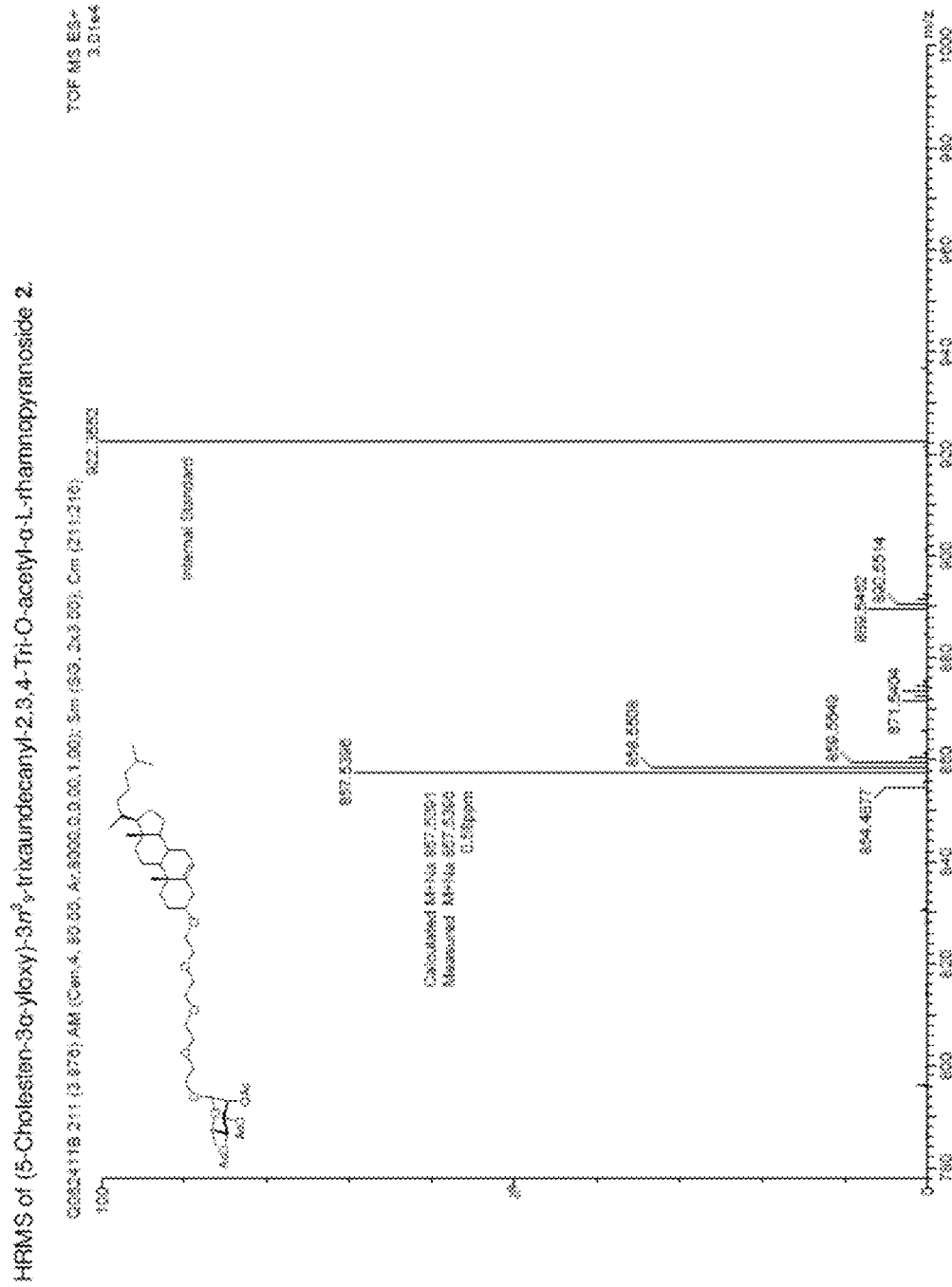
FIG. 19: HRMS of (5-Cholesten-3α-yloxy)-3n$^3{}_9$-trixaundecanyl 2,3,4-tri-O-acetyl-α-L-Rhamnopyranoside (2).

FIG. 19: HRMS of (5-Cholesten-3α-yloxy)-3n$^3$$_9$-trixaun-decanyl 2,3,4-tri-O-acetyl-α-L-Rhamnopyranoside (2).

Figure 20:
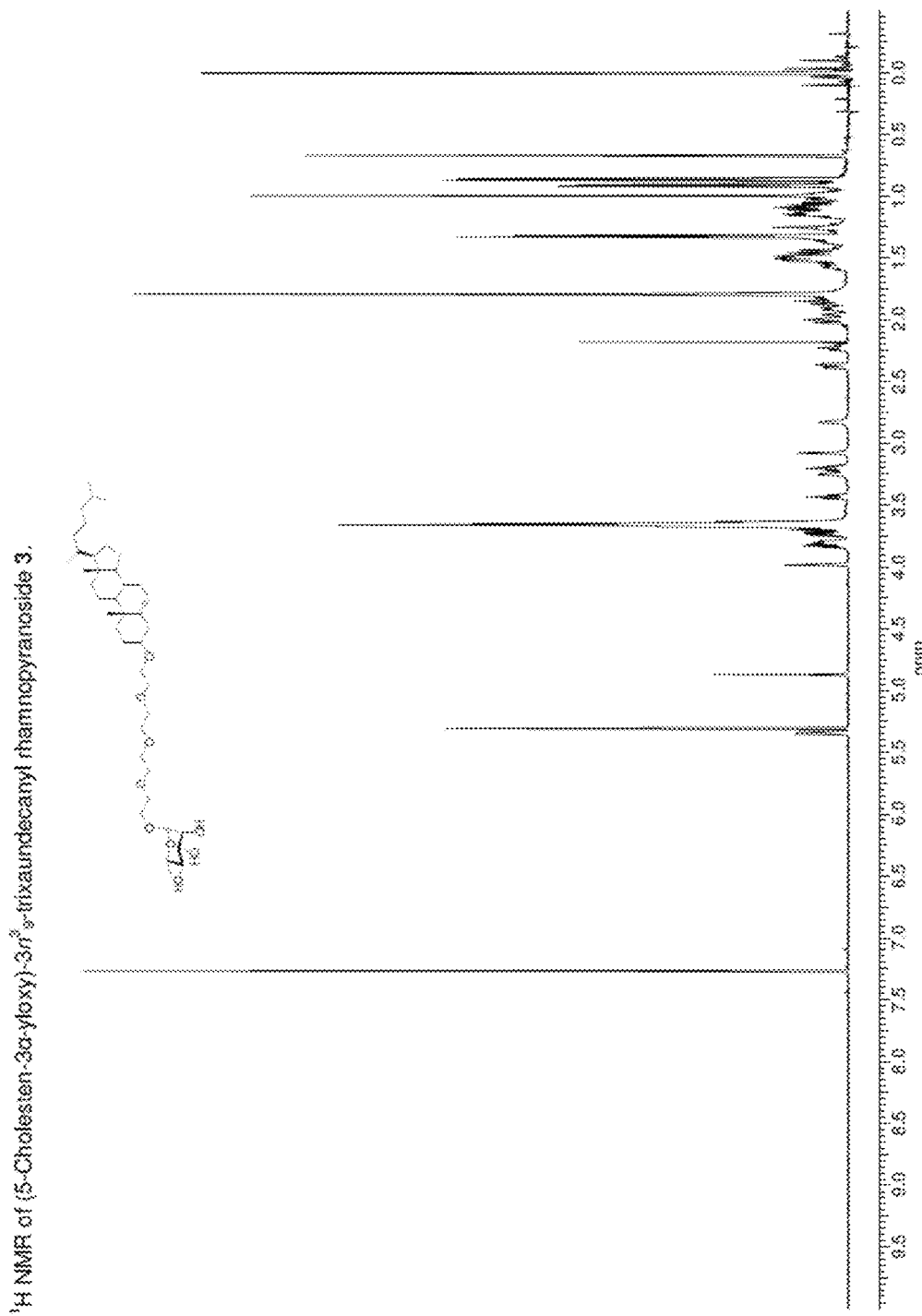
FIG. 20: $^1$H NMR of (5-Cholesten-3α-yloxy)-3n$^3{}_9$-trix-aundecanyl Rhamnopyranoside (3).

FIG. 20: $^1$H NMR of (5-Cholesten-3α-yloxy)-3n$^3$$_9$-trix-aundecanyl Rhamnopyranoside (3).

Figure 21:
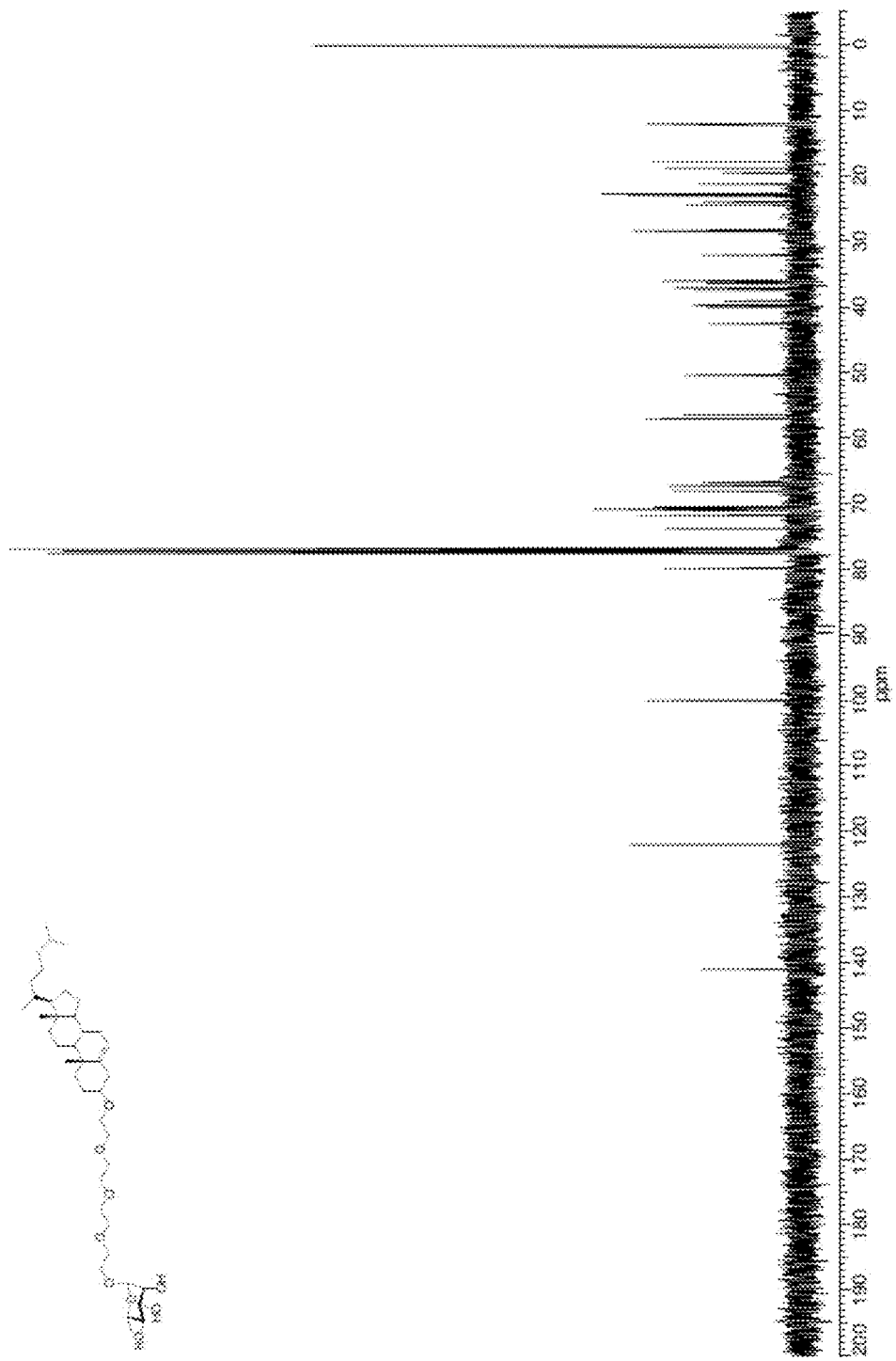
FIG. 21: $^{13}$C NMR of (5-Cholesten-3α-yloxy)-3n$^3{}_9$-trix-aundecanyl Rhamnopyranoside (3).

FIG. 21: $^{13}$C NMR of (5-Cholesten-3α-yloxy)-3n$^3$$_9$-trix-aundecanyl Rhamnopyranoside (3).

Figure 22:
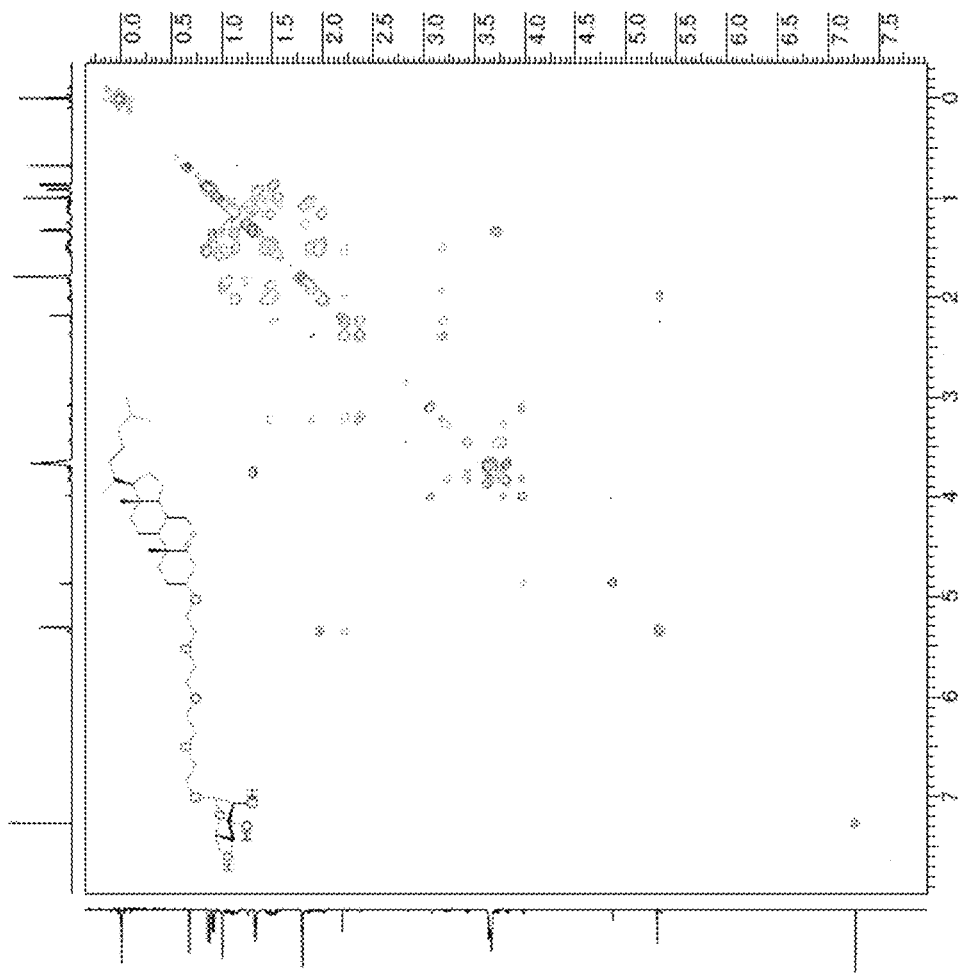
FIG. 22: $^1$H-gCosy of (5-Cholesten-3α-yloxy)-3n$^3{}_9$-trix-aundecanyl Rhamnopyranoside (3).

FIG. 22: $^1$H-gCosy of (5-Cholesten-3α-yloxy)-3n$^3$$_9$-trix-aundecanyl Rhamnopyranoside (3).

Figure 23:
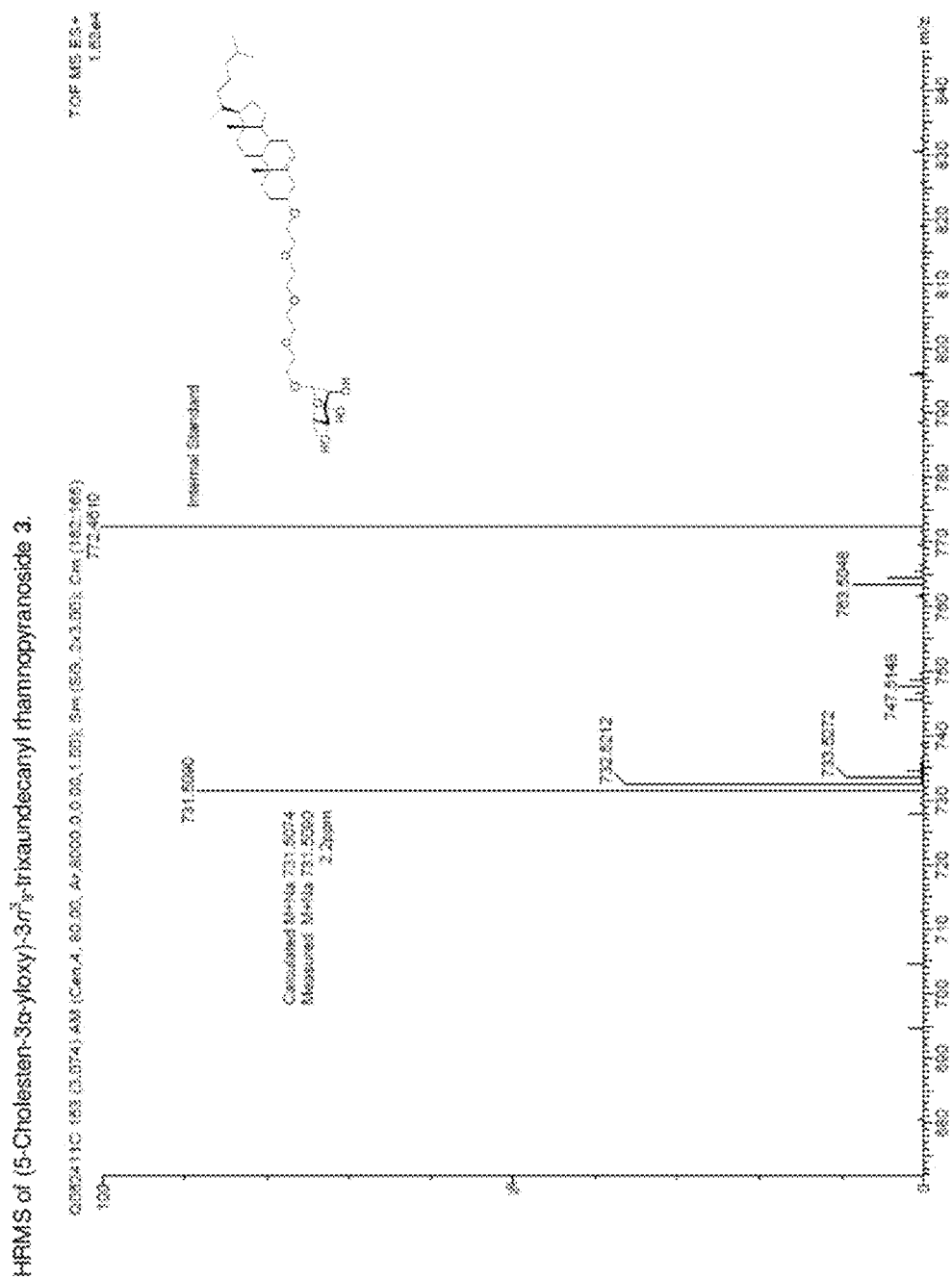
FIG. 23: HRMS of (5-Cholesten-3α-yloxy)-3n$^3{}_9$-trixaundecanyl Rhamnopyranoside (3).

FIG. 23: HRMS of (5-Cholesten-3α-yloxy)-3n$^3$$_9$-trixaun-decanyl Rhamnopyranoside (3).

Figure 24:
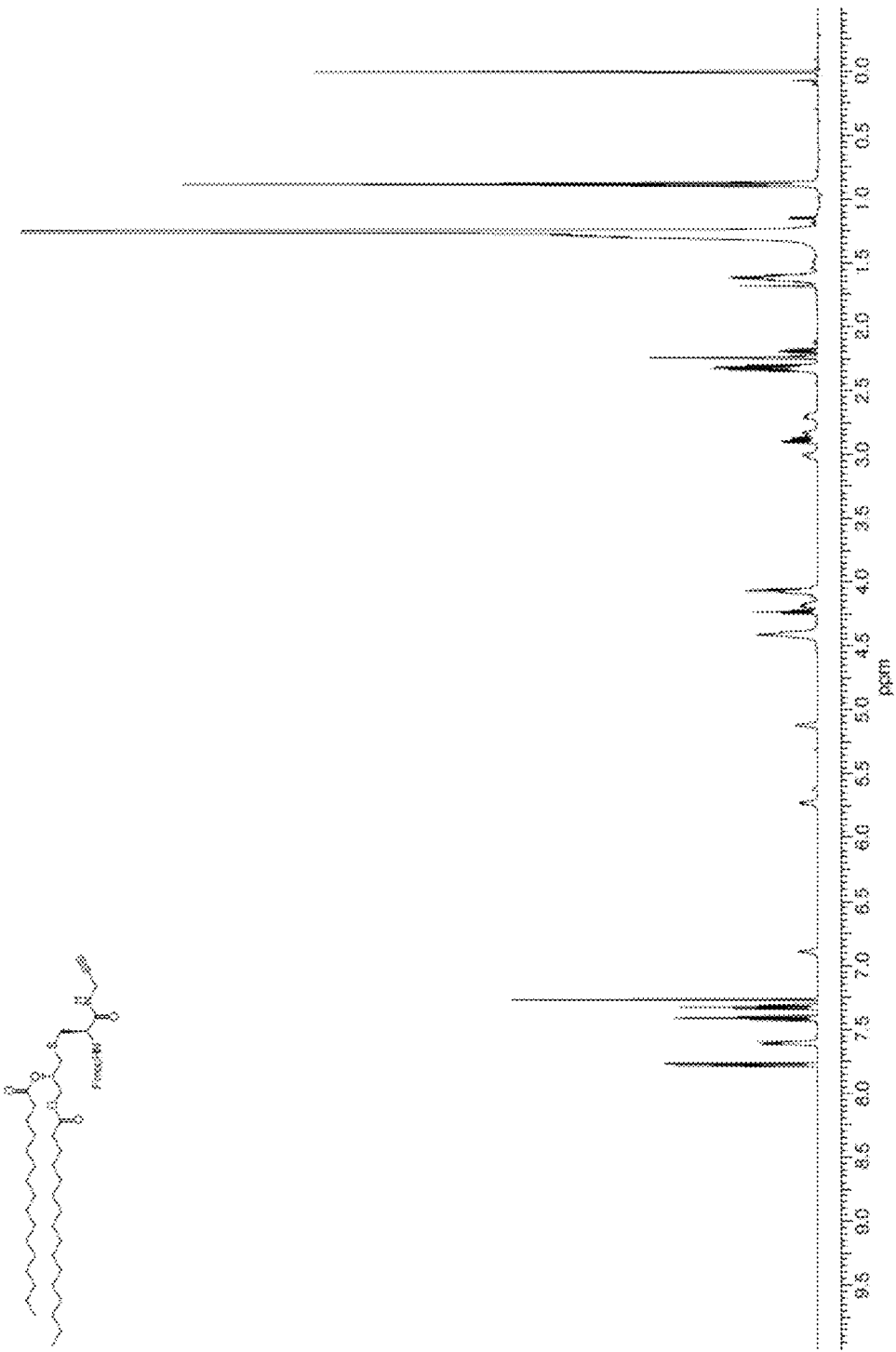
FIG. 24: $^1$H NMR of N-Propargyl Pam$_2$FmocCys Amide Derivative (5).

FIG. 24: $^1$H NMR of N-Propargyl Pam$_2$FmocCys Amide Derivative (5).

Figure 25:
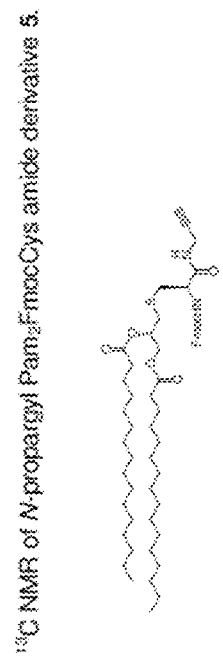
FIG. 25: $^{13}$C NMR of N-Propargyl Pam$_2$FmocCys Amide Derivative (5).
Figure 25:
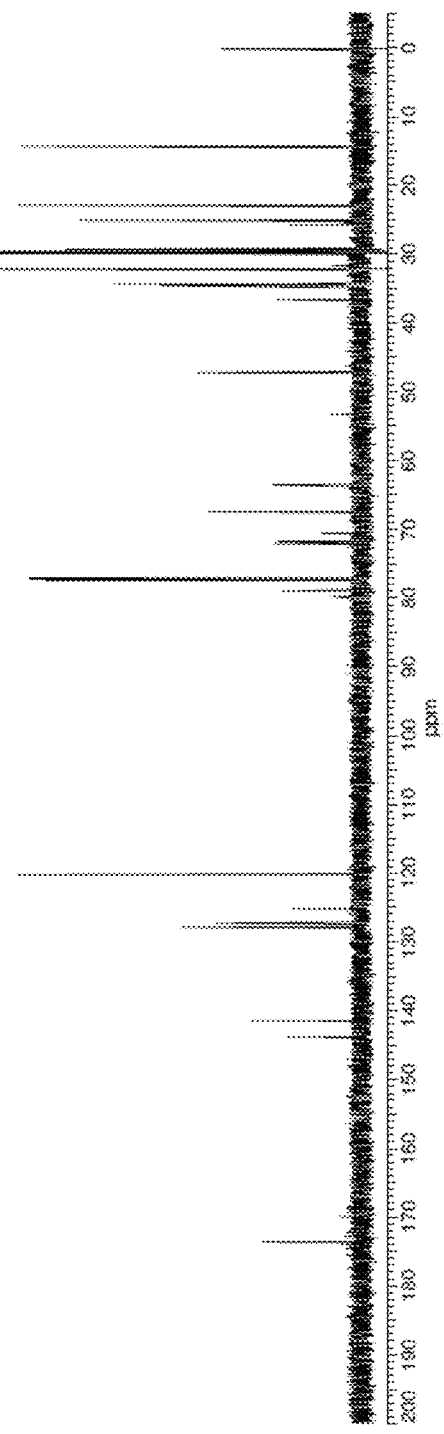

FIG. 25: $^{13}$C NMR of N-Propargyl Pam$_2$FmocCys Amide Derivative (5).

Figure 26:
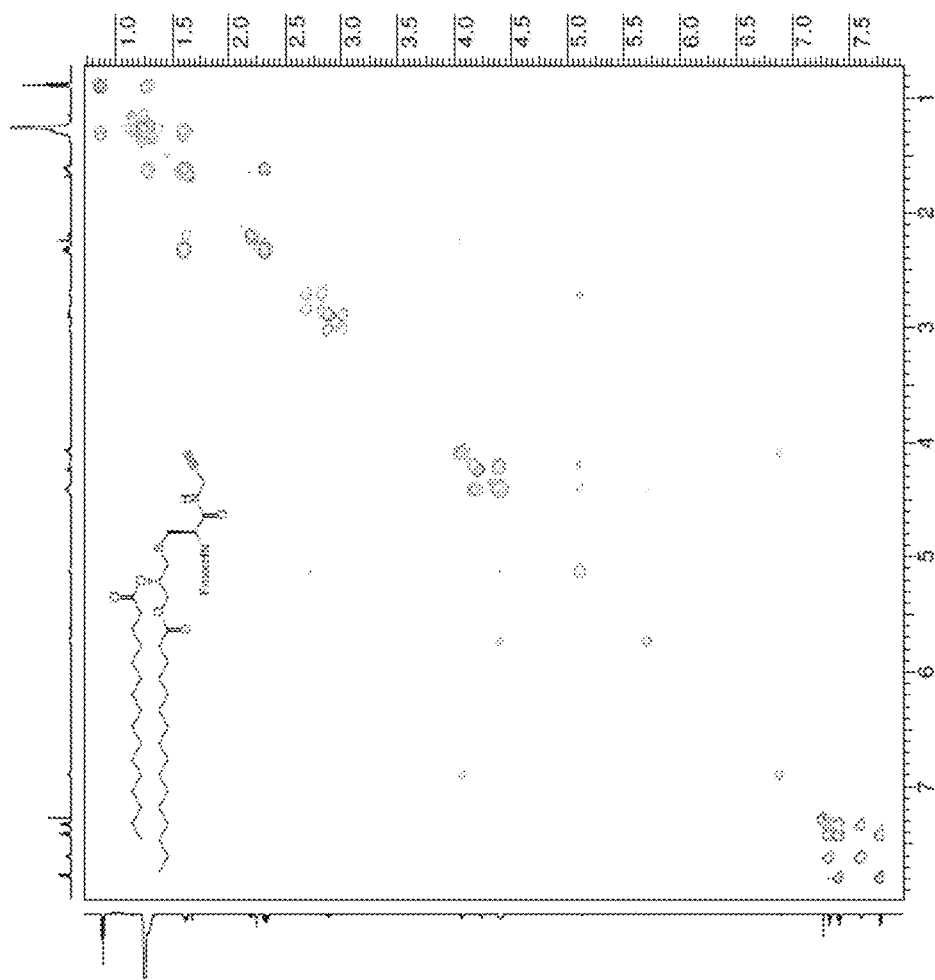
FIG. 26: $^1$H gCosy of N-Propargyl Pam$_2$FmocCys Amide Derivative (5).

FIG. 26: $^1$H gCosy of N-Propargyl Pam$_2$FmocCys Amide Derivative (5).

Figure 27:
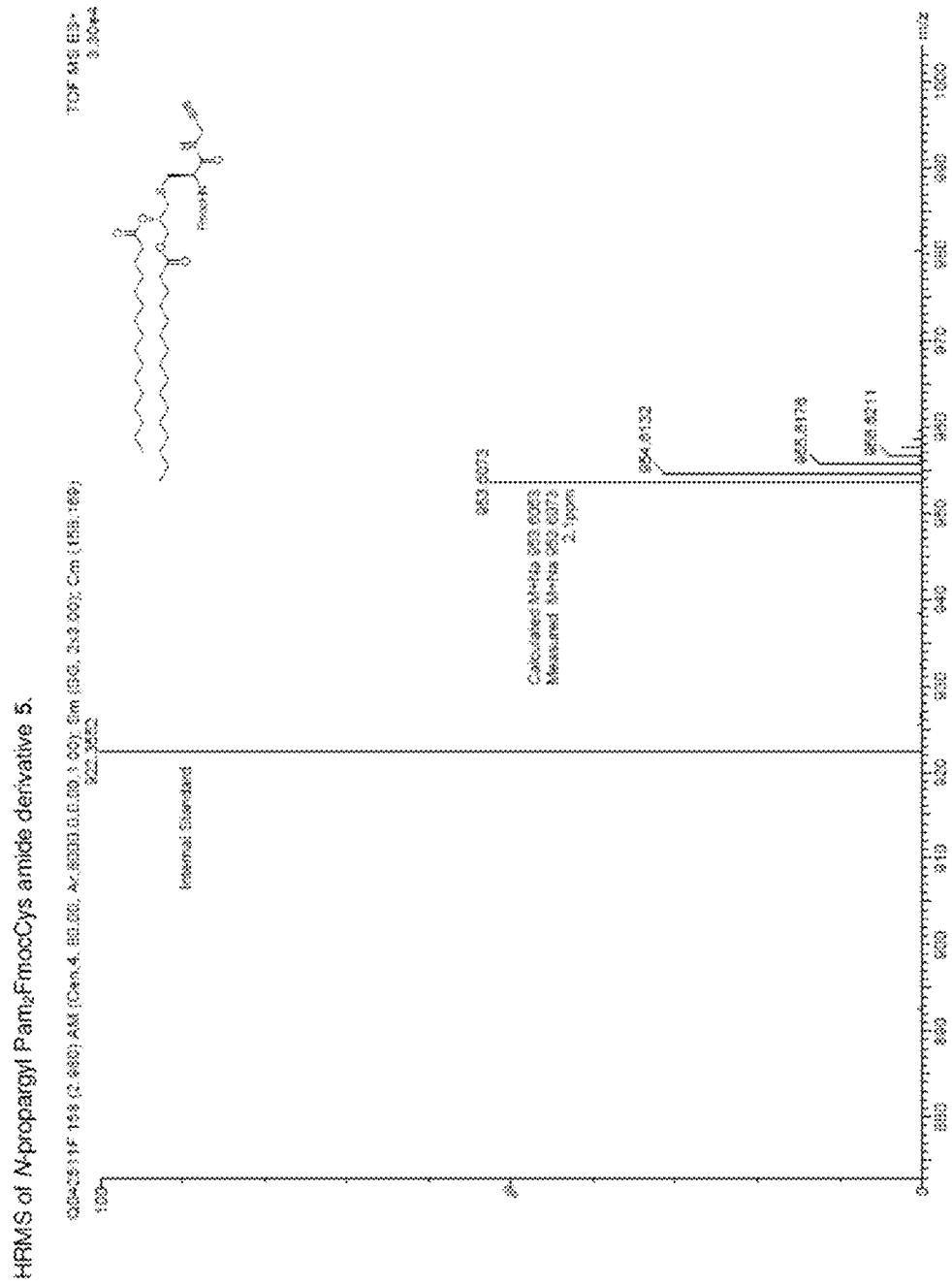
FIG. 27: HRMS of N-Propargyl Pam$_2$FmocCys Amide Derivative (5).

FIG. 27: HRMS of N-Propargyl Pam$_2$FmocCys Amide Derivative (5).

Figure 28:
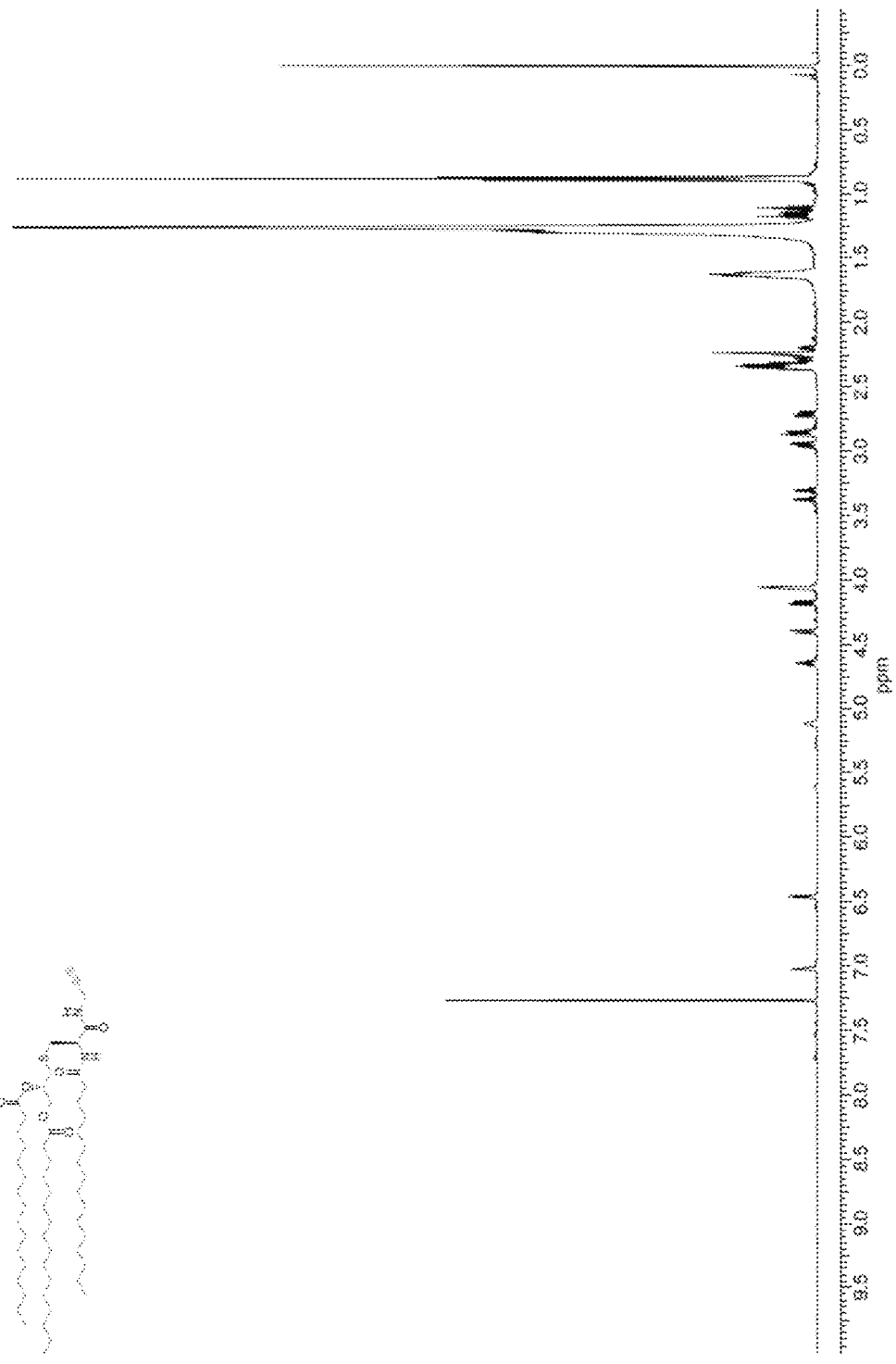
FIG. 28: $^1$H NMR of N-Propargyl Pam$_3$Cys Amide Derivative (6).

FIG. 28: $^1$H NMR of N-Propargyl Pam$_3$Cys Amide Derivative (6).

Figure 29:
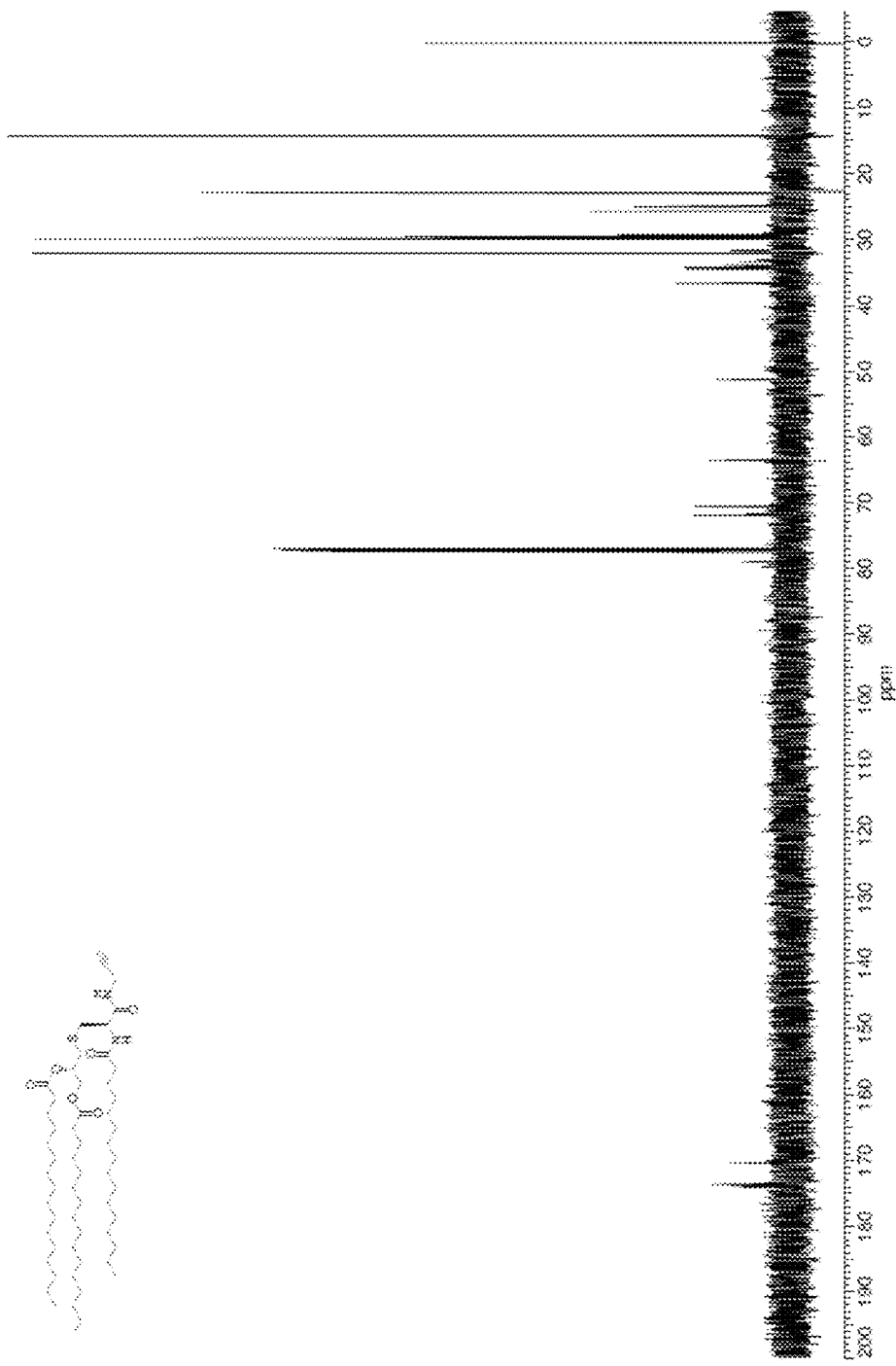
FIG. 29: $^{13}$C NMR of N-Propargyl Pam$_3$Cys Amide Derivative (6).
Figure 29:

FIG. 29: $^{13}$C NMR of N-Propargyl Pam$_3$Cys Amide Derivative (6).

Figure 30:
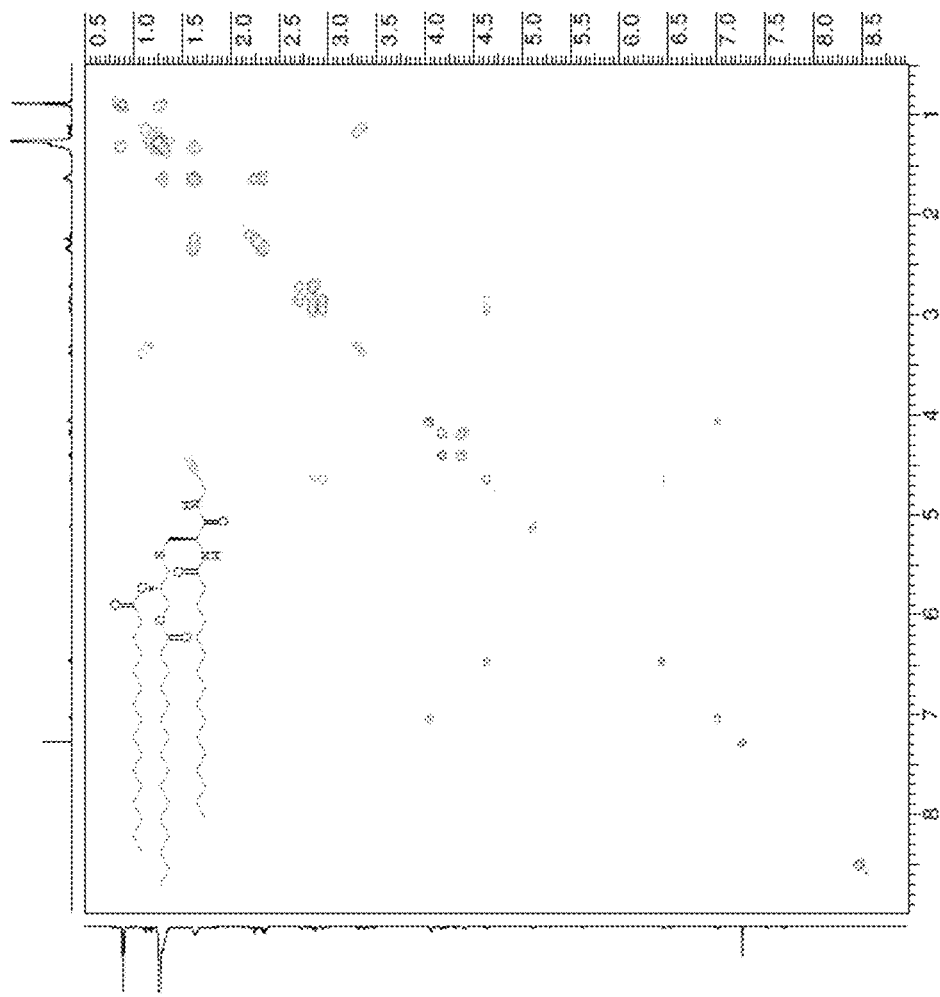
FIG. 30: $^1$H-gCosy of N-Propargyl Pam$_3$Cys Amide Derivative (6).

FIG. 30: $^1$H-gCosy of N-Propargyl Pam$_3$Cys Amide Derivative (6).

Figure 31:
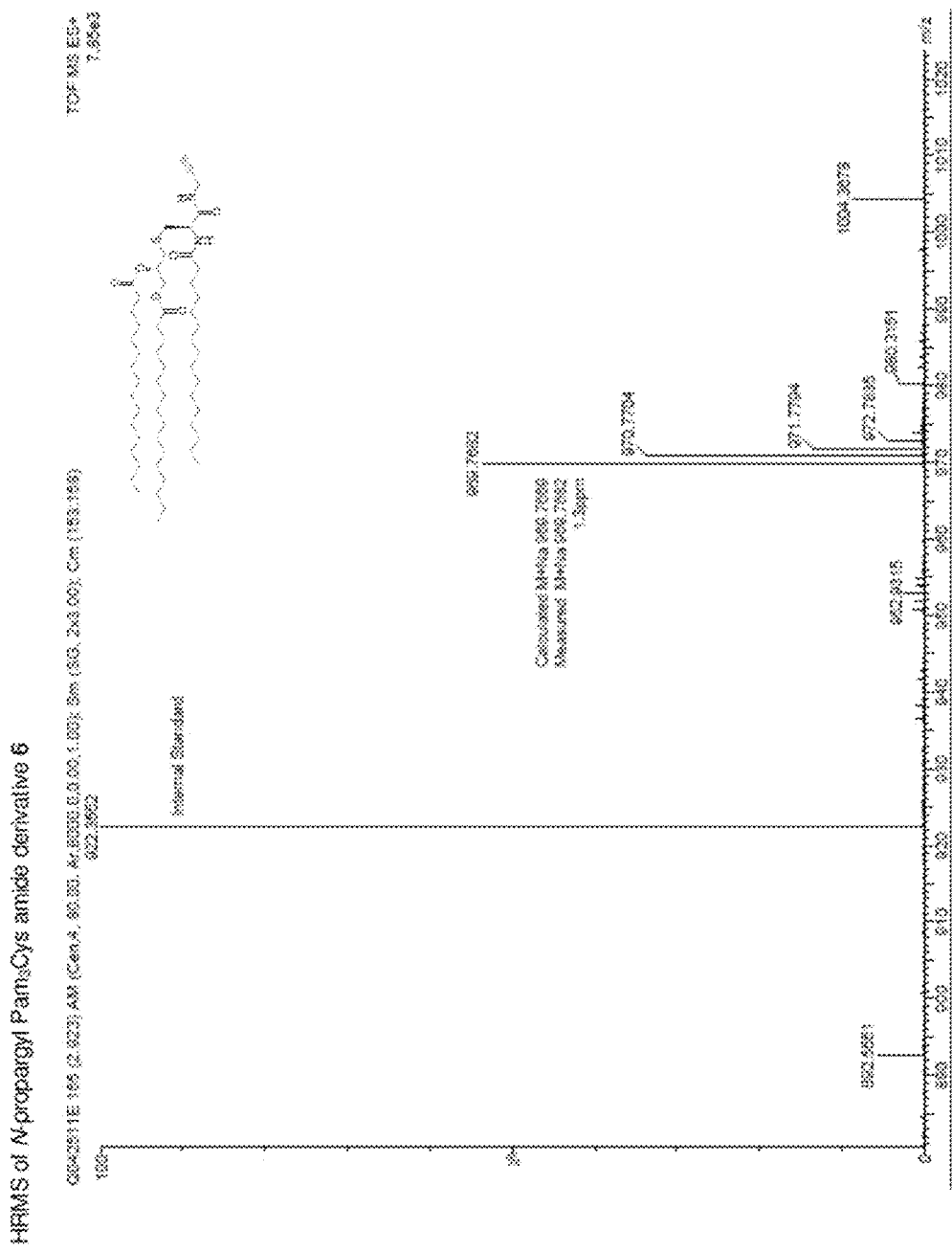
FIG. 31: HRMS of N-Propargyl Pam$_3$Cys Amide Derivative (6).

FIG. 31: HRMS of N-Propargyl Pam$_3$Cys Amide Derivative (6).

Figure 32:
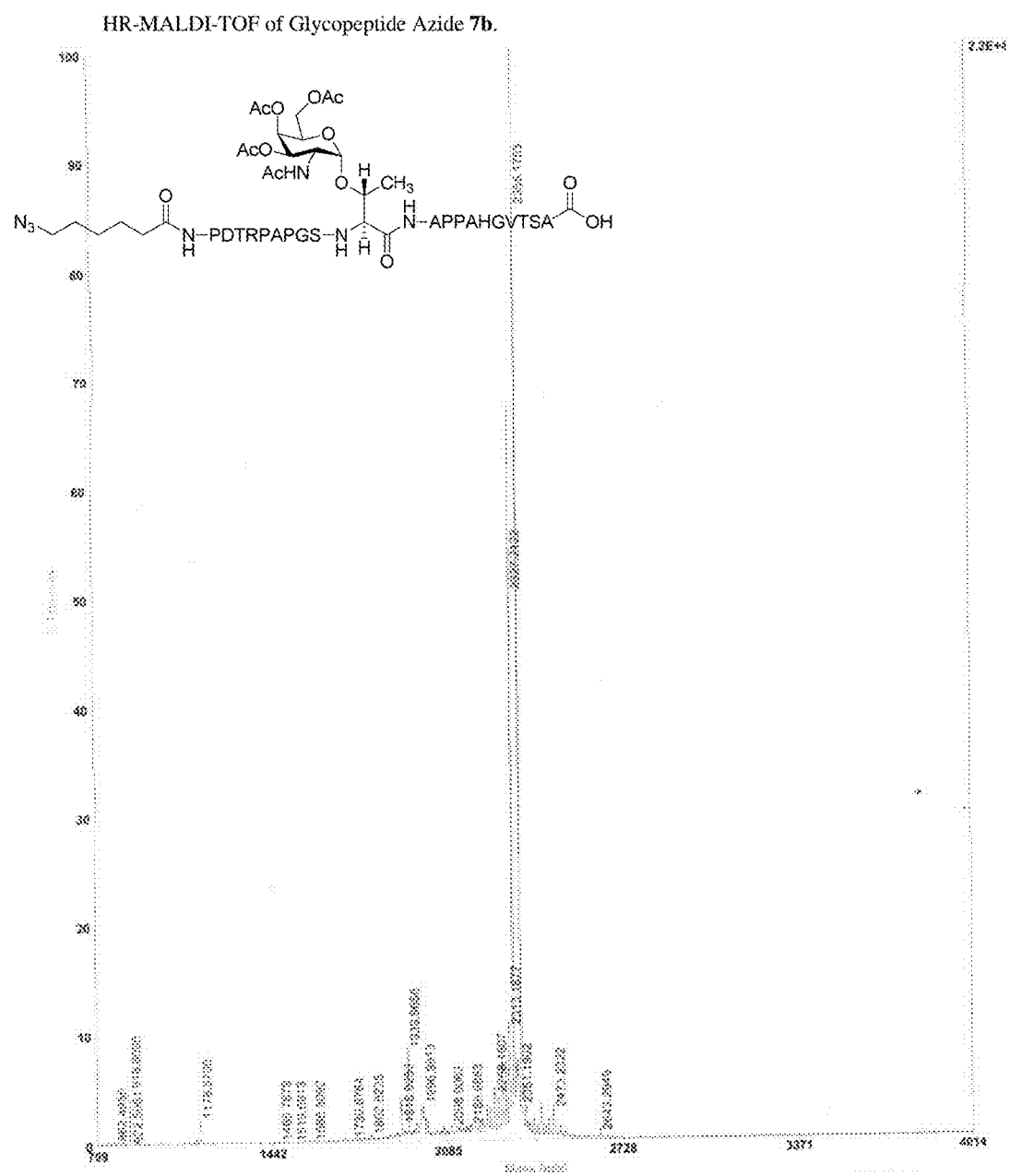
FIG. 32: HR-MALDI-TOF of Glycopeptide Azide (9) [SEQ ID NO:8].
Figure 33:
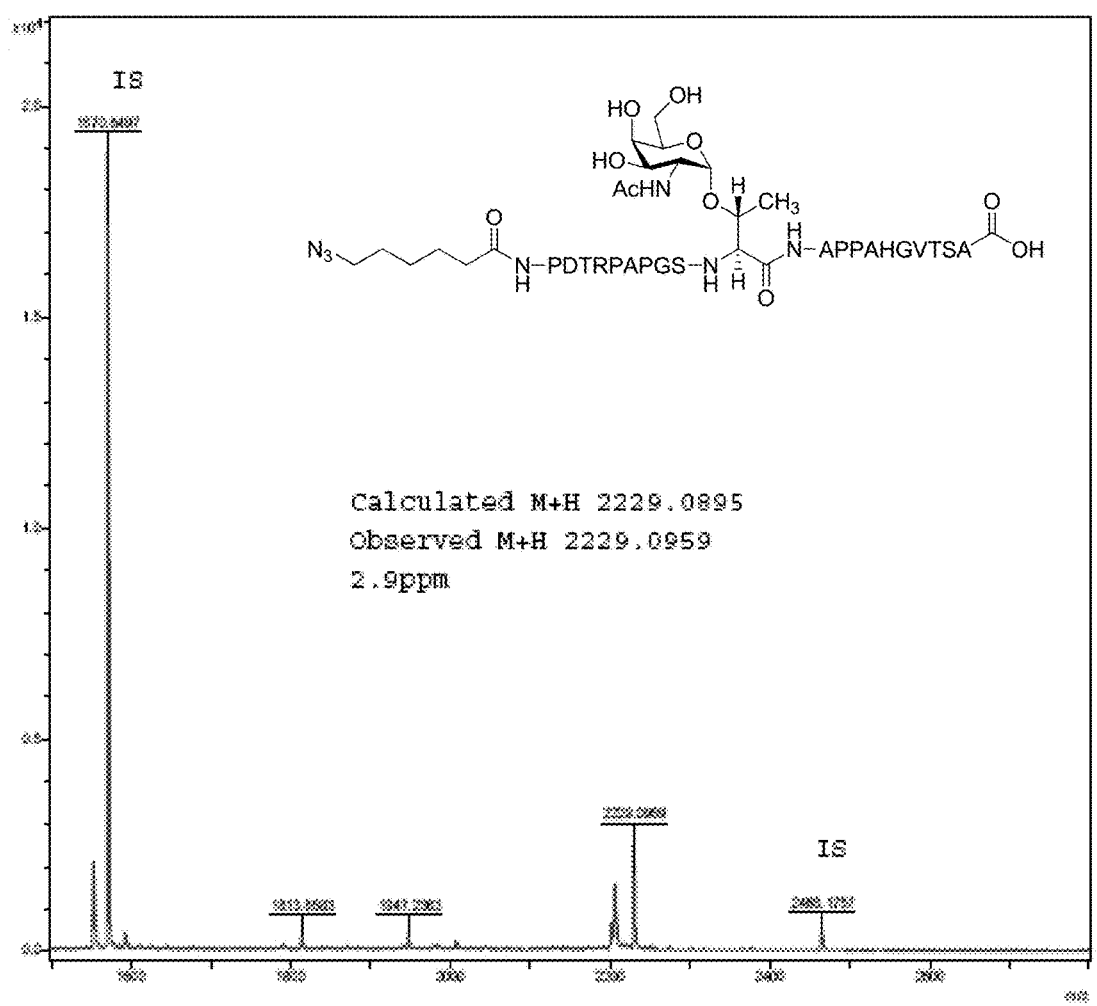
FIG. 33: HR-MALDI-TOF of Glycopeptide Azide (8) [SEQ ID NO: 10].
Figure 34:
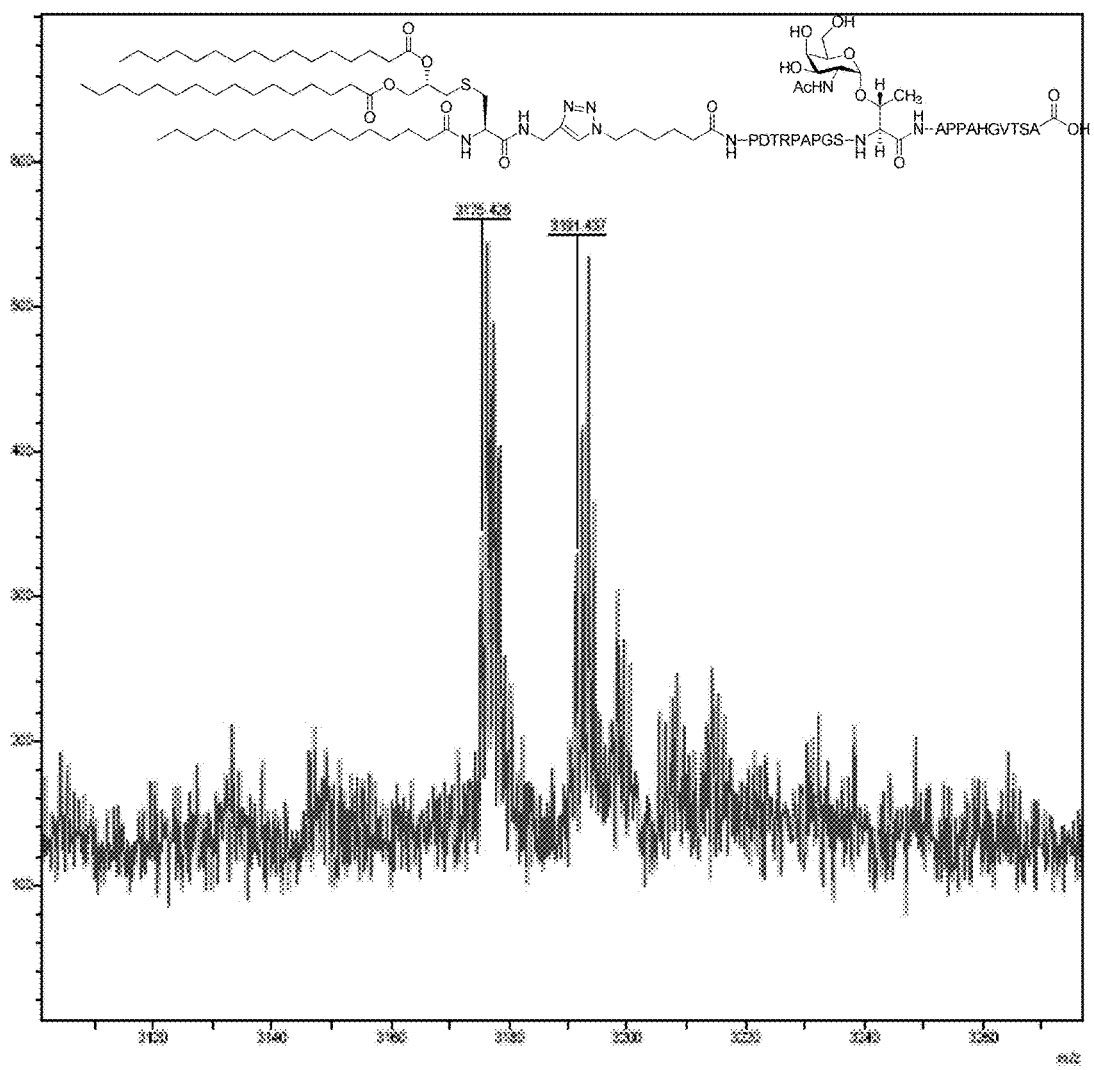
FIG. 34: HR-MALDI-TOF of Lipopeptide (9) [SEQ ID NO:7].
Figure 35:
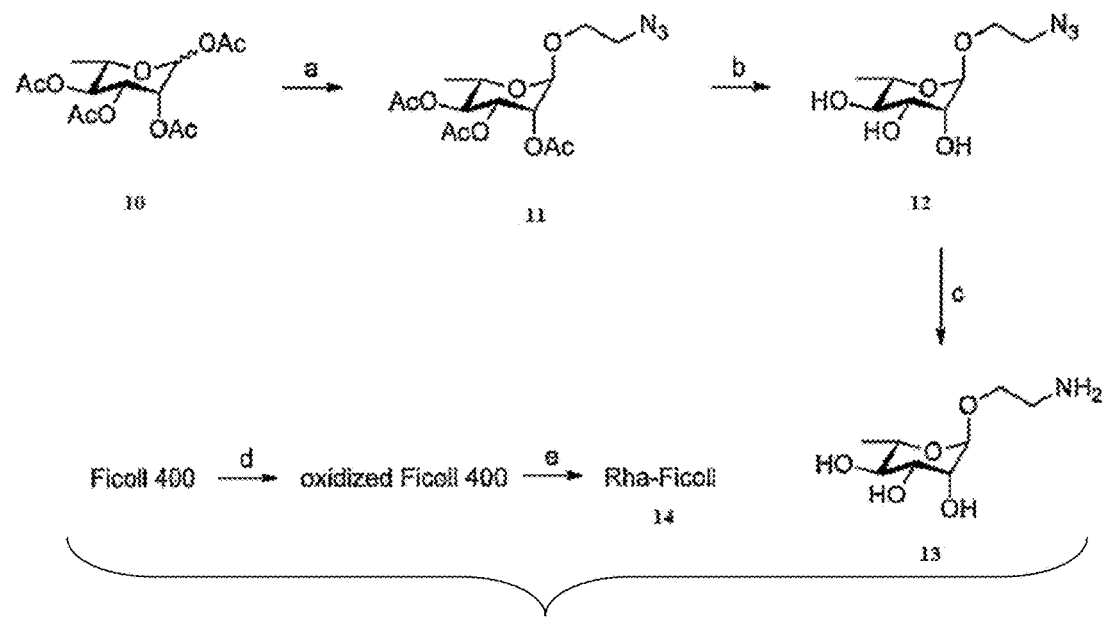
FIG. 35: Scheme showing synthetic route of 2-Aminoethyle-α-L-Rhamnopyranoside (13).

The MALDI-TOF spectra data for compositions (7b), (8) and (9) are shown in FIG. 32 through FIG. 34.

FIG. 32: HR-MALDI-TOF of Glycopeptide Azide (7b).

FIG. 33: HR-MALDI-TOF of Glycopeptide Azide (8).

FIG. 34: HR-MALDI-TOF of Lipopeptide (9).

Example 7

2-Azidoethyl-2,3,4-Tri-O-Acetyl-α-L-Rhamnopyranoside (II)

To a solution of 1,2,3,4-tetra-O-acetylrhamnopyranoside (10) (2.00 g, 6.02 mmol) in CH$_2$Cl$_2$ (5.00 mL) were added 2-azidoethanol (0.79 g, 9.03 mmol) and BF$_3$.OEt$_2$ (1.53 mL, 12.04 mmol) at 0° C. and the resulting solution was stirred at ambient temperature under N$_2$ atmosphere. The reaction was monitored by TLC and appeared to be completed after 12 h. The reaction mixture was diluted with CH$_2$Cl$_2$ (15 mL) and washed with water (2×20 mL), saturated NaHCO$_3$ (2×20 mL) and brine (20 mL), after which the organic layer was dried over anhydrous Na$_2$SO$_4$. Excess solvent was removed under reduced pressure and the crude material was purified by silica gel flash column chromatography (3.3×8.5 cm). Elution with 1:5 EtOAc/hexanes afforded (11) as a colorless solid (1.78 g, 83%). $^1$H NMR (600 MHz, CDCl$_3$): δ 1.24 (d, 3H, J=6.6 Hz, C-5 CH$_3$), 1.99 (s, 3H, COCH$_3$), 2.06 (s, 3H, COCH$_3$), 2.16 (s, 3H, COCH$_3$), 3.42 (m, 1H, —CHH—N$_3$), 3.48 (m, 1H, —CHH—N$_3$), 3.64 (m, 1H, —O—CHH), 3.87 (m, 1H, —O—CHH), 3.93 (m, 1H, H-5), 4.79 (d, 1H, J=1.8 Hz, H-1), 5.09 (t, 1H, J=10.2 Hz, H-4), 5.27 (dd, 1H, J=1.2, 3.3 Hz, H-2), 5.31 (dd, 1H, J=3.3, 9.9 Hz, H-3). $^{13}$C NMR (100 MHz, CDCl$_3$): δ 17.66 (CH$_3$), 20.93, 21.03, 21.13, 50.58, 66.91, 66.99, 69.08, 69.87, 71.09, 97.79 (C-1), 170.09 (C=O), 170.24 (C=O), 170.30 (C=O). HRMS [M+Na] m/z: calcd for C$_{14}$H$_{21}$N$_3$O$_8$, 382.1226. found, 382.1215.

2-Azidoethyl-α-L-Rhamnopyranoside (12)

To a solution of (11) (1.53 g, 4.26 mmol) in MeOH (5 mL) was added metallic Na (0.01 g) and the resulting solution was stirred at ambient temperature under N$_2$ atmosphere. The reaction was monitored by TLC and appeared complete after 2 h. Excess solvent was removed under reduced pressure and the crude material was purified by silica gel flash column chromatography (3.3×8.5 cm). Elution with 2:23 MeOH/CH$_2$Cl$_2$ yielded (12) as a colorless solid (0.85 g, 86%). $^1$H NMR (600 MHz, CDCl$_3$): δ 1.34 (d, 3H, J=6.6 Hz, C-5 CH$_3$), 3.41 (m, 2H, —CH$_2$—N$_3$), 3.49 (t, 1H, J=9.3 Hz, H- 4), 3.63 (m, 1H, —O—CHH), 3.69 (m, 1H, H-5), 3.81 (dd, 1H, J=3.3, 9.3 Hz, H-3), 3.89 (m, 1H, —O—CHH), 3.99 (q, 1H, J=1.6 Hz, H-2), 4.83 (d, 1H, J=1.2 Hz, H-1). $^{13}$C NMR (100 MHz, CDCl$_3$): δ 17.75 (CH$_3$), 50.71, 66.72, 68.49, 70.98, 71.76, 73.27, 100.02 (C-1). HRMS [M+Na] m/z: calc for C$_8$H$_{15}$N$_3$O$_5$, 256.0909. found, 256.0906.

2-Aminoethyl-α-L-Rhamnopyranoside (13)

To a solution of (12) (0.42 g, 1.82 mmol) in MeOH (3 mL) was added activated Pd/charcoal (0.025 g) and the resulting solution was stirred at ambient temperature under H$_2$ atmosphere. The reaction was monitored by TLC and appeared to be complete after 12 h. The reaction mixture was diluted with MeOH (2 mL), filtered through Celite and concentrated under reduced pressure to yield (13) as a colorless gel (0.46 g, quantitative) which was used without further purification for subsequent reactions. ESIMS [M+H] m/z: calcd for C$_8$H$_{17}$NO$_5$, 208.2243. found, 208.30.

2-Aminoethyl-α-L-Rhamnopyranoside-Ficoll Conjugate (14)

Ficoll 400 (1.00 g, 0.0025 mmol) was dissolved in acetate buffer (10 mL, pH 4.7) and NaIO$_4$ (0.01 g, 0.047 mmol) was added and the reaction mixture was stirred at ambient temperature for 2 h in the dark. Excess NaIO$_4$ was removed by dialysis against the acetate buffer (pH 4.7) through dialysis tubing with a molecular weight cutoff value of 10000 Da with six to seven changes of the buffer at 4° C. The oxidized Ficoll 400 was transferred to a round bottom flask and excess solvent was evaporated to dryness under reduced pressure. The residue was dissolved in borate buffer (20 mL, pH 8.0) followed by the addition of (13) (0.05 g, 0.25 mmol) and stirred at ambient temperature for 2 h. To the reaction mixture was added NaBH$_3$CN (0.094 g, 1.50 mmol) and the resulting solution was incubated overnight at 4° C. The mixture was dialyzed through dialysis tubing with a molecular weight cutoff of 10000 Da with six to seven changes in buffer at 4° C. to afford (14). The epitope ratio of (14) was calculated to be 9.44 (Rha:Ficoll) by hydrolysis of (14) followed by derivatization with 4-amino-N-[2-(diethylamino)ethyl] benzamide (DEAEAB) and comparison of the UV-HPLC peak area with a standard curve obtained from DEAEAB derivative of (12) by the methods described by Dalpathado and coworkers. Briefly, the standard curve was generated by refluxing compound (12) (0.007 g, 0.031 mmol) with 1 M HCl at 100° C. for 4 h and the reaction mixture was evaporated to dryness. The residue was dissolved in tetrahydrofuran (2 mL). DEAEAB (0.011 g, 0.037 mmol) and Et$_3$N (0.007 mL, 0.046 mmol) were added and the resulting solution was refluxed for 2 h. The reaction mixture was evaporated to dryness and the residue was dissolved in MeOH (2 mL) followed by the addition of NaB(OAc)$_3$H, and the resulting solution refluxed for 8 h. The solution was evaporated to dryness and the residue was dissolved in MeOH (2 mL) and filtered through a syringe filter. Serial dilutions from this stock solution were prepared and the components were separated on a reverse phase HPLC using a C18 column. Water containing 0.1% TFA (A) and 95% ACN/H$_2$O (B) was used as the mobile phases using a linear gradient (5-20% B in 20 min) at the flow rate of 1 mL/min. Absorbances were recorded at 289 nm. The standard curve was generated by plotting the UV-HPLC peak area against the concentration in mmol of DEAEAB derivative of (12).

NMR spectra and HRMS data of compositions (11), (12), and (13) are shown in FIG. 43 through FIG. 51.

Figure 43:
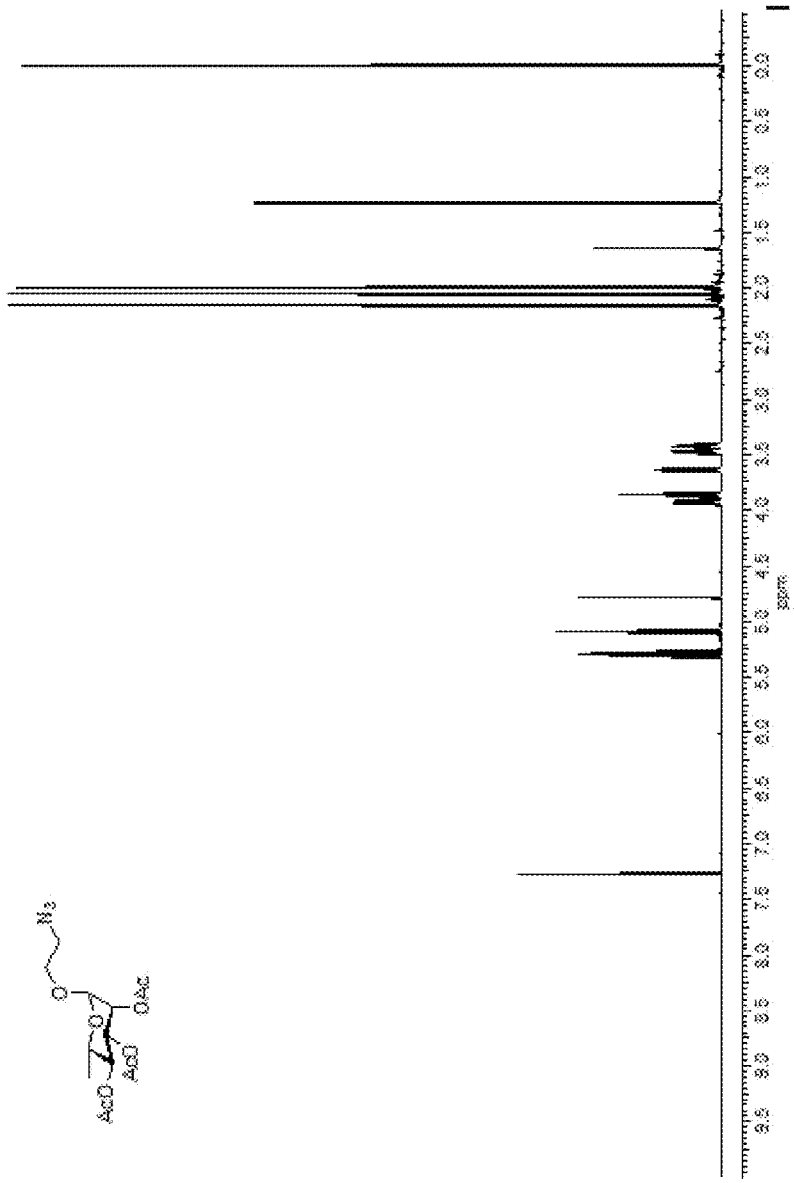
FIG. 43: $^1$H NMR of 2-Azidoethyl-2,3,4-Tri-O-acetyl-α-L-rhamnopyranoside (11).

FIG. 43: $^1$H NMR of 2-Azidoethyl-2,3,4-Tri-O-acetyl-α-L-rhamnopyranoside (11).

Figure 44:
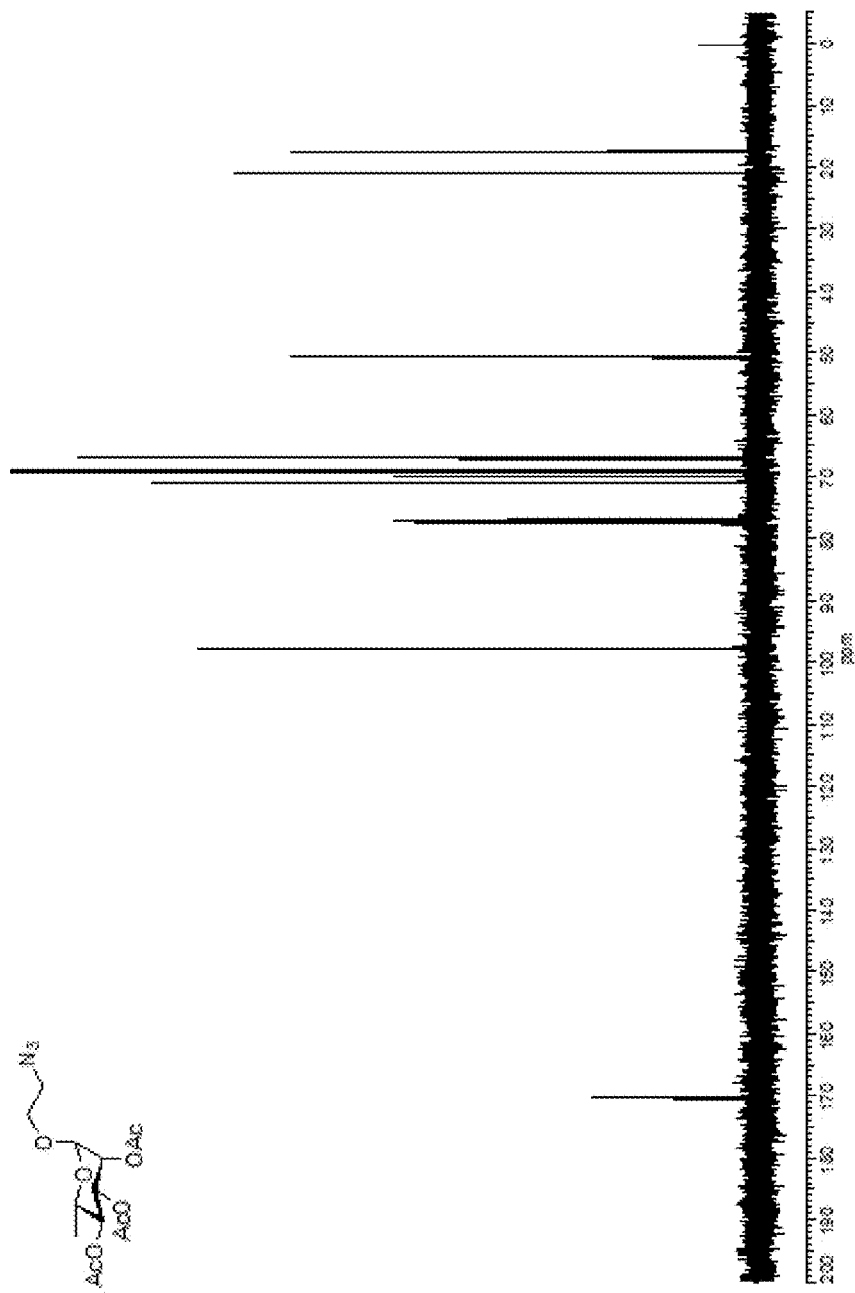
FIG. 44: $^{13}$C NMR of 2-Azidoethyl-2,3,4-Tri-O-acetyl-α-L-rhamnopyranoside (11).

FIG. 44: $^{13}$C NMR of 2-Azidoethyl-2,3,4-Tri-O-acetyl-α-L-rhamnopyranoside (11).

Figure 45:
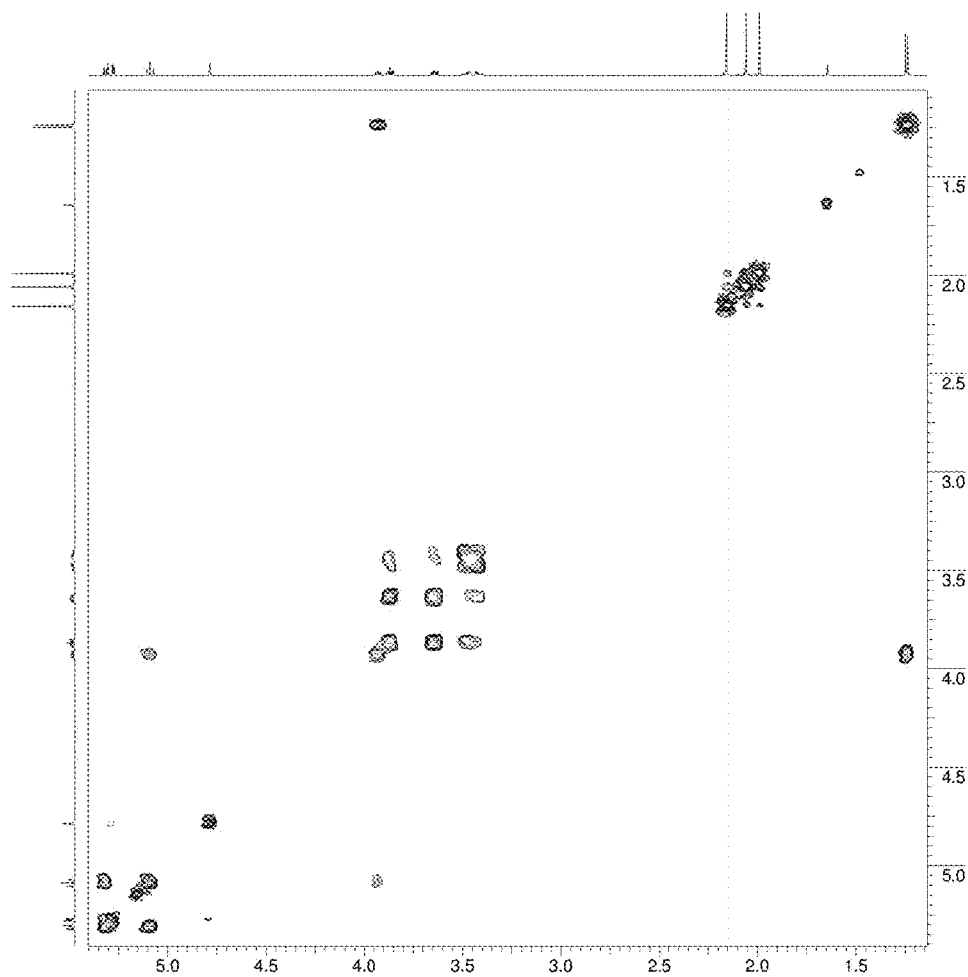
FIG. 45: $^1$H-gCosy of 2-Azidoethyl-2,3,4-Tri-O-acetyl-α-L-rhamnopyranoside (11).

FIG. 45: $^1$H-gCosy of 2-Azidoethyl-2,3,4-Tri-O-acetyl-α-L-rhamnopyranoside (11).

Figure 46:
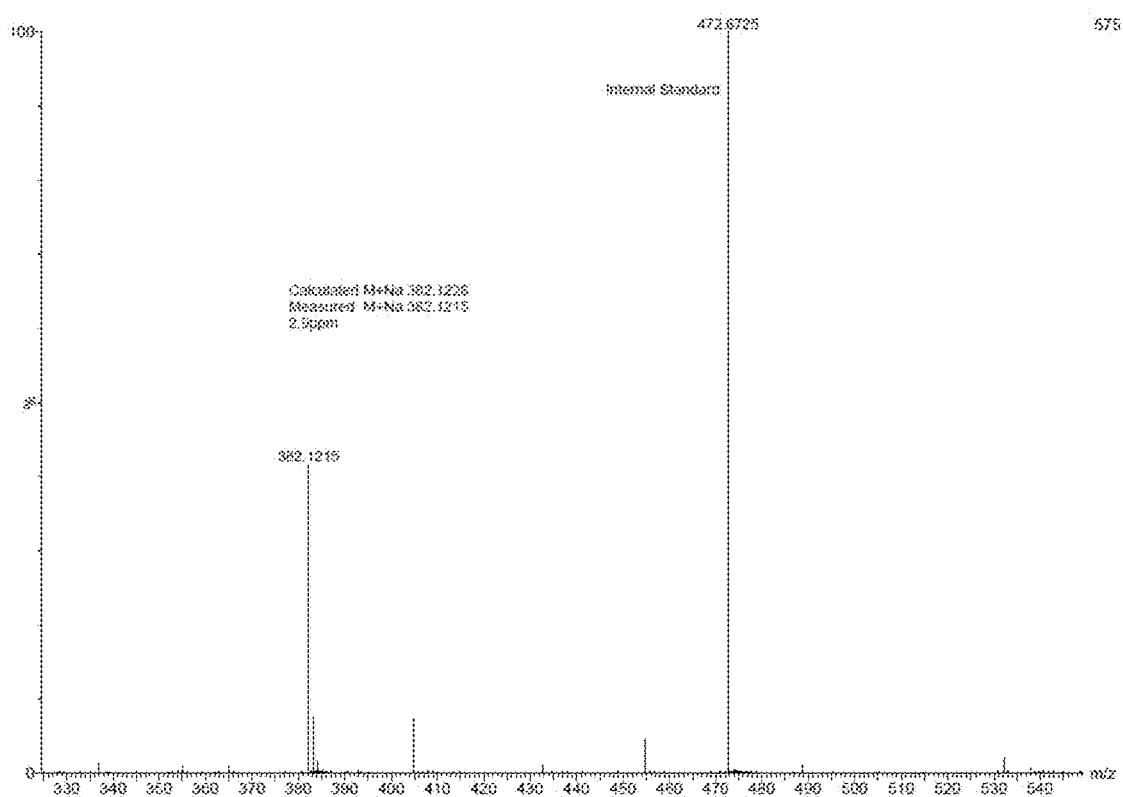
FIG. 46: HRMS of 2-Azidoethyl-2,3,4-Tri-O-acetyl-α-L-rhamnopyranoside (11).

FIG. 46: HRMS of 2-Azidoethyl-2,3,4-Tri-O-acetyl-α-L-rhamnopyranoside (11).

Figure 47:
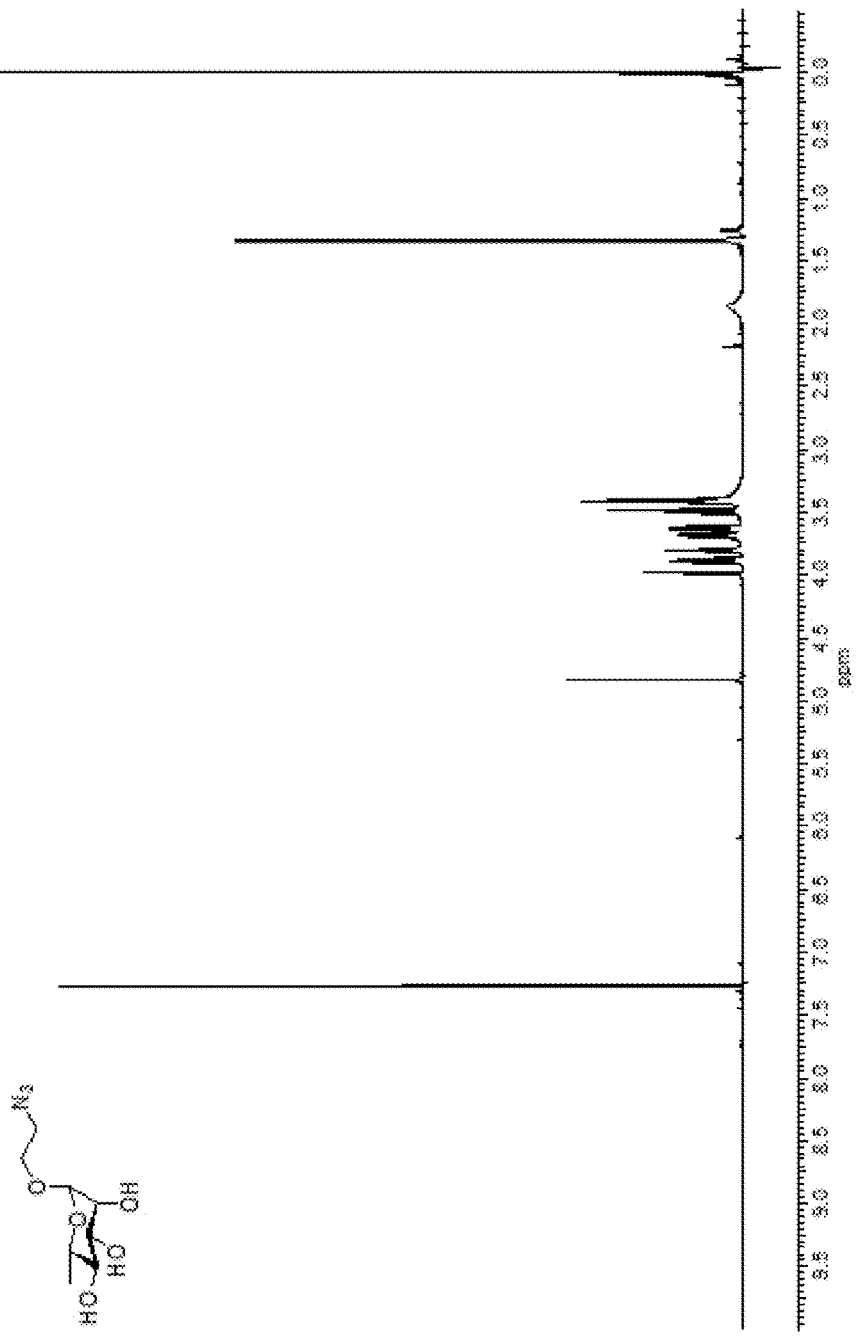
FIG. 47: $^1$H NMR of 2-Azidoethyl α-L-rhamnopyranoside (12).

FIG. 47: $^1$H NMR of 2-Azidoethyl α-L-rhamnopyranoside (12).

Figure 48:
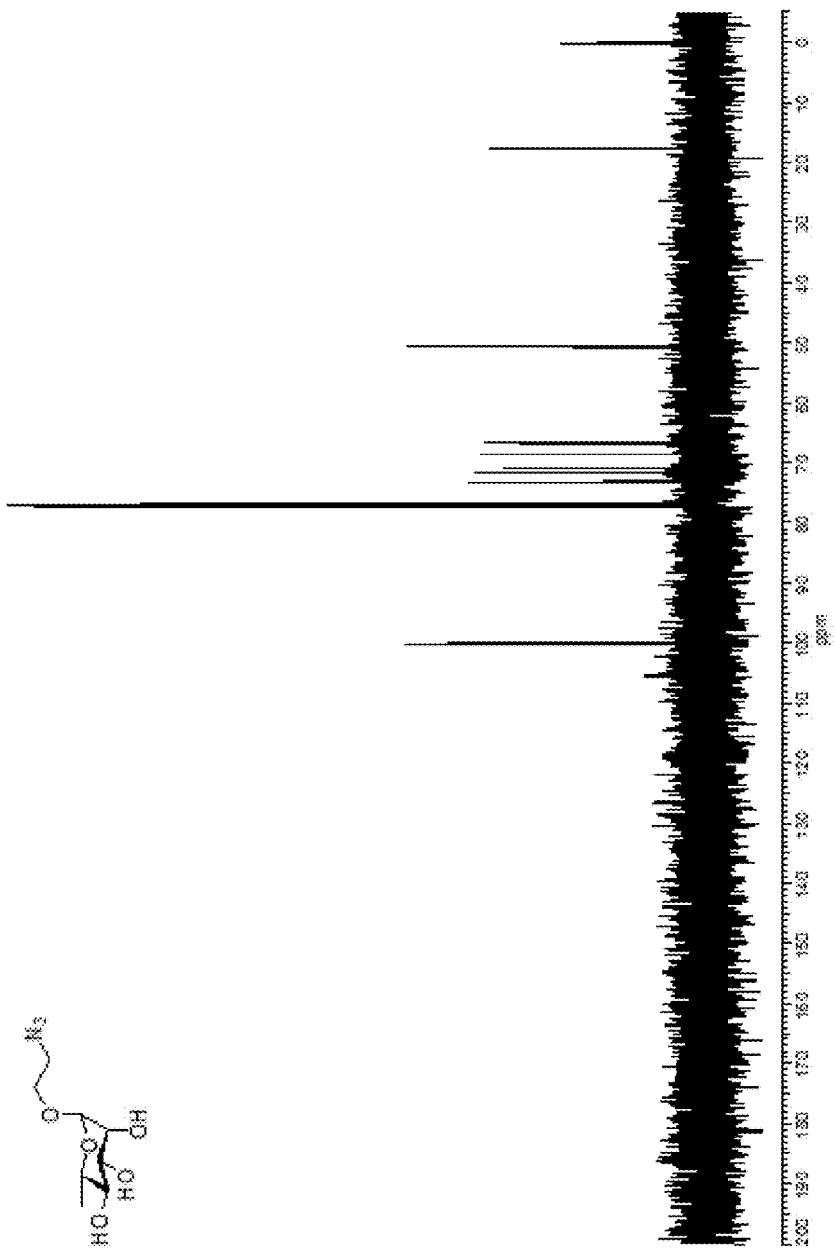
FIG. 48: $^{13}$C NMR of 2-Azidoethyl α-L-rhamnopyranoside (12).

FIG. 48: $^{13}$C NMR of 2-Azidoethyl α-L-rhamnopyranoside (12).

Figure 49:
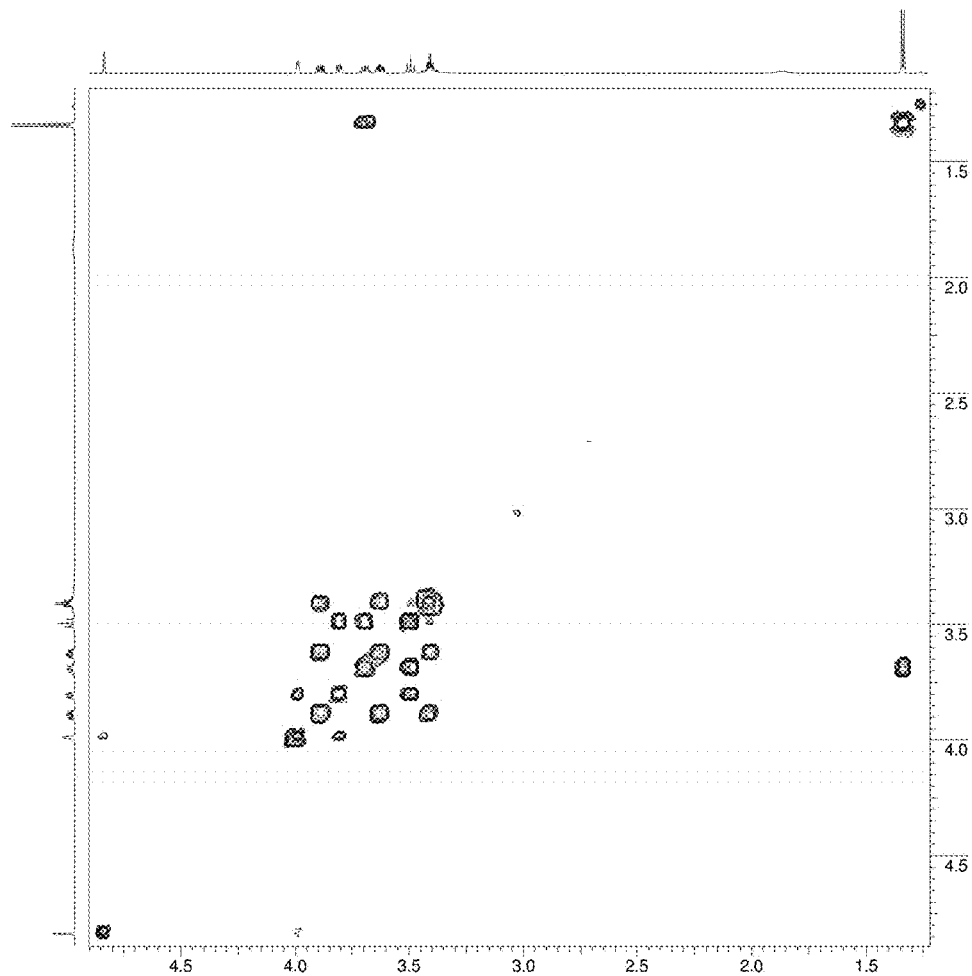
FIG. 49: $^1$H-gCosy of 2-Azidoethyl α-L-rhamnopyranoside (12).

FIG. 49: $^1$H-gCosy of 2-Azidoethyl α-L-rhamnopyranoside (12).

Figure 50:
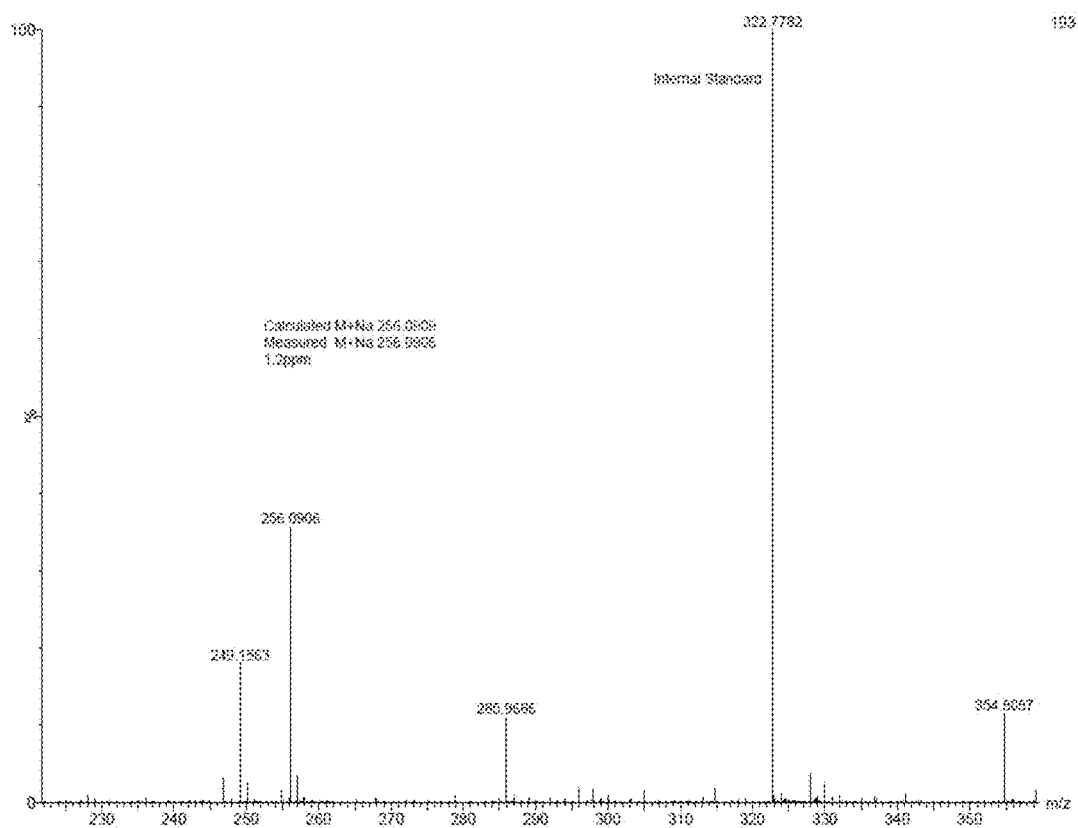
FIG. 50: HRMS of 2-Azidoethyl α-L-rhamnopyranoside (12).

FIG. 50: HRMS of 2-Azidoethyl α-L-rhamnopyranoside (12).

Figure 51:
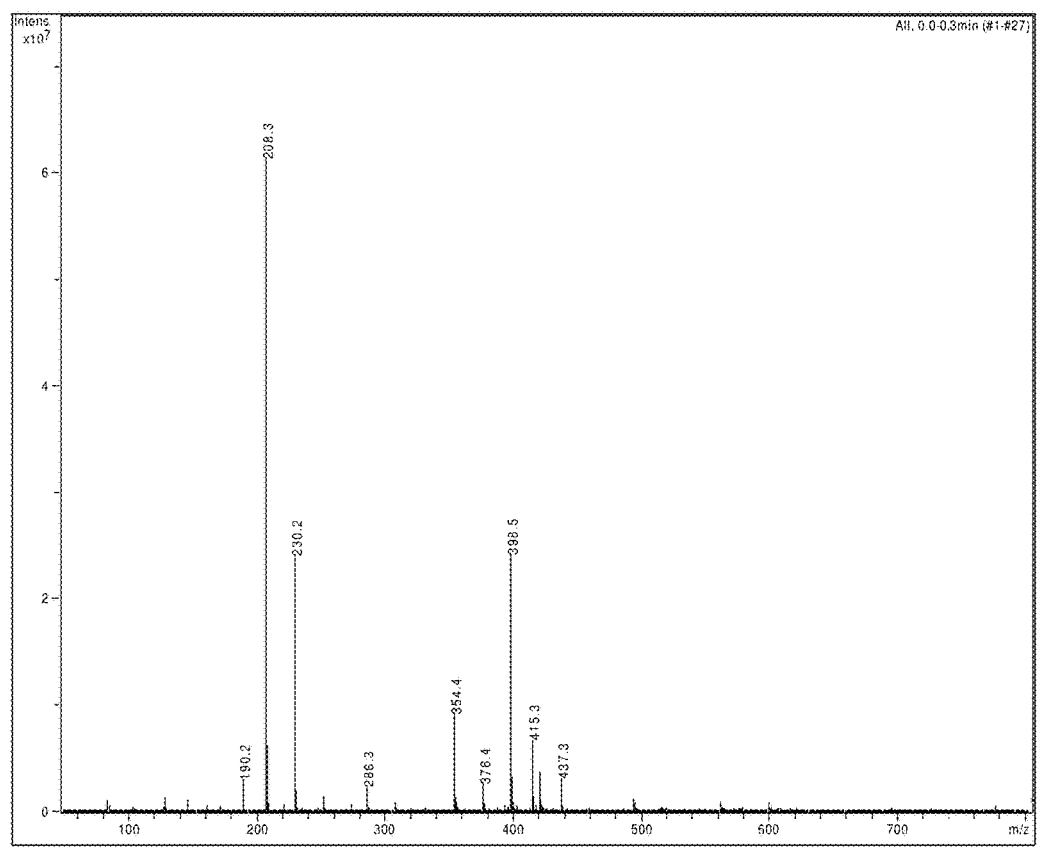
FIG. 51: ESI MS of 2-Aminoethyl α-L-rhamnopyranoside (13).

FIG. 51: ESI MS of 2-Aminoethyl α-L-rhamnopyranoside (13).

Example 8

Figure 52:
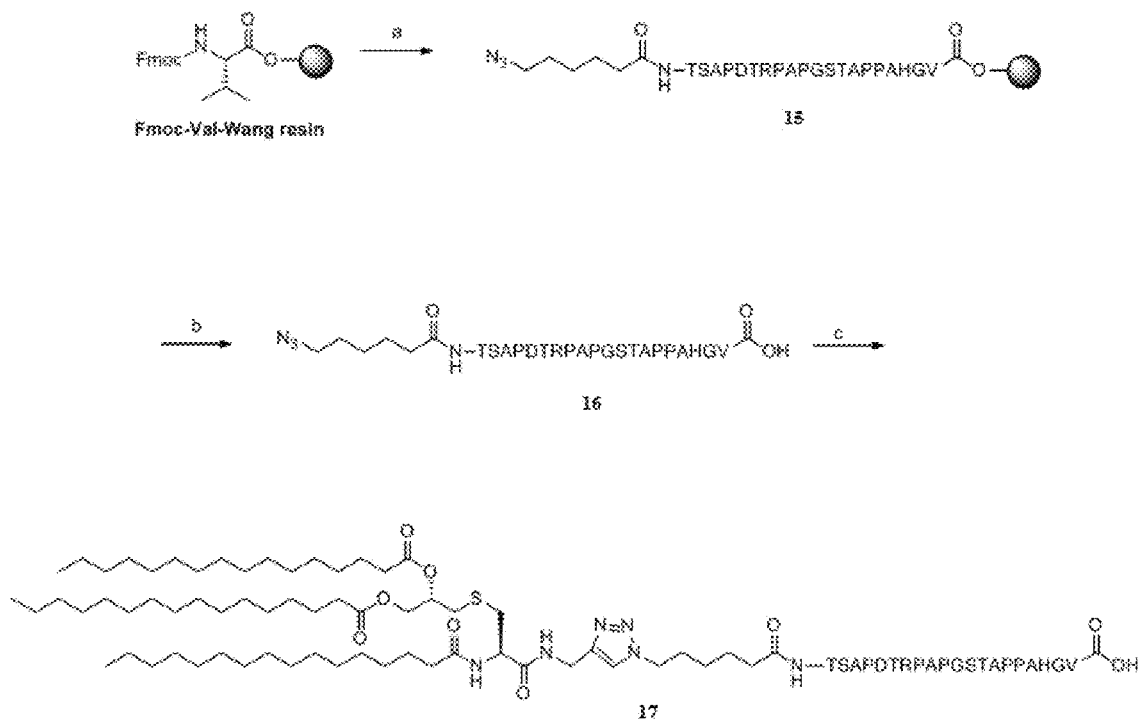
FIG. 52: Scheme showing the synthesis of Pam$_3$Cys-MUC-1 VNTR conjugate (17) [SEQ ID NOS: 11, 11 and 12], respectively, in order of appearance.

A 20-amino acid (TSAPDTRPAPGSTAPPAHGV [SEQ ID NO: 5]) tandem repeat of MUC1 was synthesized. The peptide was modified with a terminal azido group in order to make a 'click' conjugation to the Pam$_3$Cys alkyne with a terminal azido group. The peptide was synthesized by a Fmoc strategy on an Omega 396 synthesizer (Advanced ChemTech, Louisville, Ky.) starting from preloaded Fmoc-L-Val Wang resin using solid-phase chemistry, as shown in FIG. 52.

The peptide synthesis was performed by coupling amino acid esters of HOBt using DIC as the coupling agent. A six-fold excess of N$^α$-Fmoc amino acid esters of HOBt in NMP were used in the synthesis. A 1:1 ratio of amino acid to DIC was used in all the coupling reactions. Deprotection of N$^α$-Fmoc group was accomplished by treatment with piperidine in DMF. After the synthesis was complete, the peptide was cleaved from the solid support and deprotected using a modified reagent K cocktail consisting of TFA-thioanisole-ethanedithiol-water-phenol (88:3:5:2:2). The cocktail mixture was filtered through a Quick Snap column, purified by C18 reverse phase HPLC, and lyophilized to afford composition (16) as a white powder.

Conjugation of the composition (16) (1 eqv) with the composition (6) (3 eqv) in the presence of copper(I) iodide (12 eqv), tris [(1-benzyl-1H-1,2,3-triazol-4-yl)methyl] amine (TBTA) (3 eqv), diisopropyl ethyl amine (DIEA) (12 eqv) and sodium ascorbate (12 eqv) in H$_2$O-THF-DMF (1:1:2) as solvent at 20° C. thus afforded the target, Pam$_3$Cys-MUC1 VNTR conjugate (17), after 16 h.

Composition (17) was purified by neutralization by 7.5% citric acid solution followed by extraction with chloroform. Evaporation of the chloroform extract afforded the composition (17) as a white solid.

Synthesis of Azide (16)

The peptidazide was synthesized by Fmoc strategy on an Omega 396 synthesizer (Advanced ChemTech, Louisville, Ky.) using solid phase chemistry. The peptide synthesis was performed by coupling amino acid esters of HOBt using DIC as the coupling agent starting with a preloaded Fmocvalinyl-Wang resin. A six-fold excess of $N^\alpha$-Fmoc amino acid esters of HOBt in NMP were used in the synthesis. A 1:1 ratio of amino acid to DIC was used in all the coupling reactions. Deprotection of $N^\alpha$-Fmoc group was accomplished by treatment with 25% piperidine in dimethylformamide twice; first for 5 minutes and then a second time for 25 minutes to afford composition (15).

After the synthesis was complete, the peptide was cleaved from the solid support and deprotected using a modified reagent K cocktail consisting of 88% TFA, 3% thioanisole, 5% ethanedithiol, 2% water, and 2% phenol. 4 mL of cleavage cocktail was added to the dried peptide-resin in a 15 mL glass vial blanketed with nitrogen. Cleavage was carried out for 2.5 hrs with gentle magnetic stirring. At the end cleavage time, the cocktail mixture was filtered on a Quick-Snap column. The filtrate was collected in 20 mL ice-cold butane ether. The peptide was allowed to precipitate for an hour at $-200°$ C., centrifuged, and washed twice with ice-cold methyl-t-butyl ether. The precipitate was dissolved in 25% acetonitrile and lyophilized to complete dry powder affording composition (16). Quality of peptides was analyzed by analytical reverse phase HPLC and MALDI-TOF (matrix assisted laser desorption ionization time-of-flight) mass spectrometer, model 4800 from Applied Biosystems. HR-MALDI-MS: [M+H] m/z calcd for $C_{86}H_{136}N_{28}O_{29}$, 2026.17. found, 2026.137.

Synthesis of Lipopeptide (17)

CuI (134 µg, 0.54 µmol) and TBTA (0.857 mg, 1.62 µmol) were dissolved in $H_2O$-THF (1:1, 0.40 mL) and to it sodium ascorbate (0.80 mg, 4.04 µmol) was added and stirred for 5 minutes. Composition (6) (1.27 mg, 1.35 µmol) in THF (0.40 mL) was added to the reaction mixture and stirred for 15 minutes followed by the addition of a solution of composition (16) (1 mg, 0.49 µmol) in $H_2O$-DMF (1:3, 0.4 mL). The reaction mixture was stirred at 20° C. under $N_2$ atmosphere for 16 h. The reaction mixture was concentrated, dissolved in $CHCl_3$, washed with 7.5% aqueous citric acid solution, dried over sodium sulfate, and the solvent was evaporated to afford composition (17) as a white solid (1.47 mg, 100%). HR-MALDI-MS: [M+H] m/z calcd for $C_{143}H_{242}N_{30}O_{35}S$, 2972.78. found 2972.828.

Figure 53:
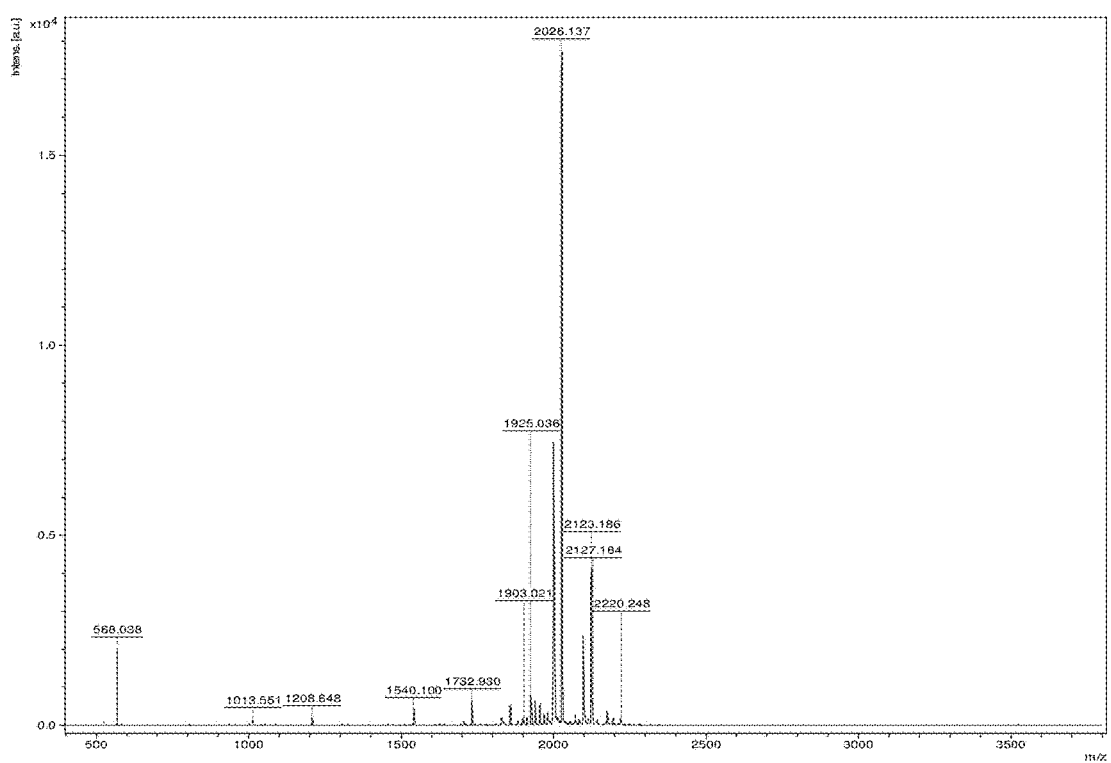
FIG. 53: HRMS (MALDI-TOF) spectrum of peptide (16).
Figure 54:
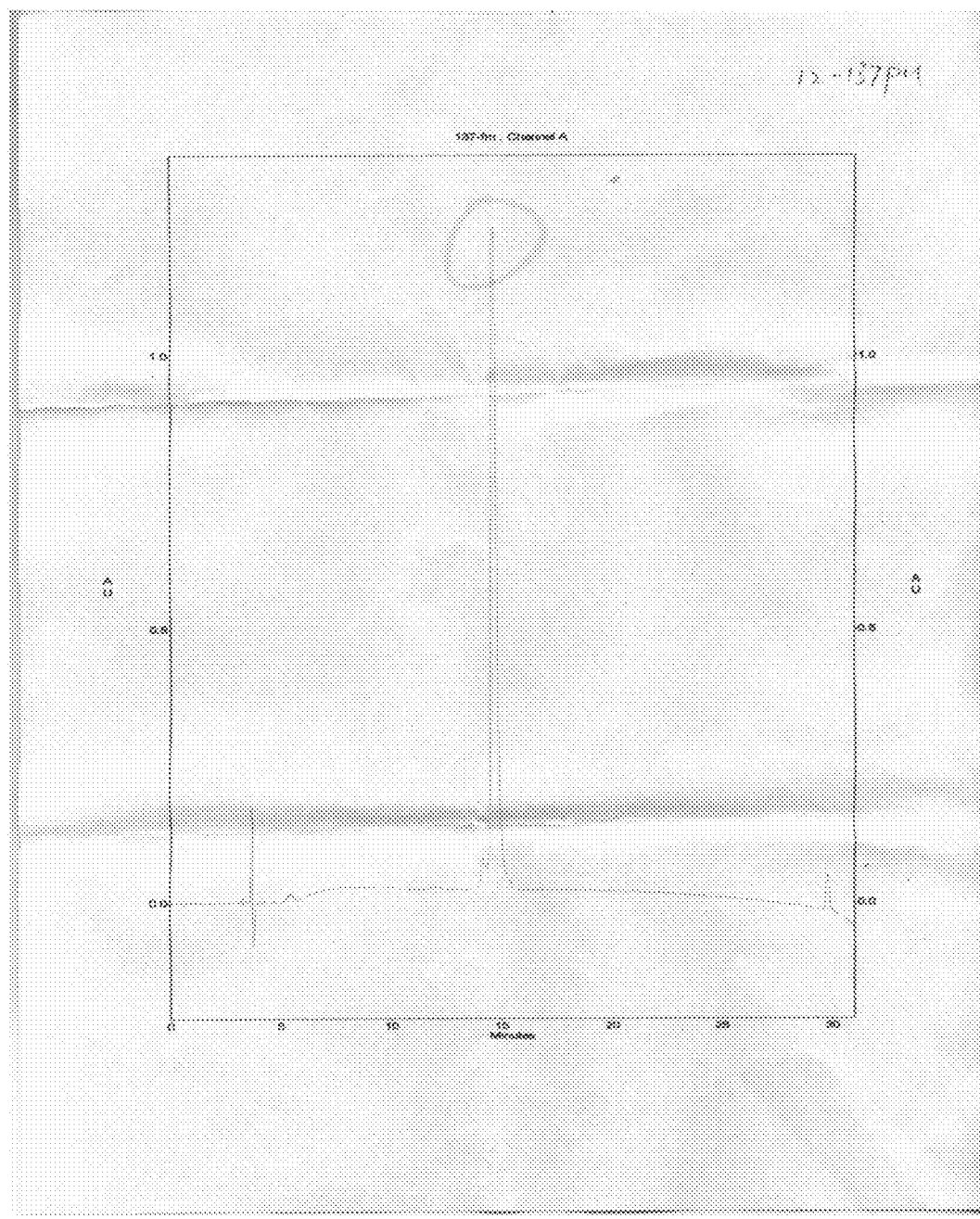
FIG. 54: HPLC trace of peptide (16).

FIGS. 53 and 54 show the HRMS (MALDI-TOF) spectrum and HPLC trace, respectively, of peptide (16).

Figure 55:
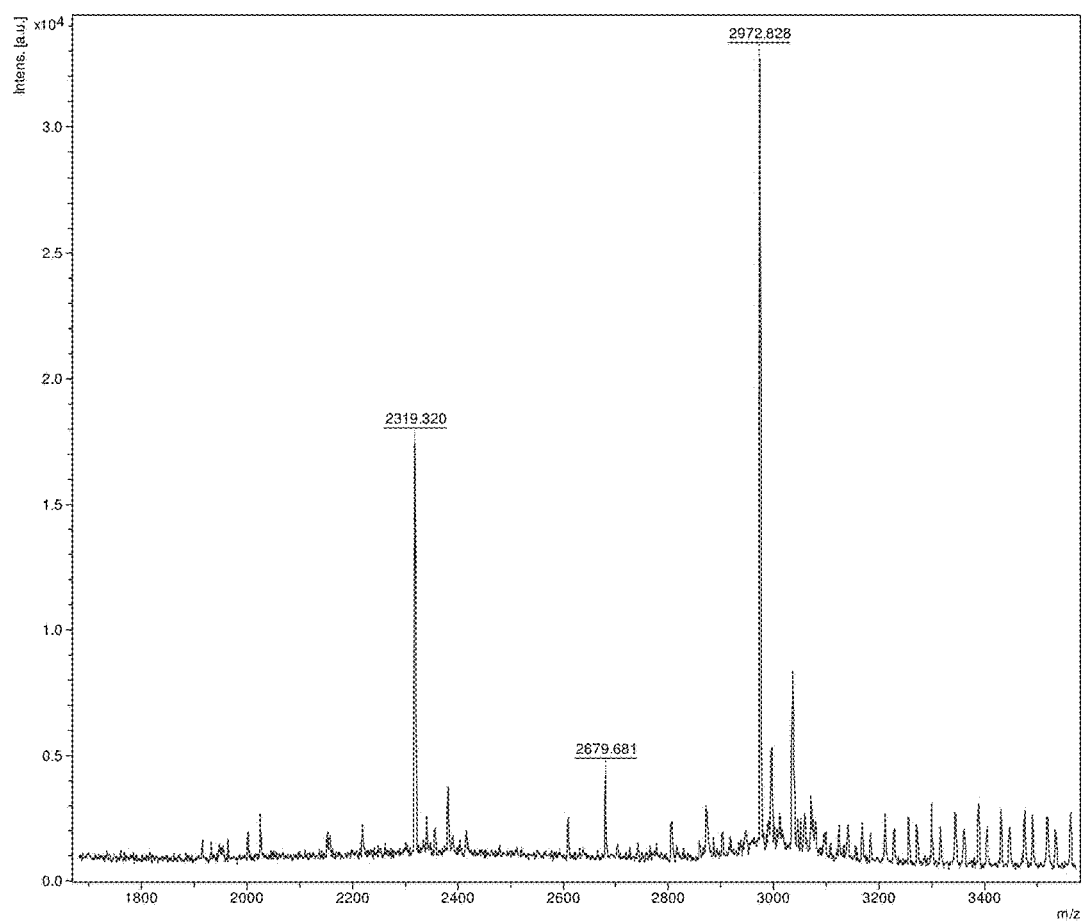
FIG. 55: HRMS (MALDI-TOF) spectrum of lipopeptide (17).

FIG. 55 shows the HRMS (MALDI-TOF) spectrum of lipopeptide (17).

Example 9

Figure 56:
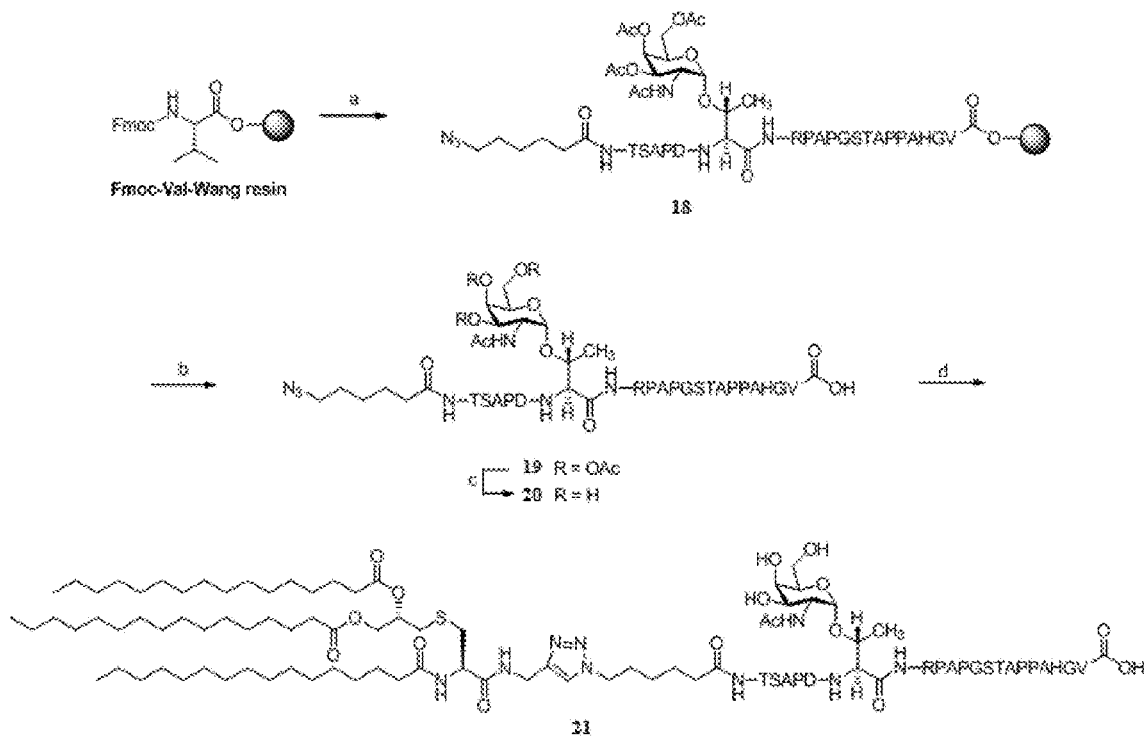
FIG. 56: Synthesis of Pam$_3$Cys-MUC-1 VNTR conjugate (21) [SEQ ID NOS: 13, 14 15], respectively, in order of appearance.

A 20-amino acid (TSAPDT(Tn)RPAPGSTAPPAHGV [SEQ ID NO: 6]) tandem repeat of MUC1 which included the PD(α-GalNAc-O-T)R epitope was synthesized. The glycopeptides was modified with a terminal azido group in order to make a 'click' conjugation to the $Pam_3Cys$ alkyne. The glycopeptides azide was synthesized by Fmoc strategy on an Omega 396 synthesizer (Advanced ChemTech, Louisville, Ky.) starting from preloaded Fmoc-L-Val Wang resin using solid-phase chemistry, as shown in FIG. 56.

The peptide synthesis was performed by coupling amino acid esters of HOBt using DIC as the coupling agent. A six-fold excess of $N^\alpha$-Fmoc amino acid esters of HOBt in NMP were used in the synthesis. A 1:1 ratio of amino acid to DIC was used in all the coupling reactions. Deprotection of $N^\alpha$-Fmoc group was accomplished by treatment with piperidine in DMF. After the synthesis was complete, the peptide was cleaved from the solid support and deprotected using a modified reagent K cocktail consisting of TFA-thioanisole-ethanedithiol-water-phenol (88:3:5:2:2). The cocktail mixture was filtered through a Quick Snap column, purified by C18 reverse phase HPLC and lyophilized to afford composition (19).

The acetyl groups in composition (19) were deprotected by treatment with 6 mmol sodium methoxide in methanol. The product was purified by Bio-Gel (P-2, fine 45-90 µm) size exclusion chromatography using deionized water as solvent. Lyophilization of the fractions afforded composition (20) (100%) as a white powder. Conjugation of the composition (19) (1 eqv) with the composition (6) (3 eqv) in the presence of copper(I) iodide (12 eqv), tris [(1-benzyl-1H-1,2,3-triazol-4-yl)methyl] amine (TBTA) (3 eqv), diisopropyl ethyl amine (DIEA) (12 eqv) and sodium ascorbate (12 eqv) in $H_2O$-THF-DMF (1:1:2) as solvent at 20° C. thus afforded the target, $Pam_3Cys$-MUC1 VNTR-TACA conjugate (21), after 16 h. Composition (21) was purified by neutralization by 7.5% citric acid solution followed by extraction with chloroform. Evaporation of the chloroform extract afforded the composition (21) as light yellow solid.

Synthesis of Azide (20)

Composition (19) (5 mg, 2.24 µmol) was dissolved in 2 mL of dry methanol. 12 µL of freshly prepared 1 M sodium methoxide was added to the mixture and the reaction mixture was stirred at ambient temperature under $N_2$ atmosphere for 3 h. The reaction mixture was neutralized with solid carbon dioxide. The reaction mixture was concentrated and purified by Bio-Gel (P-2, fine 45-90 µm) size exclusion chromatography using deionized water as solvent. Lyophilization of the eleutants afforded composition (20) as a white powder (4.7 mg, 100%). HR-MALDI-MS: [M+H] m/z calcd for $C_{94}H_{149}N_{29}O_{34}$, 2229.09. found 2026.336.

Synthesis of Glycolipopeptide (21)

CuI (134 µg, 0.54 µmol) and TBTA (0.857 mg, 1.62 µmol) were dissolved in $H_2O$-THF (1:1, 0.40 mL) and to it sodium ascorbate (0.80 mg, 4.04 µmol) was added and stirred for 5 minutes. Composition (6) (1.27 mg, 1.35 µmol) in THF (0.40 mL) was added to the reaction mixture and stirred for 15 minutes followed by the addition of a solution of composition (20) (1 mg, 0.45 µmol) in $H_2O$-DMF (1:3, 0.4 mL). The reaction mixture was stirred at 20° C. under $N_2$ atmosphere for 16 h. The reaction mixture was concentrated, dissolved in $CHCl_3$, washed with 7.5% aqueous citric acid solution, dried over sodium sulfate, and the solvent was evaporated to afford composition (21) as a light yellow solid (1.9 mg, 100%). HR-MALDI-MS: [M+H] m/z calcd for $C_{151}H_{255}N_{31}O_{40}S$, 3175.86. found 3175.809.

Figure 57:
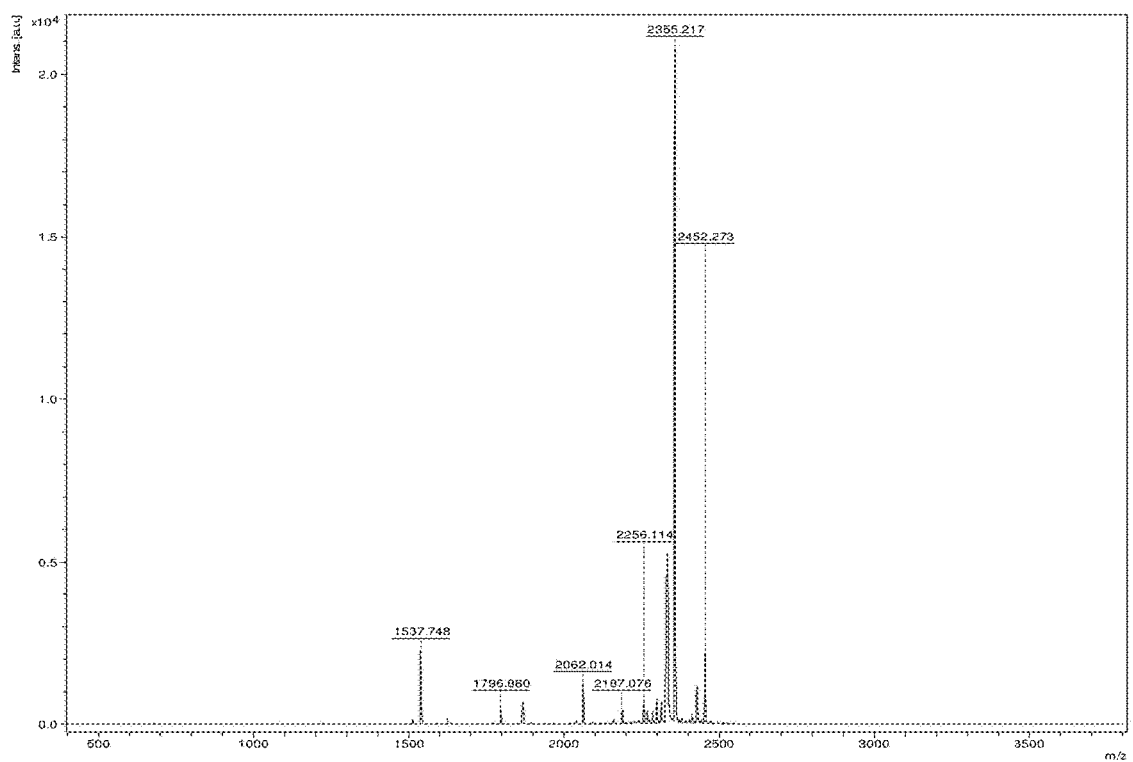
FIG. 57: HRMS (MALDI-TOF) of glycopeptide (19).
Figure 58:
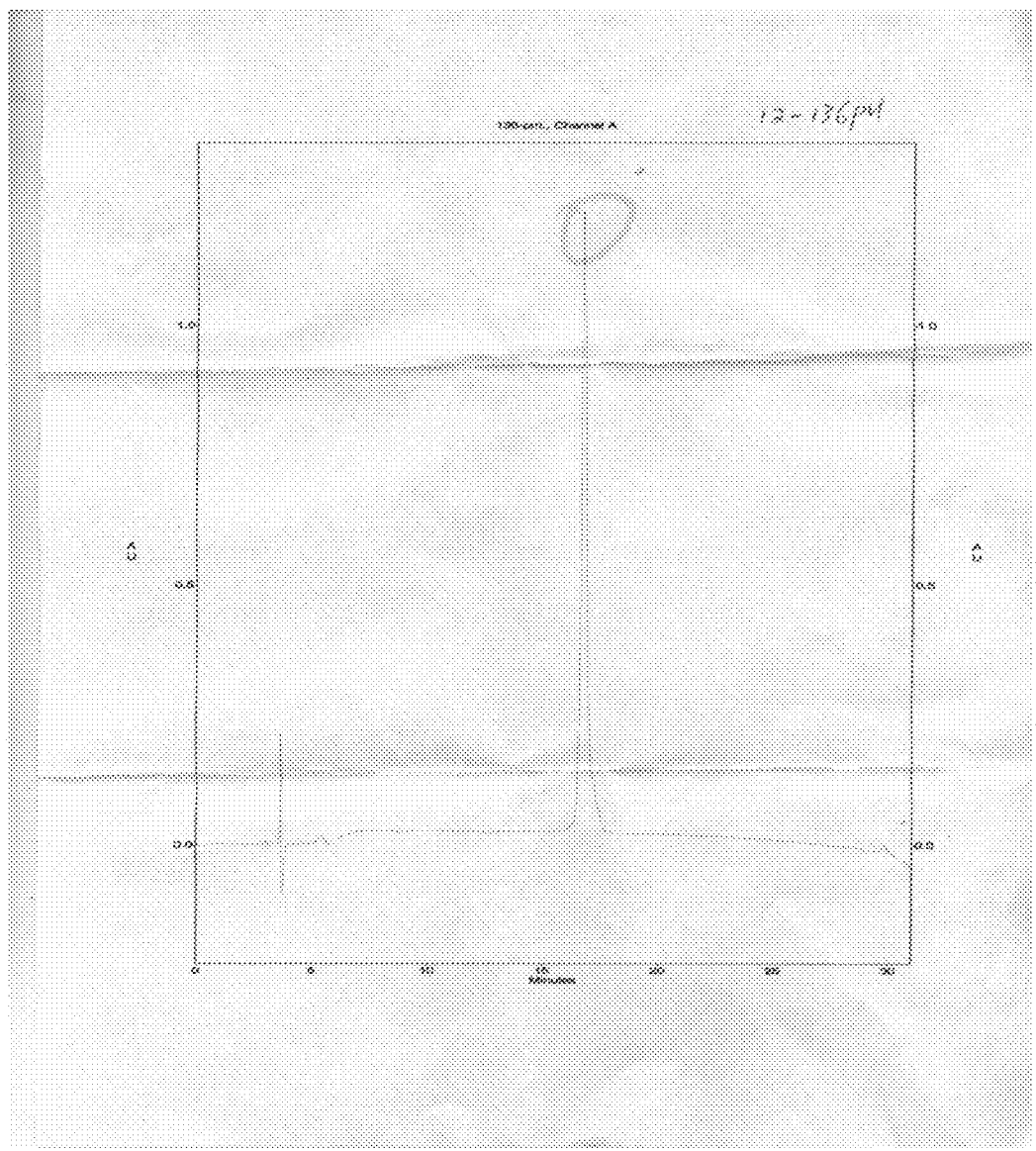
FIG. 58: HPLC trace of glycopeptide (19).

FIGS. 57 and 58 show the HRMS (MALDI-TOF) spectrum and HPLC trace of glycopeptide (19).

Figure 59:
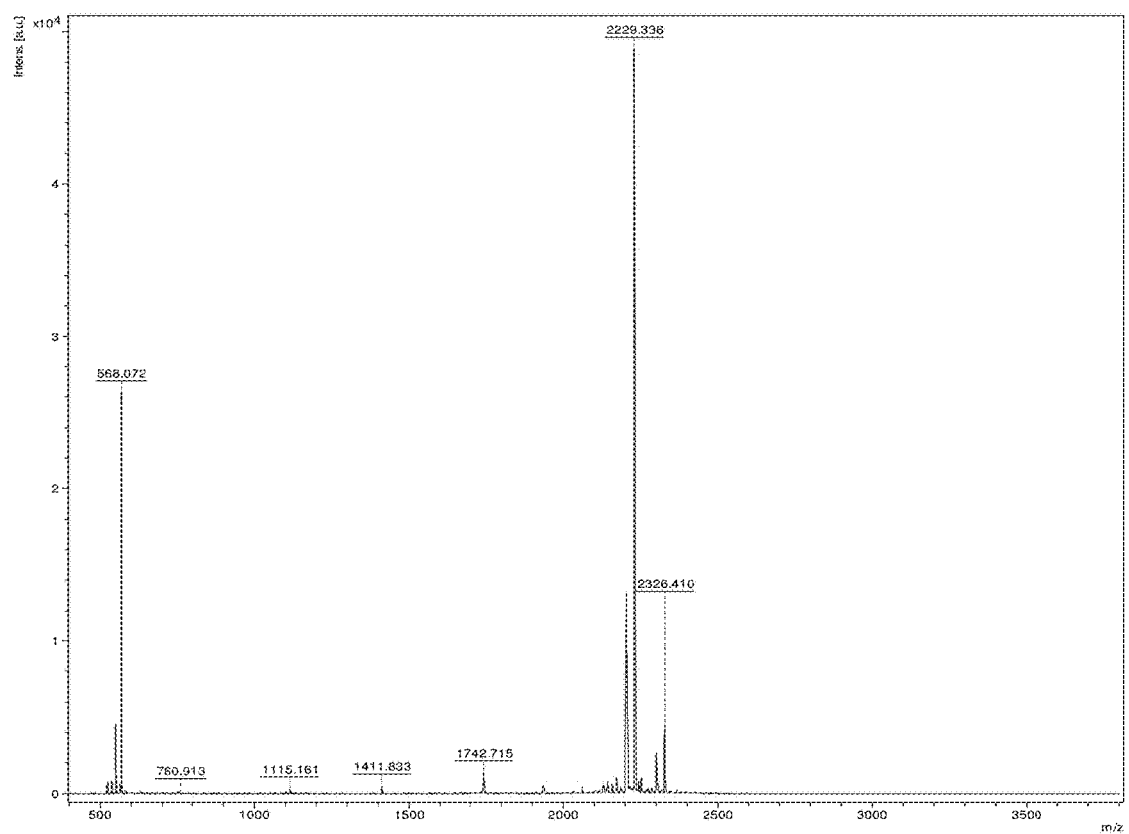
FIG. 59: HRMS (MALDI-TOF) of glycopeptide (20).

FIG. 59 is the HRMS (MALDI-TOF) spectrum of glycopeptides (20).

Figure 60:
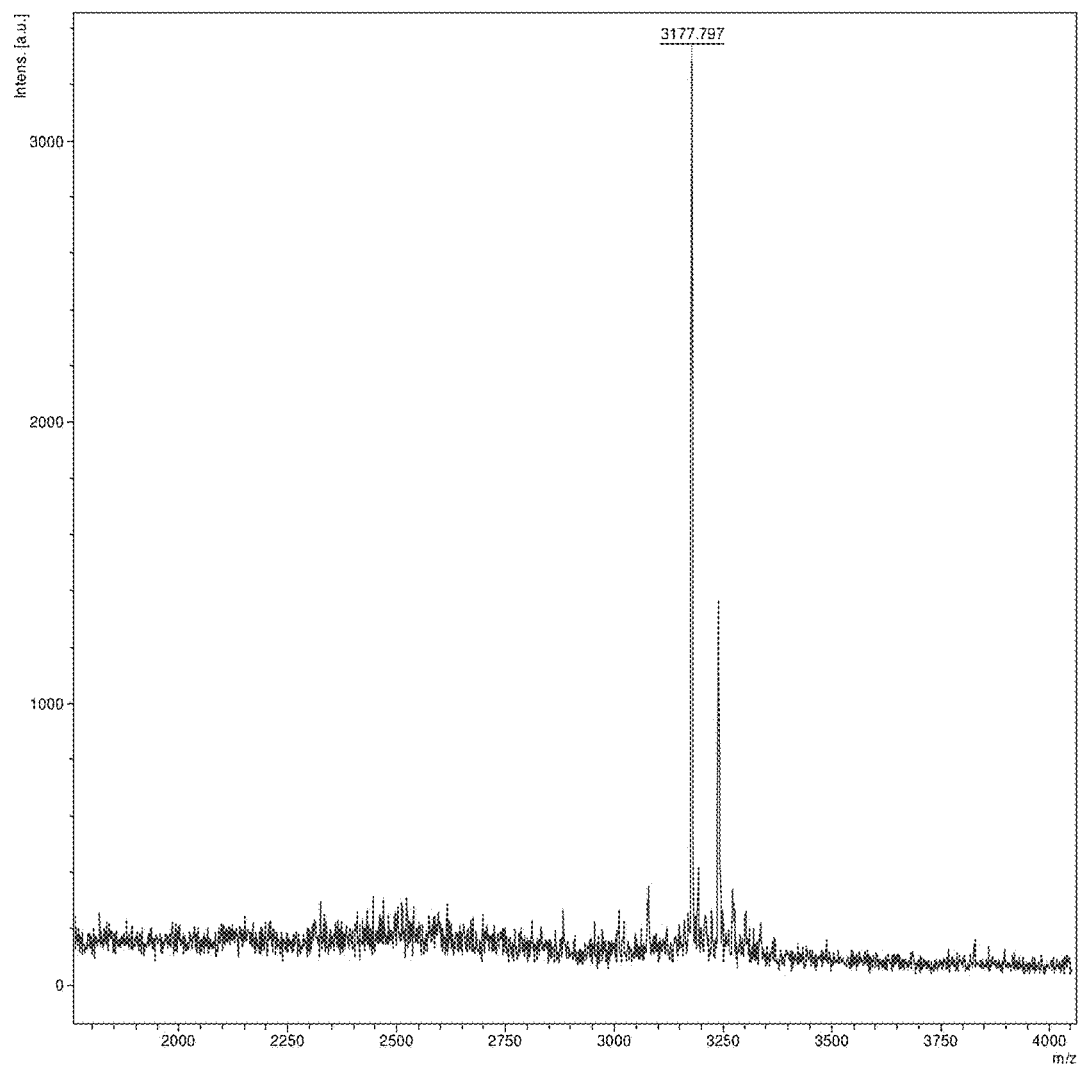
FIG. 60: HRMS (MALDI-TOF) of Pam$_3$Cys-MUC-1 VNTR conjugate (21).

FIG. 60 is the HRMS (MALDI-TOF) spectrum of $Pam_3Cys$-MUC-1 VNTR conjugate (21).

Methods of Use

Also provided herein is a method for eliciting an immune response against a cancer cell surface antigen in a subject in need thereof. The method comprises administering to the subject an antigen-liposome-xenoantigen vaccine composition in sufficient dose to elicit the immune response to the cancer cell surface antigen, wherein the antigen-liposome-xenoantigen vaccine composition comprises the cancer cell surface antigen and a liposome.

In certain embodiments, the cancer cell surface antigen is expressed only in cancer cells in the subject, such that the immune response specific for the antigen would not attack healthy tissues/organs of the subject. In certain embodiments, the antigen that is expressed on the cancer cell surface is a mutant protein present only on cancer cells, and the immune response is specific for the mutant protein epitope comprising the mutation. The mutation can be a protein mutation, or abnormal sugar or lipid structures on cancer cell surface.

Example 10

T-Cell Proliferation Study

Immunization

One female BALB/c mouse (6-8 weeks old, The Jackson Laboratory) was primed (day 0) and boosted three time (days 14, 28, and 42) with 100 μL subcutaneous injections of an equivolume emulsion of the MUC1-Tn conjugate (8) (prepared in phosphate buffer saline-PBS) and sigma adjuvant system (SAS) (50 μg of peptide per mouse, each injection).

Preparation of Anti-Rha Antibodies

The Rha-Ficoll and the Rha-OVA immunized mice were bled on day 66 and the sera was pooled. IgG fractions from each pool were prepared by precipitation at 40% saturation of ammonium sulfate. The mixtures were incubated overnight and centrifuged at 10000×g for 10 minutes and then resuspended in 0.5 mL water. The antibody solutions were concentrated and buffer was changed twice with PBS using an Ultrafree 0.5 centrifugal filter device (Millipore, Billerica, Mass.) having a molecular cut off of 50000 D. Absorbances of the antibody solutions were recorded at 280 nm to calculate the concentrations and the anti-Rha antibody solutions generated and isolated from the Rha-Ficoll and the Rha-OVA immunized mice were each diluted to 1.0 mg/mL.

Preparation of Spleen Cell Suspensions and Assay Setup

On day 49, the mouse was sacrificed and the spleen was removed and placed in 5 mL of freshly prepared spleen cell culture medium (DMEM with 10% fetal calf serum). Single cell suspension was prepared using modified sterile glass homogenizers. The cells were washed three times with culture medium and brought to $5\times10^6$ cells/mL. 100 μL of the spleen cell suspensions were added to 96 well plates ($5\times10^5$ cells per well). The dendritic cell (DC) suspension cultured from the bone marrow of a BALB/c mouse was pulsed with the antigen by incubating with the Rha-displaying MUC1-Tn liposomes at antigen concentrations of $8.8\times10^{-3}$-1.1 μg/mL at 37° C. for 4 h together with anti-Rha antibodies generated from either Rha-Ficoll or Rha-OVA immunized mice sera (5 μCi/mL, 25 μL per well) and incubated overnight at 37° C. The cells were harvested on glass-fiber filters and incorporation was determined by measurements on a Top Count scintillation counter.

Immunizations

The 20 female BALB/c mice used for this study were divided into four groups A1, A2, B1, and B2, containing 5 mice each. Groups A1 and B1 served as the control groups and were not immunized. Groups A2 and B2 were injected subcutaneously (day 0) with a 100 μL subcutaneous injections Rha-Ficoll/Alum on days 14, 28, 42, and 56 (100 μg of Rha-Ficoll per mouse, each boost). The mice in each group A1, A2, B1, and B2 were bled on day 66 and the collected sera were tested for anti-Rha antibodies.

ELISA for Measuring Anti-Rha Antibody Titers 96 well plates (Immulon 4 HBX) were coated with Rha-BSA conjugate (6) (2 μg/mL) in 0.01 M PBS and incubated overnight at 4° C. The plates were washed 5 times with PBS containing 0.1% Tween-20. Blocking was achieved by incubating the plates for 1 h at room temperature with BSA in 0.01 M PBS (1 mg/mL). The plates were then washed 5 times and incubated for 1 h with serum dilutions in PBS. Unbound antibody in the serum was removed by washing and the plates were incubated for 1 h at room temperature with Horseradish Peroxidase (HRP) goat anti-mouse IgG+IgM (Jackson Immunoresearch Laboratories) diluted 5000 times in PBS/BSA. The plates were washed with TMB (3,3',5,5'-tetramethylbenzidine). One component HRP microwell substrate (Bio FX, Owings Mills, Md.) was added and allowed to react for 10 mins. Absorbances were recorded at 620 nm and were plotted against $\log_{10}$ [1/serum dilution].

Vaccinations

Vaccinations were performed on day 77. Two separate liposomal formulations were prepared with DPPC (80%), cholesterol (20%) and Pam$_3$Cys-MUC1-Tn (9) (2 nmol) (Pam$_3$Cys-MUC1-Tn liposomes) and DPPC (80%), cholesterol (10%), Rha-TEG-cholesterol 3 (10%) and Pam$^3$Cys-MUC1-Tn (9) (2 nmol) (Pam$_3$Cys-MUC1-Tn+Rha liposomes) in total lipid concentrations of 30 mmol Groups A1 and A2 were cavvinated with 100 μL subcutaneous injections of the Pam$_3$Cys-MUC1-Tn liposomes (2 nmol of peptide per mouse) and groups B1 and B2 were vaccinated with 100 μL subcutaneous injections of the Pam$_3$Cys-MUC1-Tn+Rha liposomes (2 nmol peptide per mouse). The mice were boosted on day 91 with either the Pam$_3$Cys-MUC1-Tn liposomes (groups A1 and A2, 2 nmol peptide per mouse) or the Pam$_3$Cys-MUC1-Tn+Rha liposomes (groups B1 and B2). The mice were bled on day 101 and the sera collected were tested for anti-MUC1-Tn and anti-Tn antibodies.

ELISA for Measuring Anti-MUC1-Tn Antibody Titers

96 Well plates (Immulon 4 HBX) were coated with MUC1-Tn conjugate (8) (15 μL/mL) in 0.01 M PBS and incubated overnight at 4° C. The ELISA was continued as described above.

ELISA for Measuring Anti-Tn Antibody Titers

96 Well plates (Immulon 4 HBX) were coated with Tn-BSA conjugate (15 μL/mL) in 0.01 M PBS and incubated overnight at 4° C. The ELISA was continued as described above.

Anti-MUC1-Tn Antibody Subclass Identification

96 Well plates (Immulon 4 HBX) were coated with MUC1-Tn conjugate (8) (15 μL/mL) in 0.01 M PBS and incubated overnight at 4° C. The plates were washed 4 times with PBS containing 0.1% Tween-20. Blocking was achieved by incubating the plates for 1 h at room temperature with BSA in 0.01 M PBS (1 mg/mL). The plates were then washed 4 times and incubated for 1 h with 1/100 serum dilution in PBS. Unbound antibody in the serum was removed by washing and the plates were incubated overnight at 4° C. with subclass specific (IgG1, IgG2s, IgG2b, IgG3, 1gA, and IgM) rabbit anti-mouse antibody (Zymed Laboratories mouse monoAb-ID kit). The plates were washed and incubated with HRP-goat anti-rabbit IgG (H+L) for 1 h at room temperature. The plates were washed and ABTS substrate buffer (diluted 50 times) was added and allowed to react for 30 min. Absorbances were recorded at 405 nm and compared for each antibody subclass in each group.

ELISA for Competitive Binding with Free MUC1-Tn

A 96-well plate (Immulon 4 HBX) was coated with MUC1-Tn conjugate (8) (15 µL/mL) in PBS and incubated overnight at 4° C. The plate was washed 5 times with PBS containing 0.1% Tween-20. Blocking was achieved by incubating the plate for 1 h at room temperature with BSA in M PBS (1 mg/mL). The plate was then washed 5 times and incubated for 1 h with serum dilutions of 1/100 in PBS with or without prior mixing with varying concentrations of free MUC1-Tn (8) from 0, $10^{-5}$, $10^{-4}$, $10^{-3}$ M in PBS. Unbound antibody in the serum was removed by washing and the plate was incubated for 1 h at room temperature with Horseradish Peroxidase (HRP) goat anti-mouse IgG+IgM (secondary antibody) diluted 5000 times in PBS/BSA. The plate was washed and TMB 1 component HRP microwell substrate was added and allowed to react for 10 mins. Absorbances were recorded at 620 nm and were plotted against $\log_{10}$ [1/free Tn concentration].

Tumor Cell Staining

U266 cells (American Type Culture Collection, Manassas, Va.), were cultured in RPMI 1640 with 15% fetal calf serum (FCS). Cells were stained with purified mouse anti-human MUC1 antibodies (CD227, 0.5 µg), non-immune BALB/c mice serum (1/5 dilution) and group B2 mice serum (1/5 dilution). The cells were then stained with FITC-conjugated goat anti-mouse IgG+IgM (0.5 µg) and fluorescence was quantified with a BD FACS Calibur.

Comparison of Anti-Rha Antibody Titers Generated Against Rha-Ficoll and Rha-OVA

Figure 36:
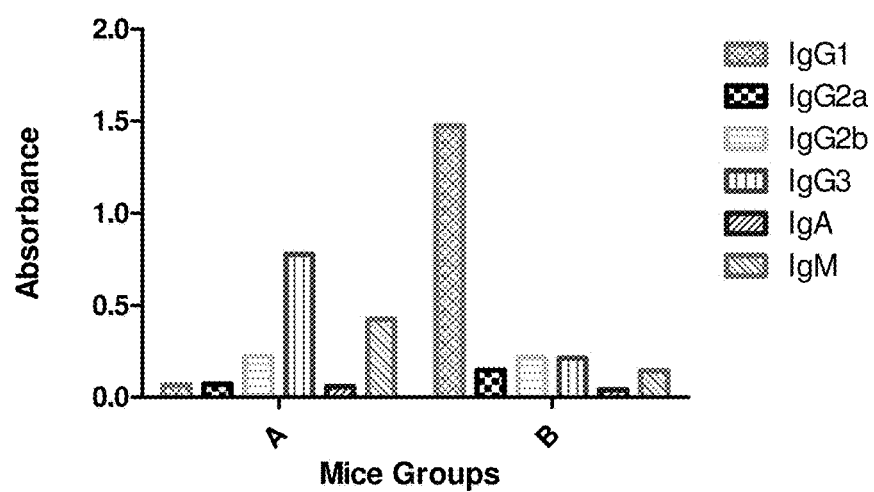
FIG. 36: Anti-Rha Antibody Isotype Titers after 4th Boost with Rha-Ficoll (group A) or Rha-OVA (group B) at 1/5 or 1/500 Serum Dilutions respectively.

Two groups of five female BALB/c mice each were immunized on day 0 with Rha-Ficoll/Alum adjuvant (group A) or Rha-OVA/complete Freund's adjuvant (CFA) (group B). The mice were boosted three more times on days 14, 28, and 42 with either Rha-Ficoll/Alum (group A) or rha-OVA/incomplete Freund's adjuvant (ICF) (group B). Sera were collected separately from groups A and B after the third boost and the anti-Rha antibodies in the sera from the two groups of mice were isotyped by screening against Rha-BSA. See FIG. 36. The results demonstrated the anti-Rha antibody titers in the Rha-OVA immunized micro groups were 100-fold higher than those from the Rha-Ficoll immunized mice. However, the isotype distribution confirmed that Rha-Ficoll and Rha-OVA produced the anti-Rha antibody subclasses in different proportions. Anti-Rha antibodies from Rha-OVA immunization were dominated by IgG1 (65%) while Rha-Ficoll immunization produced antibodies which comprised mainly IgG3 (48%) and IgM (25%). IgG1 and IgG3 act similarly in that they both stimulate high affinity FcγRI receptors which trigger responses from macrophages. However, IgG1 also stimulates low affinity FcγRIIB receptors which inhibit the signals from the FcγRI and B cell receptors thereby diminishing B-cell activity and immunogenicity of macrophages. The anti-Rha antibody isotypes from Rha-Ficoll immunized mice serum resembled those naturally occurring in the human serum which is presumed to be generated through a T-independent response.

T-Cell Proliferation Study

Figure 37:
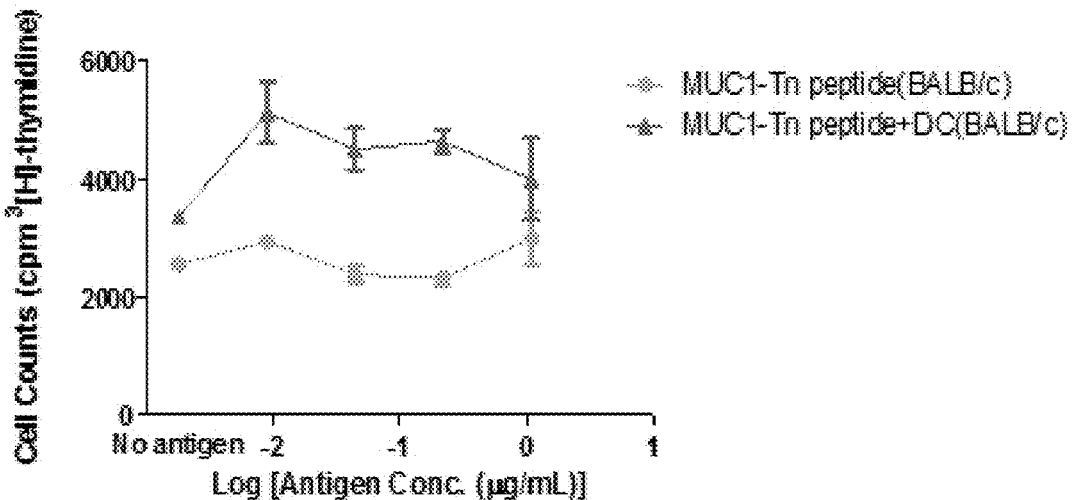
FIG. 37: T-Cell Proliferation in BALB/c mice with MUC1-Tn (10) Peptide in Presence and Absence of Dendritic Cells.
Figure 38A:
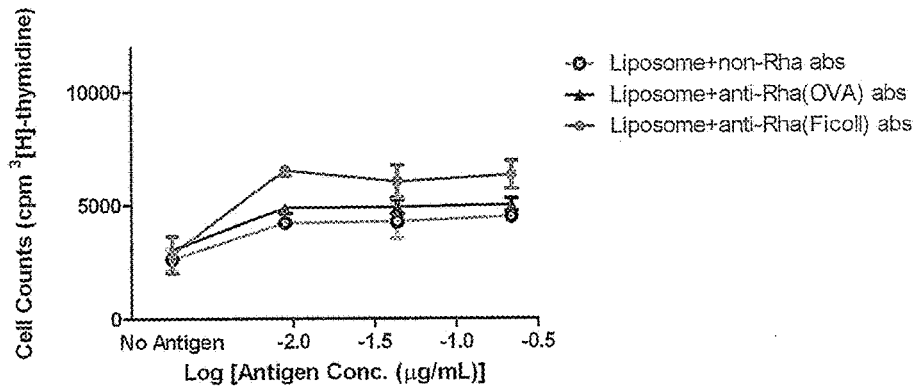
FIGS. 38A-38B.

T-cell proliferation assays were performed to determine if the combination of anti-Rha antibodies and Rha-modified liposomal vaccine would potentiate a T-cell proliferative response. In the first part of the study, the proliferation assay conditions were optimized. BALB/c mice were immunized (day 0) and boosted (days 14, 28, and 42) with 100 µL, emulsions of MUC1-Tn (8)/Sigma adjuvant system (SAS) (50 µg peptide per mouse, each injection). The mice were sacrificed (day 49), the spleens were removed, and single cell suspensions were prepared and incubated with MUC1-Tn ($8.8 \times 10^{-3}$-1.1 µg/mL) alone or with syngeneic bone marrow dendritic cells (DCs) previously pulsed with the same doses of antigen. DCs showed enhanced proliferation, as shown in FIG. 37. To test the ability of anti-Rha antibodies to enhance antigen presentation, spleen cells from BALB/c mice immunized as above were prepared. DCs from BALB/c bone marrow were pulsed with the antigen by incubating with Pam$_3$Cys-MUC1-Tn+Rha liposomes at antigen concentrations of $8.8 \times 10^{-3}$-0.22 µg/mL together with antibodies isolated from either Rha-Ficoll or Rha-OVA immunized mice or nonimmune mice. The pulsed DCs were added to the spleen cells and proliferation assessed after 3 days. The spleen T-cells proliferated better in the presence of anti-Rha antibodies (from both Rha-Ficoll and Rha-OVA immunized mice serum) than in the presence of control serum antibodies over the antigen concentration range of $8.8 \times 10^{-3}$-0.22 µg/mL. See FIG. 38A. Also, the T-cell proliferation was higher in the presence of anti-Rha antibodies generated against Rha-Ficoll (6328, 6045, and 6521 counts per minute (cpm) at antigen concentrations of $8.8 \times 10^{-3}$, 0.044, and 0.22 µg/mL) than those against Rha-OVA (5018, 4926, and 4880 cpm at antigen concentrations of $8.8 \times 10^{-3}$, 0.044, and 0.22 µg/mL), even though the titer of anti-Rha antibodies was higher in the serum of Rha-OVA immunized mice. The results strongly suggest that the Rha-modified antigen was more effectively internalized and presented by the APCs in the presence of anti-Rha antibodies, particularly those less inhibitory isotypes characteristic of natural antibodies and generated by Rha-Ficoll immunization. Therefore, BALB/c mice in which anti-Rha antibodies are generated with Rha-Ficoll (14) immunization are an appropriate model for the immunogenicity of the Rha-conjugated MUC1-Tn liposomes.

Anti-Rha Antibody Generation

Figure 38B:
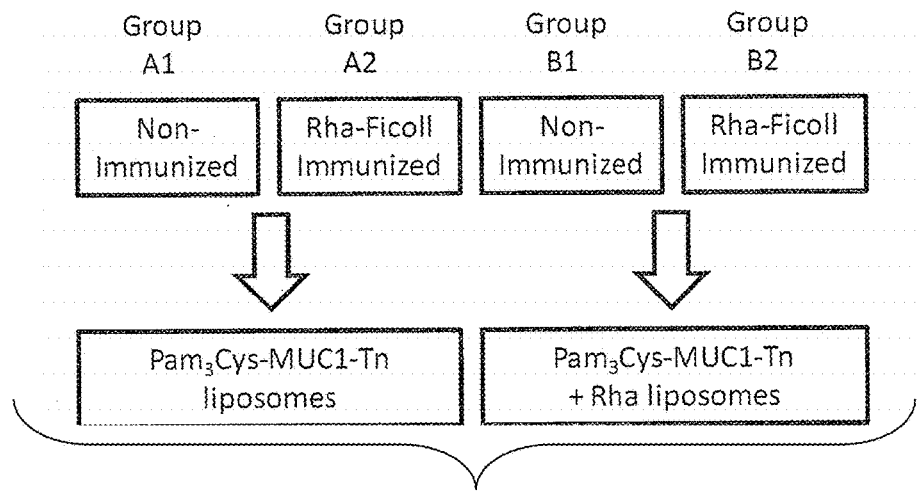
Figure 39A:
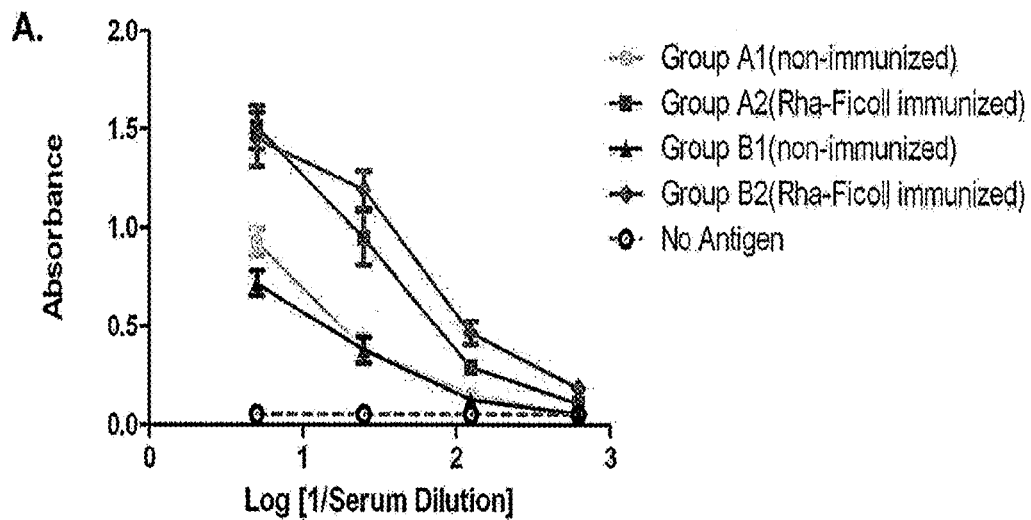
FIGS. 39A-39B.

Four groups of five female BALB/c mice each (groups A1, A2, B1, and B2) (6-8 weeks old) were used for this vaccination study. Groups A2 and B2 were immunized (day 0) and boosted (days 14, 28, 42, and 56) with 100 µL equivolume emulsion of Rha-Ficoll (prepared in PBS) and alum adjuvant. Groups A1 and B1 served as the control groups and were deprived of the Rha-Ficoll/Alum immunization. See FIG. 38B. The mice were bled on day 66 and the ELISA performed by screening the sera from the different groups against Rha-BSA showed that the anti-Rha antibody titers in groups A2 and B2 were 25-fold higher than the control groups. See FIG. 39. Thus, immunization with Rha-Ficoll confirmed the generation of anti-Rha antibodies in the experimental groups of mice.

Vaccination with Rha and non-Rha-Displaying MUCA1-Tn Liposomes

Two separate liposomal formulations were prepared. The first contained DPPC, cholesterol and Pam$_3$Cys-MUC1-Tn (9) (2 nmol) (Pam$_3$Cys-MUC1-Tn liposomes) and the second contained DPPC, cholesterol, Rha-TEG-cholesterol (3) and Pam$_3$Cys-MUC1-Tn (9) (2 nmol) (Pam$_3$CysMUC1-Tn+Rha liposomes). In both formulations the total lipid concentration was 30 mmol. The vaccination was performed on day 77. Groups A1 and A2 were given 100 µL subcutaneous injections of the Pam$_3$Cys-MUC1-Tn liposomes (2 nmol of peptide per mouse) and groups B1 and B2 were given 100 µL subcutaneous injections of the Pam$_3$CysMUC1-Tn+Rha liposome (2 nmol peptide per mouse). The mice were boosted on day 91 with either the Pam$_3$CysMUC1-Tn liposome (groups A1 and A2, 2 nmol peptide per mouse) or the Pam$_3$CysMUC1-Tn+Rha liposome (groups B1 and B2). The mice were bled on day 101 and the sera evaluated for anti-MUC1-Tn and anti-Tn antibodies. See FIG. 39B.

Figure 39B:
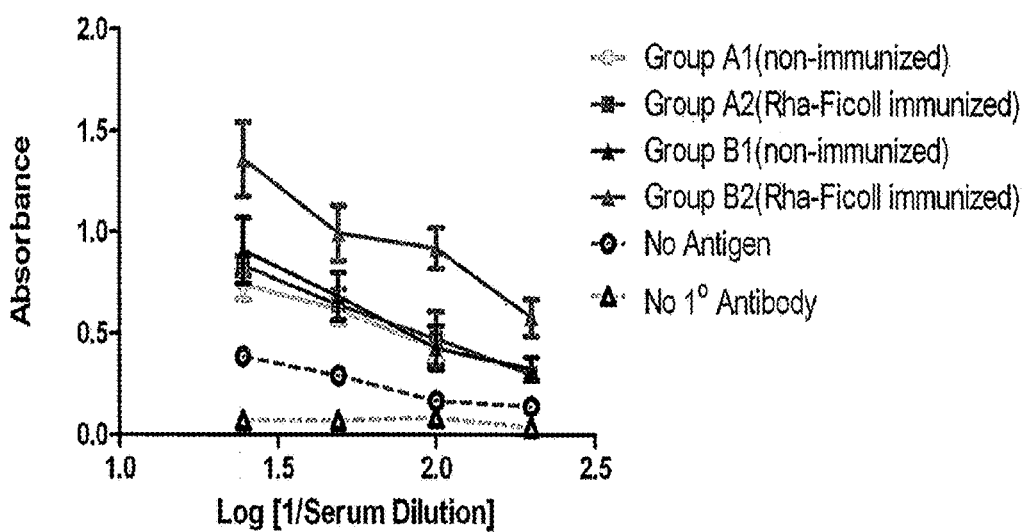
Figure 40:
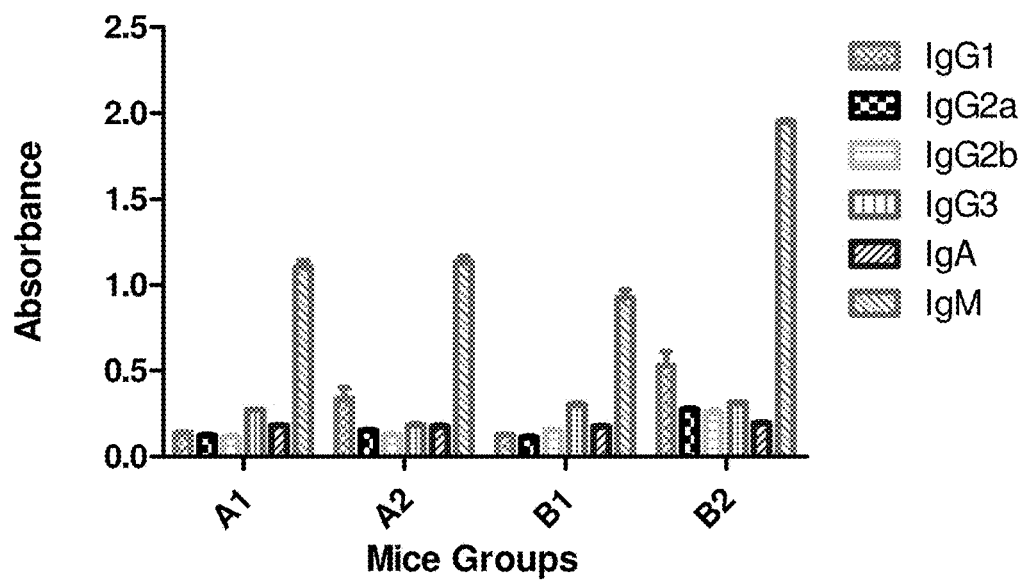
FIG. 40: Anti-MUC1-Tn Antibody Isotype Titers after first boost with Pam$_3$Cys-MUC1-Tn liposomes or Pam$_3$Cys-MUC1-Tn+Rha liposomes at 1/50 Serum Dilutions.
Figure 41A:
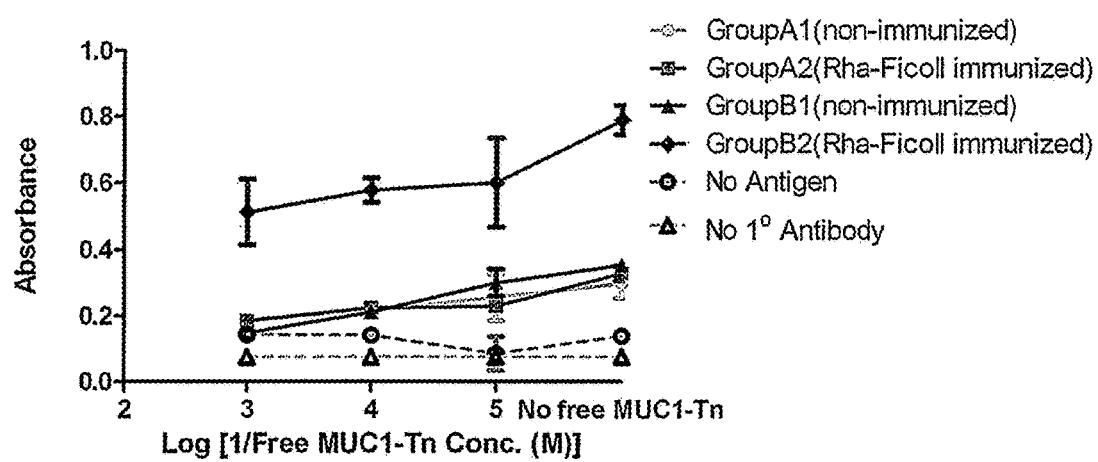
FIGS. 41A-41B.

Anti-MUC1-Tn antibody titers were determined by screening the sera against the MUC1-Tn conjugate (8). (FIG. 39B). The data showed that groups A1, A2, and B1 had similar absorbance at 1/25, 1/50, 1/100, and 1/200 serum dilutions. This proved that prior immunization with Rha-Ficoll does not affect the response to a non-Rha conjugated vaccine (groups A1 and A2). In addition, the Rha epitopes on the vaccine do not alter the inherent immunogenicity of the MUC1-Tn epitopes on the vaccine (groups A1 and B1). The anti-MUC1-Tn titers for group B2 showed an 8-fold increase compared to groups A1, A2, and B1, which was mediated by the anti-Rha antibody-dependent antigen-uptake. Group B2 had an anti-MUC1-Tn titer of approximately 1/300, where titer is defined as the highest dilution giving a signal >0.1 above background. The anti-Muc1-Tn antibodies from each group were isotyped, resulting in group B2 showing an increase in IgG1, IgG2a, IgG2b, and IgM isotypes relative to the other three groups. See FIG. 40. The specificity of the antibodies towards MUC1-Tn antigen was determined by a competitive binding experiment. See FIG. 41A. Serum from every group at 1/100 dilution was incubated with the MUC1-Tn conjugate (8) at concentrations of 0, $10^{-5}$, $10^{-4}$, and $10^{-3}$ M in 0.01 M PBS prior to addition in the ELISA plates coated with the conjugate (8). The absorbances decreased uniformly with increasing concentrations of free MUC1-Tn in the serum dilutions for each group. As an example, the absorbances at 620 nm for the serum dilution of group B2 at free MUC1-Tn concentrations of 0, $10^{-5}$, $10^{-4}$, and $10^{-3}$ M were 0.790, 0.601, 0.577, and 0.512, respectively. These results confirmed the specificity of the anti-MUC1-Tn antibodies towards the respective antigen.

Figure 41B:
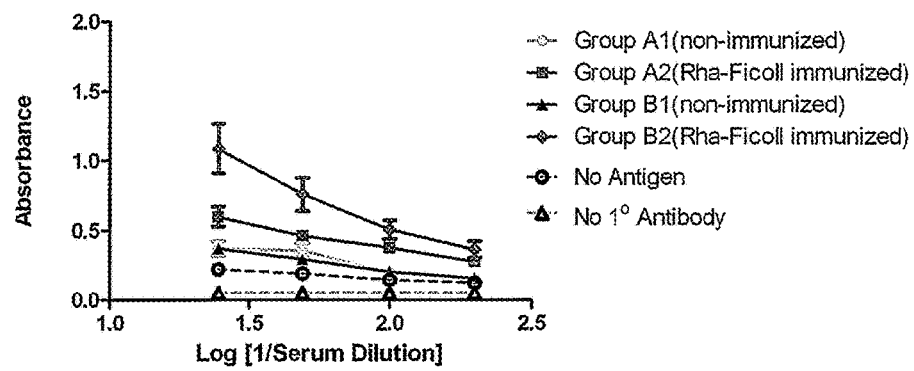

The antibody titer generated solely against the TACA was determined by screening serum dilutions from every group against a Tn-BSA conjugate. See FIG. 41B. A >8-fold increase in the anti-Tn antibody titers for group B2 was also observed in comparison to groups A1, A2, and B1. This was again attributed to the better uptake of the antigen in the presence of the anti-Rha antibodies by an antibody-dependent antigen-uptake mechanism. Also observed in this study was that the anti-MUC1-Tn antibody titers were higher than the corresponding anti-Tn antibody titers for the same serum dilutions for every group, assuming similar levels of antigen on the plate. For example, for the group B2, the absorbances at 620 nm for the anti-MUC1-Tn and the anti-Tn measurements at 1/100 serum dilutions were 0.922 and 0.509, respectively. This observation demonstrates that the Rha-displaying MUC1-Tn vaccine successfully generates antibodies against both the MUC1 peptide and the TACA.

Figures 42A, 42B:
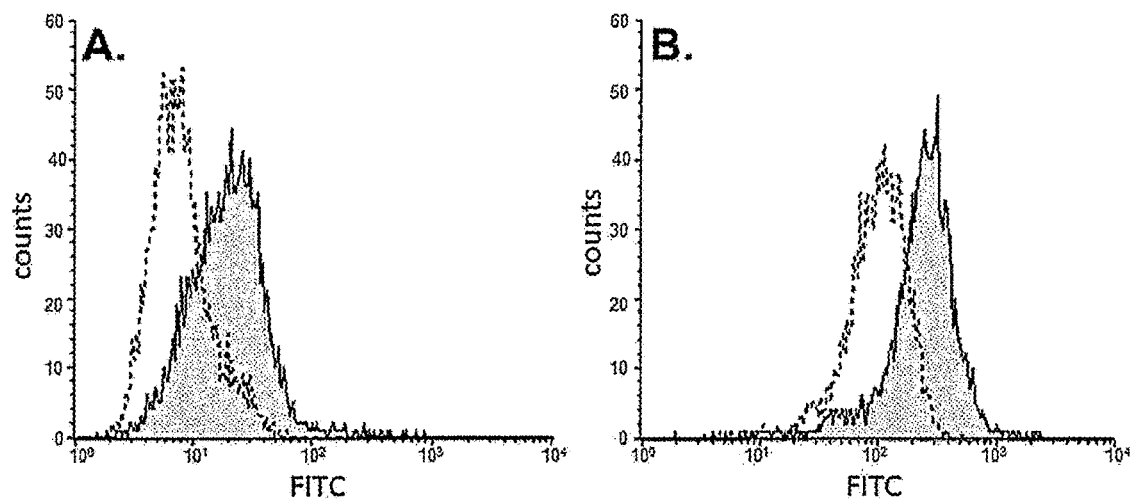
FIGS. 42A-42B: Binding of anti-MUC1-Tn antibodies to human leukemia U266 cells.

The ability of the anti-MUC1-Tn antibodies in the vaccinated mice serum to bind to MUC1-Tn on human tumor cells was demonstrated with U266 human leukemia cells. These cells express MUC1 on their surface as shown by binding with mouse anti-human MUC1 antibodies (CD 227). See FIG. 42A. Serum from group B2 mice also recognized the MUC1 on the tumor cells with similar efficiency as the CD 227 antibodies relative to non-immunized mouse serum. See FIG. 42B. This demonstrates that the antibodies generated against the glycopeptides recognize the MUC1 protein in its native environment.

Summary

As the examples herein describe, a fully synthetic two-component vaccine containing the lipopeptide adjuvant Pam₃Cys appended to a 20-amino acid MUC1 peptide containing the TACA GalNAc-O-Thr (Tn) was synthesized and was successfully formulated into liposomes along with an Rha cholesterol conjugate. The resulting liposomes were homogenous in size and were stable at 4° C. for two days. Binding studies with both anti-Rha and mouse anti-human MUC1 antibodies revealed that the Rha and the MUC1 glycopeptide epitopes were surface displayed on the liposomes. A Rha-Ficoll conjugate (14) was synthesized for the generation of anti-Rha antibodies in mice. The in vitro proliferation of MUC1-Tn primed mice spleen T-cells showed increased proliferation to Rha-liposomes in the presence of antibodies from Rha-Ficoll immunized mice relative to nonimmune mice. Vaccination studies with Rha- and non-Rha-displaying MUC1-Tn liposomes in mice either non-immunized or immunized with Rha-Ficoll illustrated that anti-MUC1-Tn and anti-Tn antibodies were >8-fold higher in the groups of mice previously immunized with Rha-Ficoll and later vaccinated with the Pam₃Cys-MUC1-Tn+Rha liposomes. The anti-MUC1-Tn antibodies in the serum of the vaccinated mice recognized the aberrant MUC1 on human leukemia U266 cells. Overall, this vaccine successfully triggered both T-cell and humoral immunity enhanced by anti-Rha antibody dependant antigen uptake. Because this vaccine uses separate rhamnose and anti-genic epitope components, the vaccine can easily be targeted to different antigens or epitopes by changing the peptide without having to change the other components. For instance, the skilled practitioner will appreciate that anti-viral or anti-bacterial vaccines can also be made from them methods and compositions described herein.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A composition, comprising:

an antigen composition consists essentially of one of compounds 9, 17, or 21:

9
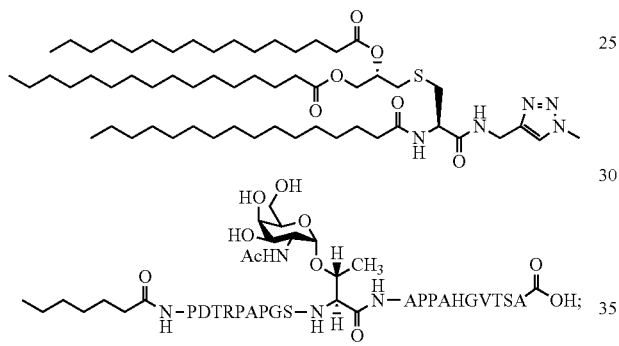

17
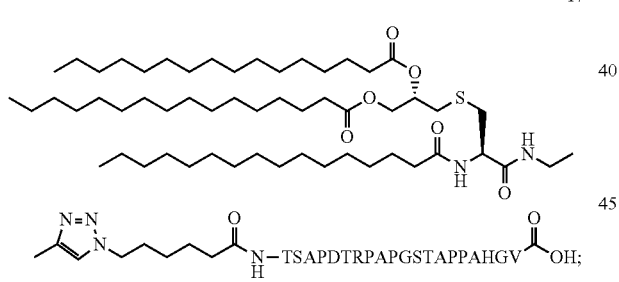

21
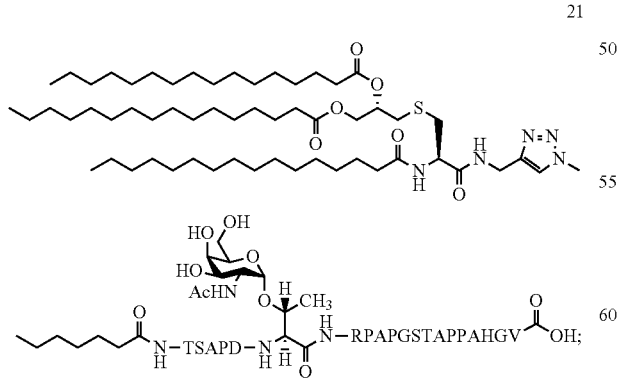

a xenoantigen composition comprising a second lipid moiety, a second linker moiety, and a xenoantigen moiety; and at least one liposomal formulation, wherein the antigen composition and the xenoantigen composition are embedded in the liposomal formulation;

wherein:

the xenoantigen moiety contains a structure comprising: an α- or β-linked L-rhamnose epitope, a β-linked α-Gal disaccharide epitope, or an α- or β-linked Forssman disaccharide epitope:

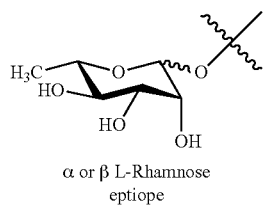

α or β L-Rhamnose eptiope

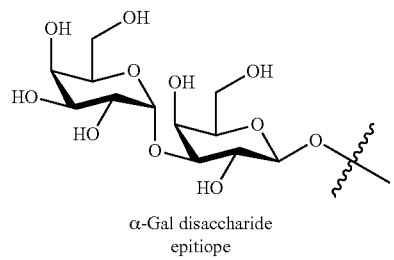

α-Gal disaccharide epitiope

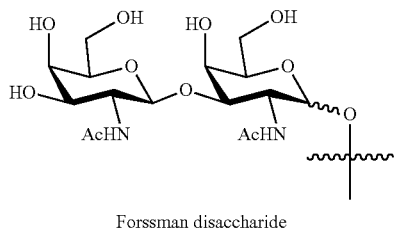

Forssman disaccharide epitiope and the second linker moiety comprises a chain of $C_{1-m}$ alkyl, dialkyl substituted aryl $C_{1-m}$ alkyl, or —$CH_2CH_2$($OCH_2CH_2$)$_m$—, wherein m is a positive integer.

2. The composition of claim 1, wherein the second lipid moiety contains a structure of the Formula IX:

IX

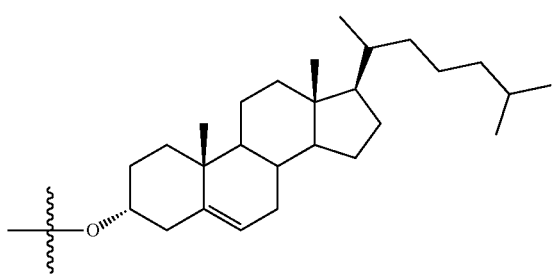

3. The composition of claim 1, wherein the second linker moiety comprises a tetraethyleneglycol (TEG) of Formula VIII:

VIII

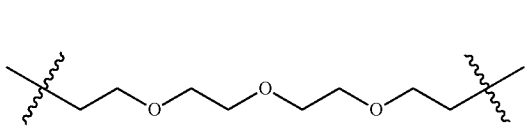

4. The composition of claim 1, wherein the liposomal formulation comprises 1,2-dipalmitoyl-sn-glycero-3-phosphocholine (DPPC) and cholesterol in a ratio of from about 80:20 to about 70:30, respectively.

5. The composition of claim 1, further including at least one immunologic adjuvant selected from the group consisting of: a saponin, monophosphoryl lipid A, 3-O-deacylated monophosphoryl lipid A, and interleukin 12.

6. A composition, comprising:
an antigen composition comprising a first lipid moiety, a first linker moiety, and an antigen moiety;
a xenoantigen composition comprising a second lipid moiety, a second linker moiety, and a xenoantigen moiety; and
at least one liposomal formulation, wherein the antigen composition and the xenoantigen composition are embedded in the liposomal formulation;
wherein:
the antigen moiety comprises a Pam₃Cys-MUC1 VNTR-TACA conjugate;
the first lipid moiety comprises a Toll-like receptor (TLR) agonist ligand;
the first linker moiety comprises a chain of $C_{1-n}$ alkyl, dialkyl substituted aryl $C_{1-n}$ alkyl, or —CH₂CH₂(OCH₂CH₂)$_n$—, wherein n is a positive integer; and
the xenoantigen moiety comprises α- or β-linked L-rhamnose.

7. The composition of claim 6, wherein the TACA comprises: TF, Tn, sialyl Tn (sTn), or sialyl Lewis a (sLe$^a$) antigens:

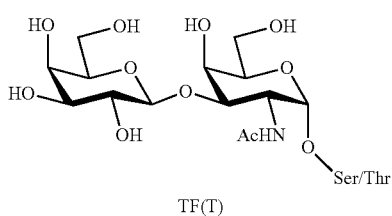
TF(T)

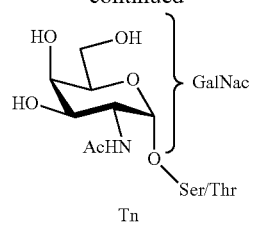
Tn

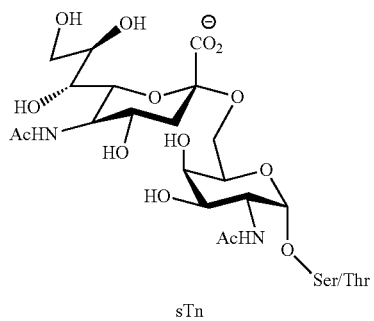
sTn

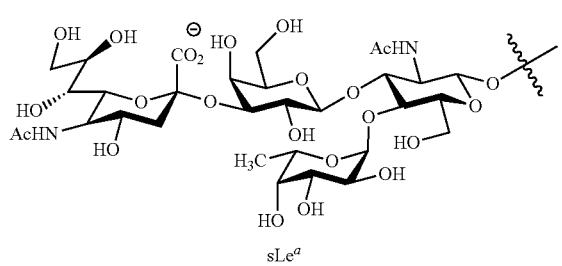
sLe$^a$

8. The composition of claim 6, wherein the TACA comprises an autologous or heterologous helper T-cell epitope, wherein the autologous or heterologous helper T-cell epitope comprises a sequence expressed on a tumor cell.

9. The composition of claim 8, wherein the autologous or heterologous helper T-cell epitope comprises a mucin 1 (MUC1) variable number tandem repeat (VNTR) having one of the following amino acid sequences:

PDTRPAPGST(Tn)APPAHGVTSA [SEQ ID NO: 1];

TSAPDTRPAPGSTAPPAHGV [SEQ ID NO: 5]; or

TSAPDT(Tn)RPAPGSTAPPAHGV [SEQ ID NO: 6].

10. The composition of claim 9, wherein the threonine in the sequence GST or PDT is synthetically modified to incorporate α-GalNAc-O-Thr (Tn) TACA.

11. A composition, comprising:
an antigen composition comprising a first lipid moiety, a first linker moiety, and an antigen moiety;
a xenoantigen composition comprising a second lipid moiety, a second linker moiety, and a xenoantigen moiety; and
at least one liposomal formulation, wherein the antigen composition and the xenoantigen composition are embedded in the liposomal formulation;
wherein the antigen composition consists essentially of compound 21:

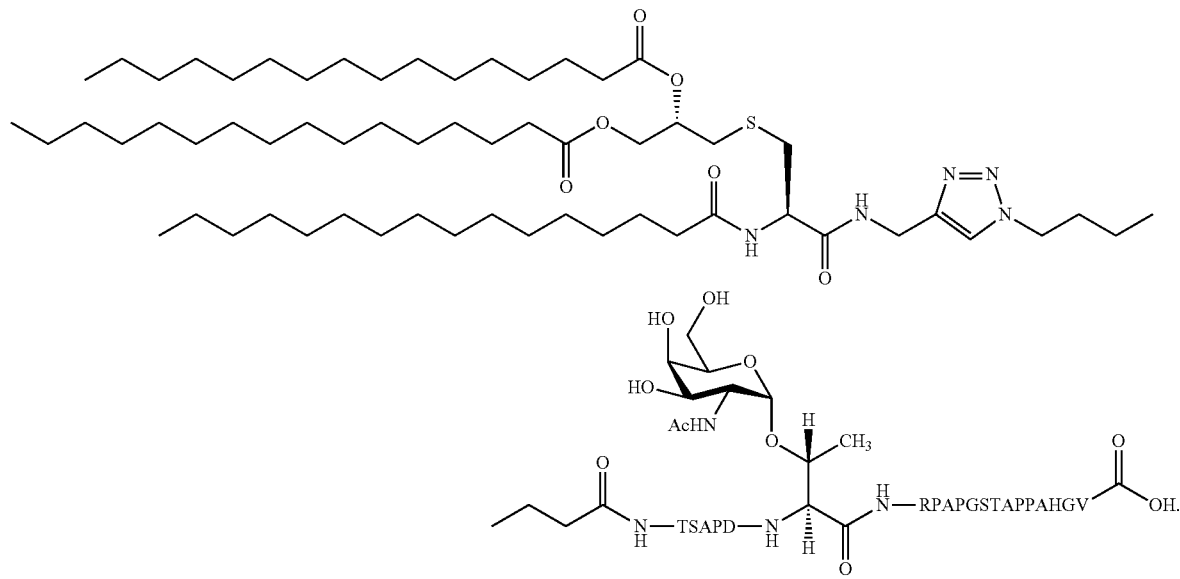

12. A composition comprising:

an antigen composition comprising a first lipid moiety, a first linker moiety, and an antigen moiety, wherein the antigen composition comprises a Pam₃Cys-MUC1 VNTR-TACA conjugate;

a xenoantigen composition comprising a second lipid moiety, a second linker moiety, and a xenoantigen moiety, wherein the second linker moiety comprises a tetraethyleneglycol (TEG) portion and the xenoantigen moiety comprises α- or β-linked L-rhamnose; and at least one liposomal formulation, wherein the antigen composition and the xenoantigen composition are embedded in the liposomal formulation.

* * * * *